United States Patent [19]

Himmelsbach et al.

[11] Patent Number: 5,707,989
[45] Date of Patent: Jan. 13, 1998

[54] PYRIMIDO[5,4-D]PYRIMIDINES, MEDICAMENTS COMPRISING THESE COMPOUNDS, THEIR USE AND PROCESSES FOR THEIR PREPARATION

[75] Inventors: Frank Himmelsbach, Mittelbiberach, Germany; Thomas von Rüden, Wien, Austria; Georg Dahmann, Biberach, Germany; Thomas Metz, Wien, Austria

[73] Assignee: Dr. Karl Thomae GmbH, Biberach an der Riss, Germany

[21] Appl. No.: 524,707

[22] Filed: Sep. 7, 1995

[30] Foreign Application Priority Data

| Sep. 7, 1994 | [DE] | Germany | 44 31 867.7 |
| Feb. 1, 1995 | [DE] | Germany | 195 03 151.2 |
| Jun. 13, 1995 | [DE] | Germany | 195 21 386.6 |
| Aug. 4, 1995 | [DE] | Germany | 195 28 672.3 |

[51] Int. Cl.⁶ .................... C07D 413/14; C07D 417/14; A61K 31/54; A61K 31/535
[52] U.S. Cl. .................... 514/228.2; 514/234.2; 514/258; 544/61; 544/122
[58] Field of Search .................... 514/258, 228.2, 514/234.2; 544/256, 61, 122

[56] References Cited

U.S. PATENT DOCUMENTS

| 3,031,450 | 4/1962 | Gottwalt et al. | 544/256 |
| 4,478,833 | 10/1984 | Roch et al. | 424/246 |
| 4,518,596 | 5/1985 | Roch et al. | 514/232 |
| 4,714,698 | 12/1987 | Roch et al. | 514/212 |
| 5,034,393 | 7/1991 | Hackler et al. | 514/258 |
| 5,618,814 | 4/1997 | Heckel et al. | 514/234.2 |

*Primary Examiner*—Matthew V. Grumbling
*Attorney, Agent, or Firm*—R. P. Raymond; M-E. M. Devlin; A. R. Stempel

[57] ABSTRACT

The present invention relates to pyrimido[5,4-d]pyrimidines of the general formula

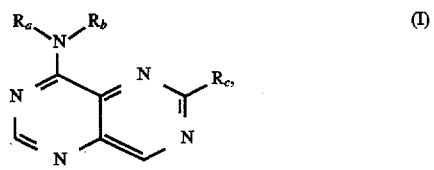

(I)

in which $R_a$ to $R_c$ are as defined herein, their tautomers, their stereoisomers and their salts, in particular their physiologically tolerated salts with inorganic or organic acids or bases which have valuable pharmacological properties, in particular an inhibiting action on signal transduction mediated by tyrosine kinases, their use for the treatment of diseases, in particular tumor diseases.

11 Claims, No Drawings

PYRIMIDO[5,4-D]PYRIMIDINES, MEDICAMENTS COMPRISING THESE COMPOUNDS, THEIR USE AND PROCESSES FOR THEIR PREPARATION

The present invention relates to pyrimido[5,4-d] pyrimidines of the general formula

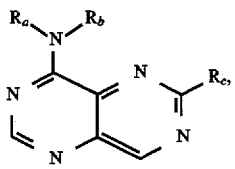

their tautomers, their stereoisomers and their salts, in particular their physiologically tolerated salts with inorganic or organic acids or bases which have valuable pharmacological properties, in particular an inhibiting action on the signal transduction mediated by tyrosine kinases, their use for the treatment of diseases, in particular tumour diseases, and their preparation.

In the above general formula I $R_a$ is a hydrogen atom or an alkyl group, $R_b$ is a phenyl group which is substituted by the radicals $R_1$ to $R_3$, wherein $R_1$ and $R_2$, which can be identical or different, are each a hydrogen, fluorine, chlorine, bromine or iodine atom, a $C_{1-6}$-alkyl, hydroxyl or $C_{1-6}$alkoxy group, a $C_{3-7}$-cycloalkyl or $C_{4-7}$-cycloalkoxy group, each of which can be substituted by one or two alkyl groups or by an aryl group, a $C_{2-5}$-alkenyl or $C_{3-5}$-alkenyloxy group which is optionally substituted by an aryl group, wherein the vinyl part cannot be linked to the oxygen atom, a $C_{2-5}$-alkynyl or $C_{3-5}$-alkynyloxy group which is optionally substituted by an aryl group, wherein the ethynyl part cannot be linked to the oxygen atom, an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphinyl, trifluoromethylsulphonyl, arylsulphenyl, arylsulphinyl, arylsulphonyl, aralkylsulphenyl, aralkylsulphinyl or aralkylsulphonyl group, a methyl or methoxy group which is substituted by 1 to 3 fluorine atoms, a $C_{2-4}$-alkyl or $C_{2-4}$-alkoxy group which is substituted by 1 to 5 fluorine atoms, a nitro, amino, alkylamino, dialkylamino, $C_{3-7}$-cycloalkylamino, N-alkyl-$C_{3-7}$-cycloalkylamino, arylamino, N-alkylarylamino, aralkylamino or N-alkyl-aralkylamino group, a 4- to 7-membered alkylenimino group which is optionally substituted by 1 to 4 alkyl groups, wherein, in the abovementioned 5- to 7-membered alkylenimino groups, in each case one or two methylene groups adjacent to the nitrogen atom can in each case be replaced by a carbonyl group, or in the abovementioned 6- to 7-membered alkylenimino groups, a methylene group in the 4-position can be replaced by an oxygen or sulphur atom or by a sulphinyl, sulphonyl, imino, N-alkylimino, N-alkyl-carbonyl-imino, N-alkylsulphonyl-imino, N-arylimino or N-aralkylimino group, an (alkylenimino)carbonyl or (alkylenimino)sulphonyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino, N-alkyl-imino, N-alkylcarbonyl-imino, N-alkylsulphonylimino, N-aryl-imino or N-aralkyl-imino group, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-aryl-sulphonylamino, aralkylcarbonylamino, N-alkylaralkylcarbonylamino, aralkylsulphonylamino, N-alkylaralkylsulphonylamino, perfluoroalkylsulphonylamino, N-alkylperfluoroalkylsulphonylamino, alkylcarbonyl, arylcarbonyl, aralkylcarbonyl, aryl-hydroxymethyl, aralkyl-hydroxymethyl, carboxyl, alkoxycarbonyl, aralkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkylaralkylaminocarbonyl, N-hydroxy-aminocarbonyl, N-hydroxyalkylaminocarbonyl, N-alkoxy-aminocarbonyl, N-alkoxyalkylaminocarbonyl, cyano, azido, N-cyano-amino or N-cyanoalkylamino group, a sulpho, alkoxysulphonyl, aminosulphonyl, alkylaminosulphonyl, dialkylaminosulphonyl, arylaminosulphonyl, N-alkylarylaminosulphonyl, aralkylaminosulphonyl or N-alkylaralkylaminosulphonyl group, a phosphono, O-alkyl-phosphono, O,O'-dialkyl-phosphono, O-aralkyl-phosphono or O,O'-diaralkyl-phosphono group, an alkyl or alkoxy group which is substituted by $R_4$, wherein $R_4$ is a hydroxyl, alkoxy, aryloxy, aralkoxy, amino, alkylamino, dialkylamino, alkylsulphenyl, alkylsulphinyl, alkylsulphonyl, arylsulphenyl, arylsulphinyl, arylsulphonyl, aralkylsulphenyl, aralkylsulphinyl, aralkyl sulphonyl, carboxyl, alkoxycarbonyl, aminocarbonyl, alkylaminocarbonyl, dialkylaminocarbonyl or cyano group, a 4- to 7-membered alkylenimino group which is optionally substituted by 1 to 4 alkyl groups, wherein, in the abovementioned 5- to 7-membered alkylenimino groups, in each case one or two methylene groups adjacent to the nitrogen atom can be replaced by a carbonyl group, or in the abovementioned 6- to 7-membered alkylenimino groups, a methylene group in the 4-position can be replaced by an oxygen or sulphur atom or by a sulphinyl, sulphonyl, imino, N-alkyl-imino, N-alkylcarbonylimino, N-alkylsulphonyl-imino, N-aryl-imino or N-aralkyl-imino group, or an (alkylenimino)carbonyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino, N-alkyl-imino, N-alkylcarbonyl-imino, N-alkyl sulphonyl-imino, N-aryl-imino or N-aralkyl-imino group, $R_3$ is a hydrogen, fluorine, chlorine or bromine atom, an alkyl, alkoxy or trifluoromethyl group or $R_2$ together with $R_3$, if these are bonded to adjacent carbon atoms, is a methylenedioxy group which is optionally substituted by one or two alkyl groups, an n-$C_{3-6}$-alkylene group which is optionally substituted by one or two alkyl groups, or a 1,3-butadiene-1,4-diylene group which is optionally substituted by one or two fluorine, chlorine, bromine or iodine atoms or by one or two hydroxyl, alkyl, alkoxy, trifluoromethyl or cyano groups, wherein the substituents can be identical or different, or $R_a$ together with $R_1$, if $R_1$ is in the o-position relative to the nitrogen atom which is substituted by $R_a$, is an n-$C_{2-4}$-alkylene group which is optionally substituted by one or two alkyl groups, and $R_c$ is a hydrogen, fluorine, chlorine, bromine or iodine atom, an alkyl, $C_{3-7}$-cycloalkyl, $C_{3-7}$-cycloalkyl-$C_{1-3}$-alkyl, aryl, aralkyl, hydroxyl, aryloxy, aralkoxy, mercapto, $C_{1-8}$-alkylsulphenyl, $C_{1-8}$-alkylsulphinyl, $C_{1-8}$-alkylsulphonyl, $C_{4-7}$-cycloalkylsulphenyl, $C_{4-7}$-cycloalkylsulphinyl, $C_{4-7}$-cycloalkylsulphonyl, $C_{3-7}$-cycloalkyl-$C_{1-3}$-alkylsulphenyl, $C_{3-7}$-cycloalkyl-$C_{1-3}$-alkylsulphinyl, $C_{3-7}$-cycloalkyl-$C_{1-3}$-alkylsulphonyl, arylsulphenyl, arylsulphinyl, arylsulphonyl, aralkylsulphenyl, aralkylsulphinyl or aralkylsulphonyl group, a $C_{1-8}$-alkoxy group, which can be substituted by an alkoxycarbonyl, cyano, carboxyl, aminocarbonyl, alkylaminocarbonyl or dialkylaminocarbonyl group, a $C_{2-8}$-alkoxy group substituted by a hydroxyl, alkoxy, hydroxy-$C_{2-4}$-alkylamino, amino, alkylamino, dialkylamino, alkylcarbonylamino, N-alkyl-N-(alkylcarbonyl)amino, alkylsulphonylamino, N-alkyl-N-(alkylsulphonyl)amino, alkoxycarbonylamino or N-alkyl-N-(alkoxycarbonyl)amino group, by a 5- to 7-membered alkylenimino group which is optionally substituted by 1 to 4 alkyl groups, wherein, in the abovementioned 5- to 7-membered alkylenimino groups, in each case one or two methylene groups adjacent to the nitrogen atom can be replaced by a carbonyl group, and additionally in the abovementioned 6- to 7-membered alkylenimino groups, a methylene group in the 4-position can be replaced by an oxygen or sulphur atom or by a carbonyl, sulphinyl, sulphonyl, imino, N-alkyl-imino, N-alkylcarbonyl-imino, N-formyl-imino, N-dialkylaminocarbonyl-imino, N-alkoxy-carbonyl-imino, N-alkylsulphonyl-imino, N-aryl-imino or N-aralkyl-imino group, a $C_{3-8}$-alkoxy group substituted by two hydroxyl or alkoxy groups, a $C_{1-8}$-alkoxy group substituted by a $C_{3-7}$-cycloalkyl group wherein in each case the cycloalkyl residue can be substituted by 1 to 4 alkyl groups, and wherein, in the abovementioned $C_{4-7}$-cycloalkyl residues, in each case a methylene group can be replaced by an oxygen or sulphur atom or by a carbonyl, sulphinyl, sulphonyl, imino, N-alkyl-imino, N-alkylcarbonylimino, N-alkoxycarbonyl-imino, N-alkylsulphonyl-imino, N-arylimino or N-aralkyl-imino group, a $C_{4-7}$-cycloalkoxy group which is optionally substituted by one or two hydroxyl groups or by an alkoxy, alkoxycarbonyl, cyano, carboxyl, amino-carbonyl, alkylaminocarbonyl, dialkylaminocarbonyl, hydroxy-$C_{2-4}$-alkylamino, amino, alkylamino, dialkylamino, alkylcarbonyl-amino, N-alkyl-N-(alkylcarbonyl)amino, alkylsulphonylamino, N-alkyl-N-(alkylsulphonyl)amino, alkoxycarbonylamino or N-alkyl-N-(alkoxycarbonyl)amino group, wherein, in the abovementioned $C_{5-7}$-cycloalkoxy groups, in each case a methylene group can be replaced by an oxygen or sulphur atom or by a sulphinyl, sulphonyl, imino, N-alkyl-imino, N-alkylcarbonyl-imino, N-alkoxycarbonyl-imino, N-alkylsulphonyl-imino, N-aryl-imino or N-aralkyl-imino group, a $C_{3-8}$-alkenyloxy group which is optionally substituted by an aryl group or $C_{3-7}$-cycloalkyl group, wherein the vinyl part cannot be linked to the oxygen atom, a $C_{3-8}$-alkynyloxy group which is optionally substituted by an aryl group or $C_{3-7}$-cycloalkyl group, wherein the ethynyl part cannot be linked to the oxygen atom, a 4- to 8-membered alkylenimino group which is optionally substituted by 1 to 4 alkyl groups or 1 to 2 aryl groups, and which can additionally be substituted by the radical $R_5$, wherein $R_5$ is an aryl, aralkyl, carboxyl, alkoxycarbonyl, aminocarbonyl, alkylaminocarbonyl, dialkylaminocarbonyl, cyano, hydroxyl, alkoxy, aryloxy, aralkoxy, alkylcarbonyloxy, arylcarbonyloxy, amino, alkylamino, hydroxy-$C_{2-4}$-alkylamino, dialkylamino, cyano-amino, formylamino, N-(alkyl)-N-(hydroxy-$C_{2-4}$-alkyl) amino or bis-(hydroxy-$C_{2-4}$-alkyl)amino group, an (alkylenimino)carbonyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino, N-alkyl-imino, N-alkyl-carbonyl-imino, N-alkylsulphonyl-imino, N-aryl-imino or N-aralkyl-imino group, a 4- to 7-membered alkylenimino group which is optionally substituted by 1 to 4 alkyl groups or a hydroxy-alkyl group, wherein, in the abovementioned 5- to 7-membered alkylenimino groups, in each case one or two methylene groups adjacent to the nitrogen atom can be replaced by a carbonyl group, a 6- or 7-membered alkyleneimino group which is optionally substituted by 1 to 4 alkyl groups or a hydroxyalkyl group, whereby in each case a methylene group in the 4-position of the alkyleneimino residue is replaced by an oxygen or sulphur atom or by a carbonyl, sulphinyl, sulphonyl, imino, N-alkyl-imino, N-alkylcarbonyl-imino, N-alkyl-sulphonyl-imino, N-aryl-imino or N-aralkyl-imino group, and additionally in the alkyleneimino residue of the abovementioned groups in each case one or two of the methylene groups adjacent to the nitrogen atoms can be replaced by a carbonyl group, a 4- to 7-membered alkylenimino group which is substituted by a hydroxyl, alkoxy, amino, alkylamino, dialkylamino, alkylcarbonylamino, N-alkyl-alkylcarbonylamino, alkylsulphonylamino, N-alkyl-alkylsulphonyl-amino or hydroxyalkyl group, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group, a $(NR_7R_8)$ $CONR_6$- or $(NR_7R_8)SO_2NR_6$— group, in which $R_6$, $R_7$ and $R_8$, which can be identical or different, are each a hydrogen atom or an alkyl group or $R_6$ and $R_7$ together are an n-$C_{2-4}$-alkylene group and $R_8$ is a hydrogen atom or an alkyl group, a carboxyalkyl, alkoxycarbonylalkyl, aminocarbonylalkyl, alkylaminocarbonylalkyl or dialkylaminocarbonylalkyl group, an (alkylenimino)carbonylalkyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino or N-alkyl-imino group, a (carboxyalkyl)oxy, (alkoxycarbonylalkyl)oxy, (aminocarbonylalkyl)oxy, (alkylaminocarbonylalkyl)oxy or (dialkylaminocarbonylalkyl)oxy group, an [(alkylenimino)carbonylalkyl]oxy group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino or N-alkyl-imino group, a cyanoalkyl, hydroxyalkyl, alkoxyalkyl, aryloxyalkyl, aminoalkyl, alkylaminoalkyl or dialkylaminoalkyl group, an (alkylenimino)alkyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino or N-alkyl-imino group, an alkylcarbonylaminoalkyl, N-alkyl-alkylcarbonylaminoalkyl, alkylsulphonylaminoalkyl, N-alkyl-alkylsulphonylaminoalkyl, arylcarbonylaminoalkyl, N-alkylarylcarbonylaminoalkyl, arylsulphonylaminoalkyl, N-alkyl-arylsulphonylaminoalkyl, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, alkylsulphenylalkyl, alkylsulphinylalkyl, alkylsulphonylalkyl, arylsulphenylalkyl, arylsulphinylalkyl or arylsulphonylalkyl group or a $C_{3-7}$-cycloalkyl group, wherein, in a $C_{5-7}$-cycloalkyl group, a methylene group can be replaced by an oxygen or sulphur atom or by a sulphinyl, sulphonyl, imino or N-alkylimino group, or $R_c$ is a 6- to 8-membered alkylenimino group which is optionally substituted by 1 to 4 alkyl groups or an aryl group and can additionally be substituted by the radical $R_5$, wherein, in the abovementioned alkylenimino groups, in each case a methylene group in the 4-position is replaced by an oxygen or sulphur atom or by a carbonyl, sulphinyl, sulphonyl, N-oxido-N-alkylimino or $R_9N$ group, wherein $R_9$ is a hydrogen atom, an alkyl, hydroxy-$C_{2-4}$-alkyl, alkoxy-$C_{2-4}$-alkyl, amino-$C_{2-4}$-alkyl, alkylamino-$C_{2-4}$alkyl, dialkylamino-$C_{2-4}$-alkyl, (hydroxy-$C_{2-4}$-alkoxy)$C_{2-4}$-alkyl, aminocarbonylalkyl, alkylaminocarbonylalkyl, dialkylaminocarbonylalkyl, aryl, aralkyl, formyl, alkylcarbonyl, alkylsulphonyl, arylcarbonyl, arylsulphonyl, aralkylcarbonyl, aralkylsulphonyl, alkoxycarbonyl, cyano, aminocarbonyl, alkylaminocarbonyl or dialkylaminocarbonyl group or an (alkylenimino)carbonyl group which has in each case 4 to 7 ring atoms in the alkylenimino part, wherein, in a 6- to 7-membered alkylenimino part, a methylene group in the 4-position can be replaced by an oxygen or sulphur atom or by a sulphinyl, sulphonyl, imino or N-alkyl-imino group, or $R_c$ is a 1-pyrrolidinyl group which is optionally substituted by 1 to 4 alkyl groups and in which two hydrogen atoms on the carbon skeleton are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 2 to 4 carbon atoms if the two hydrogen atoms are on carbon atoms which are separated by an atom, wherein the abovementioned 1-pyrrolidinyl groups can additionally be substituted by the radical $R_5$, which is defined as mentioned above, a 1-piperidinyl or 1-azacyclohept-1-yl group which is optionally substituted by 1 to 4 alkyl groups and in which two hydrogen atoms on the carbon skeleton are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 1 to 4 carbon atoms if the two hydrogen atoms are on carbon atoms which are separated by an atom, or contains 1 to 3 carbon atoms if the two hydrogen atoms are on carbon atoms which are separated by two-atoms, wherein the abovementioned 1-piperidinyl and 1-azacyclohept-1-yl groups can additionally be substituted by the radical $R_5$, which is defined as mentioned above, a 1-pyrrolidinyl group which is optionally substituted by 1 to 4 alkyl groups and in which two hydrogen atoms in the 3-position are substituted by a —O—$CH_2CH_2$—O— or —O—$CH_2CH_2CH_2$—O— group, a 1-piperidinyl or 1-azacyclohept-1-yl group which is optionally substituted by 1 to 4 alkyl groups and in which, in the 3-position or in the 4-position, in each case two hydrogen atoms are replaced by a —O—$CH_2CH_2$—O—or —O—$CH_2CH_2CH_2$—O— group, a group of the formula

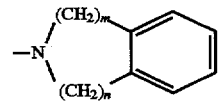

in which m and n, which can be identical or different, are the numbers 1 to 3 or m is the number 0 and n is the number 2, 3 or 4, wherein, additionally, the above benzo part can be mono- or disubstituted by fluorine, chlorine, bromine or iodine atoms or by alkyl, trifluoromethyl, hydroxyl, alkoxy or cyano groups and the above saturated cyclic imino part can be mono- or disubstituted by 1 or 2 alkyl groups, wherein the substituents can in each case be identical or different, or an $(R_{10}NR_{11})$ group, in which $R_{10}$ and $R_{11}$, which can be identical or different, are each a hydrogen atom, a $C_{1-6}$-alkyl group, which can be substituted by 1 or 2 aryl or $C_{3-7}$-cycloalkyl groups, by a carboxyl, alkoxycarbonyl, aminocarbonyl, alkylaminocarbonyl, dialkylaminocarbonyl, hydroxy-$C_{2-4}$-alkylaminocarbonyl, cyano, hydroxyl, alkoxy, aryloxy, aralkoxy, $C_{2-4}$-alkylenedioxy, alkylcarbonyloxy, arylcarbonyloxy, formylamino, amino, alkylamino or dialkylamino group, by an (alkylenimino)carbonyl group which has in each case 4 to 7 ring atoms in the alkylenimino part and is optionally substituted by 1 to 4 alkyl groups, wherein, in a 6- or 7-membered alkylenimino residue, in each case a methylene group in the 4-position can be replaced by an oxygen or sulphur atom or by a sulphinyl, sulphonyl, imino, N-alkylimino, N-alkylcarbonyl-imino, N-alkylsulphonyl-imino, N-arylimino or N-aralkylimino group, by a 4- to 7-membered alkylenimino group which is optionally substituted by 1 to 4 alkyl groups, wherein, in the abovementioned 6- or 7-membered alkylenimino groups, in each case a methylene group in the 4-position can be replaced by an oxygen or sulphur atom or by a sulphinyl, sulphonyl or $R_9N$ group, wherein $R_9$ is as defined above, and additionally in the abovementioned 5- to 7-membered alkylenimino groups, in each case one or two methylene groups adjacent to the nitrogen atoms can be replaced by a carbonyl group, by an alkylsulphonylamino, N-alkyl-alkylsulphonylamino, arylcarbonylamino, N-alkyl-arylcarbonyl-amino, alkylcarbonylamino, N-alkyl-alkylcarbonylamino, arylsulphonylamino, N-alkyl-arylsulphonylamino, aralkylcarbonylamino, N-alkylaralkyl carbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group, by an $(R_8NR_7)$—CO—$NR_6$— or $(R_8NR_7)$—$SO_2$—$NR_6$— group, wherein $R_6$, $R_7$ and $R_8$ are as defined above, by an alkylsulphenyl, alkylsulphinyl, alkylsulphonyl, arylsulphenyl, arylsulphinyl, arylsulphonyl, aralkylsulphenyl, aralkylsulphinyl or aralkylsulphonyl group, by a $C_{4-7}$-cycloalkyl group which is substituted by $R_5$ and optionally additionally by 1 to 4 alkyl groups, wherein $R_5$ is as defined above, by a $C_{5-7}$-cycloalkyl group which is optionally substituted by 1 to 4 alkyl groups and in which a methylene group is replaced by an oxygen or sulphur atom or by a sulphinyl, sulphonyl, or $NR_9$ group, or by a fluorine, chlorine, bromine or iodine atom, a $C_{2-10}$-alkyl group substituted by 2 or 3 fluorine atoms, a $C_{3-10}$-alkyl group substituted by 4 or 5 fluorine atoms, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a $C_{3-10}$-alkyl group which is substituted by 2 to 5 hydroxyl or alkoxy groups, a $C_{2-6}$-alkyl group which is substituted by an aryl group and a hydroxyl group and can additionally be substituted by an amino, alkylamino, dialkylamino, hydroxyl or alkoxy group, a $C_{3-10}$-alkyl group which is substituted by an amino, alkylamino, dialkylamino, alkylcarbonylamino or alkoxycarbonylamino group and additionally by a hydroxyl or alkoxy group, an alkenyl or alkynyl group which has in each case 3 to 6 carbon atoms and is optionally substituted by an aryl group or $C_{3-7}$-cycloalkyl group, wherein the vinyl or ethynyl part cannot be linked to the nitrogen atom, a $C_{2-4}$-alkyl group which is substituted by a $C_{2-4}$-alkoxy group which is substituted in the ω-position by a hydroxyl or alkoxy group, an aryl group, a cyclopropyl group which can be substituted by 1 or 2 alkyl groups, by an aryl, carboxyl, alkoxycarbonyl, aminocarbonyl, alkylaminocarbonyl or dialkylaminocarbonyl group or by an (alkylenimino)carbonyl group which has in each case 4 to 7 ring atoms in the alkylenimino part and is optionally substituted by 1 to 4 alkyl groups, wherein, in the abovementioned 6- or 7-membered alkylenimino parts, in each case a methylene group in the 4-position can be replaced by an oxygen or sulphur atom or by a sulphinyl, sulphonyl, imino, N-alkylimino, N-alkylcarbonyl-imino, N-alkylsulphonyl-imino, N-aryl-imino or N-aralkylimino group, a $C_{4-7}$-cycloalkyl group which is optionally substituted by 1 to 4 alkyl groups and can additionally be substituted by $R_5$, which is as defined above, a $C_{5-7}$-cycloalkyl group which is optionally substituted by 1 to 2 alkyl groups and is additionally substituted by an N,N-dialkyl-N-oxido-amino group, a $C_{5-7}$-cycloalkenyl group which is optionally substituted by 1 to 4 alkyl groups, wherein the vinyl part cannot be linked to the nitrogen atom of the $(R_{11}NR_{10})$— group, a $C_{4-7}$-cycloalkyl group which is optionally substituted by 1 to 4 alkyl groups and can additionally be substituted by $R_5$, wherein, in the cycloalkyl part, a methylene group is replaced by an oxygen or sulphur atom or by a sulphinyl, sulphonyl, N-alkyl-N-oxido-imino or $R_9N$ group, wherein $R_5$ and $R_9$ are as defined above, a $C_5$-$C_7$-cycloalkyl or $C_5$-$C_7$-cycloalkylalkyl group which is optionally substituted by 1 to 4 alkyl groups and in which in each case a methylene group in the cycloalkyl part is replaced by a carbonyl group, a cyclopentyl or cyclopentylalkyl group which is optionally substituted by 1 to 4 alkyl groups and in which in each case two hydrogen atoms in the cyclopentyl part are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 2 to 4 carbon atoms if the two hydrogen atoms are on carbon atoms which are separated by a carbon atom, wherein the abovementioned rings can additionally be substituted by the radical $R_5$, which is as defined above, a cyclohexyl, cyclohexylalkyl, cycloheptyl or cycloheptylalkyl group which is optionally substituted by 1 to 4 alkyl groups and in which in each case two hydrogen atoms in the cycloalkyl part are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 1 to 4 carbon atoms if the two hydrogen atoms are on carbon atoms which are separated by a carbon atom, or contains 1 to 3 carbon atoms if the two hydrogen atoms are on carbon atoms which are separated by two carbon atoms, wherein the abovementioned rings can additionally be substituted by the radical $R_5$, which is as defined above, a 3-cyclohexen-1-yl or 3-cyclohexen-1-yl-alkyl group which is optionally substituted by 1 to 4 alkyl groups and in which two hydrogen atoms in the 2,5-position in the cyclohexenyl part are replaced by an n-$C_{1-3}$-alkylene bridge, a 3-quinuclidinyl, 4-quinuclidinyl, 2-quinuclidinyl-alkyl, 3-quinuclidinyl-alkyl, 4-quinuclidinyl-alkyl, azabicyclo[2.2.1]hept-4-yl, azabicyclo[2.2.1]hept-4-yl-alkyl or adamantyl group, or $R_{10}$ is a hydrogen atom or an alkyl group and $R_{11}$ is a hydroxyl, alkoxy or cyano group, wherein, unless mentioned otherwise, the aryl parts mentioned in the definition of the abovementioned mentioned radicals is to be understood as meaning a phenyl group which can be in each case be monosubstituted by $R_{12}$, mono-, di- or trisubstituted by $R_{13}$ or monosubstituted by $R_{12}$ and additionally mono- or disubstituted by $R_{13}$, wherein the substituents can be identical or different, and $R_{12}$ is a cyano, carboxyl, aminocarbonyl, alkylaminocarbonyl, dialkytaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylcarbonylamino, N-alkyl-alkylcarbonylamino, alkylamino, dialkylamino, hydroxy-$C_{2-4}$-alkylamino, N-alkyl(hydroxy-$C_{2-4}$-alkyl)amino, bis-(hydroxy-$C_{2-4}$-alkyl)amino, phenylalkylcarbonylamino, phenylcarbonylamino, alkylsulphonylamino, phenylalkylsulphonylamino, phenylsulphonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl, dialkylaminosulphonyl, ($R_8NR_7$)—CO—$NR_6$— or ($R_8NR_7$)—$SO_2$—$NR_6$— group, wherein $R_6$, $R_7$ and $R_8$ are as defined above, a 5- to 7-membered alkylenimino group which is optionally substituted by 1 to 4 alkyl groups or a hydroxyalkyl group, wherein, in the abovementioned 6- to 7-membered alkylenimino groups, in each case a methylene group in the 4-position can be replaced by an oxygen atom or an $R_9N$ group, wherein $R_9$ is as defined above, a 5- to 7-membered alkylenimino group which is optionally substituted by 1 to 4 alkyl groups or a hydroxyalkyl group, wherein in each case one or two methylene groups adjacent to the nitrogen atom are in each case replaced by a carbonyl group, and $R_{13}$ is an alkyl, hydroxyl or alkoxy group or a fluorine, chlorine, bromine or iodine atom, wherein two radicals $R_{13}$, if these are bonded to adjacent carbon atoms, can also be an alkylene group having 3 to 6 carbon atoms, a 1,3-butadiene-1,4-diylene group or a methylenedioxy group, and, unless mentioned otherwise, the abovementioned alkyl, alkylene and alkoxy parts in each case contain 1 to 4 carbon atoms, in particular those of the abovementioned compounds of the general formula I, with the proviso that, unless mentioned otherwise, every carbon atom in the abovementioned alkylene or cycloalkylene parts which is bonded to a nitrogen, oxygen or sulphur atom cannot be bonded to a further halogen, nitrogen, oxygen or sulphur atom.

Preferred compounds of the above general formula I are those in which $R_a$ is a hydrogen atom or an alkyl group, $R_b$ is a phenyl group which is substituted by the radicals $R_1$ to $R_3$, wherein $R_1$ is a hydrogen, fluorine, chlorine, bromine or iodine atom, a $C_{1-6}$-alkyl, hydroxyl or $C_{1-6}$-alkoxy group, a $C_{3-6}$-cycloalkyl or $C_{5-6}$-cycloalkoxy group, a $C_{2-5}$-alkenyl or $C_{3-5}$-alkenyloxy group, wherein the vinyl part cannot be linked to the oxygen atom, a $C_{2-5}$-alkynyl or $C_{3-5}$-alkynyloxy group, wherein the ethynyl part cannot be linked to the oxygen atom, an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphonyl, arylsulphenyl, arylsulphinyl, arylsulphonyl, aralkylsulphenyl, aralkylsulphinyl or aralkylsulphonyl group, a methyl or methoxy group which is substituted by 1 to 3 fluorine atoms, a $C_{2-4}$-alkyl or $C_{2-4}$-alkoxy group which is substituted by 1 to 5 fluorine atoms, a nitro, amino, alkylamino, dialkylamino, $C_{3-6}$-cycloalkylamino, N-alkyl-$C_{3-6}$-cycloalkylamino, arylamino, N-alkylarylamino, aralkylamino or N-alkyl-aralkylamino group, a 5- to 7-membered alkylenimino group, wherein in each case one or two methylene groups adjacent to the nitrogen atom can in each case be replaced by a carbonyl group or, in the abovementioned 6- to 7-membered alkylenimino groups, a methylene group in the 4-position can be replaced by an oxygen atom or by an imino or N-alkyl-imino group, an (alkylenimino)carbonyl or (alkylenimino)sulphonyl group having in each case 5 to 7 ring atoms in the alkylenimino part, wherein, in the abovementioned 6- to 7-membered alkylenimino parts, in each case a methylene group in the 4-position can be replaced by an oxygen atom or by an imino or N-alkyl-imino group, an alkylcarbonylamino, N-alkyl-alkylcarbonylamino, alkylsulphonylamino, N-alkyl-alkylsulphonylamino, arylcarbonylantion, N-alkyl-arylcarbonylamino, arylsulphonylamino, N-alkylarylsulphonylamino, aralkylcarbonylamino, N-alkylaralkylcarbonylamino, aralkylsulphonylamino, N-alkylaralkylsulphonylamino, trifluoromethylsulphonylamino, N-alkyl-trifluoromethylsulphonylamino, alkylcarbonyl, arylcarbonyl, aralkylcarbonyl, carboxyl, alkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkyl-aralkyl-aminocarbonyl, N-hydroxy-aminocarbonyl, N-hydroxy-alkyl-aminocarbonyl, N-alkoxy-aminocarbonyl, N-alkoxy-alkylaminocarbonyl, cyano, azido, N-cyano-amino or N-cyanoalkylamino group, a sulpho, aminosulphonyl, alkylaminosulphonyl, dialkylaminosulphonyl, arylaminosulphonyl, N-alkyl-arylaminosulphonyl, aralkylaminosulphonyl or N-alkyl-aralkylaminosulphonyl group, a phosphono, O-alkyl-phosphono, O,O'-dialkyl-phosphono or O,O'-diaralkyl-phosphono group, an alkyl or alkoxy group which is substituted by $R_4$, wherein
$R_4$ is a hydroxyl, alkoxy, aryloxy, amino, alkylamino, dialkylamino, alkylsulphenyl, alkylsulphinyl, alkylsulphonyl, arylsulphenyl, arylsulphinyl, arylsulphonyl, carboxyl, alkoxycarbonyl, aminocarbonyl, alkylaminocarbonyl, dialkylaminocarbonyl or cyano group or
an (alkylenimino)carbonyl group having in each case 5 to 7 ring atoms in the alkylenimino part, wherein, in the abovementioned 6- to 7-membered alkylenimino parts, in each case a methylene group in the 4-position can be replaced by an oxygen atom or by an imino or N-alkyl-imino group, $R_2$ is a hydrogen, fluorine, chlorine or bromine atom or an alkyl, trifluoromethyl, hydroxyl, alkoxy, amino, alkylamino, dialkylamino, alkylcarbonylamino, N-alkyl-alkylcarbonylamino, alkylsulphonylamino N-alkyl-alkylsulphonylamino, trifluoromethylsulphonylamino, N-alkyl-trifluoromethylsulphonylamino or cyano group and $R_3$ is a hydrogen, fluorine, chlorine or bromine atom or an alkyl, trifluoromethyl or alkoxy group, or $R_2$ together with $R_3$, if these are bonded to adjacent carbon atoms, is a methylenedioxy group which is optionally substituted by one or two alkyl groups, an n-$C_{3-6}$-alkylene group which is optionally substituted by one or two alkyl groups, or a 1,3-butadiene-1,4-diylene group which is optionally substituted by a fluorine, chlorine or bromine atom or by a hydroxyl, alkyl, alkoxy, trifluoromethyl or cyano group, or $R_a$ together with $R_1$, if $R_1$ is in the o-position relative to the nitrogen atom substituted by $R_a$, is an n-$C_{2-3}$-alkylene group, and $R_c$ is a hydrogen or chlorine atom, an alkyl, aryl, aralkyl, mercapto, alkylsulphenyl, alkylsulphinyl or alkylsulphonyl group, a hydroxyl, aryloxy or aralkoxy group, a $C_{1-6}$-alkoxy group, which can be substituted by an alkoxycarbonyl, cyano, carboxyl, aminocarbonyl, alkylaminocarbonyl or dialkylaminocarbonyl group, a $C_{2-6}$-alkoxy group substituted by a hydroxyl, alkoxy, hydroxy-$C_{2-4}$-alkylamino, amino, alkylamino, dialkylamino, alkylcarbonylamino, alkylsulphonylamino or alkoxycarbonylamino group, or by a 5- to 7-membered alkylenimino group which is optionally substituted by 1 to 2 alkyl groups, wherein, in the abovementioned 5- to 7-membered alkylenimino groups, in each case one or two methylene groups adjacent to the nitrogen atom can in each case be replaced by a carbonyl group, or in the abovementioned 6- to 7-membered alkylenimino groups, a methylene group in the 4-position can be replaced by an oxygen atom or by a carbonyl, imino, alkyl-imino, alkylcarbonyl-imino, alkoxycarbonyl-imino, alkylsulphonyl-imino, formyl-imino, dialkylaminocarbonyl-imino, aryl-imino or aralkyl-imino group, a $C_{3-6}$-alkoxy group substituted by two hydroxyl or alkoxy groups, an alkoxy group which is substituted by a $C_{3-7}$-cycloalkyl group wherein the cycloalkyl residue in each case can be substituted by one or two alkyl groups and wherein, in the abovementioned $C_{4-7}$-cycloalkyl residues, in each case a methylene group can be replaced by an oxygen atom, or by an imino, N-alkyl-imino, N-alkylcarbonyl-imino, N-alkoxycarbonyl-imino or N-aryl-imino group, a $C_{4-7}$-cycloalkoxy group which is optionally substituted by a hydroxyl, alkoxy, alkoxycarbonyl, cyano, carboxyl, aminocarbonyl, alkylaminocarbonyl, dialkylaminocarbonyl, hydroxy-$C_{2-4}$-alkylamino, amino, alkylamino, dialkylamino, alkylcarbonylamino, alkylsulphonylamino or alkoxycarbonylamino group, a $C_{5-7}$-cycloalkoxy group, wherein, in the abovementioned cyclopentyloxy group, in each case a methylene group in the 3-position, and in the abovementioned $C_{6-7}$-cycloalkoxy groups, in each case a methylene group in the 3- or 4-position is replaced by an oxygen atom or by an imino, alkyl-imino, alkylcarbonyl-imino, alkoxycarbonyl-imino, alkylsulphonylimino, aryl-imino or aralkyl-imino group, a $C_{3-6}$-alkenyloxy group, wherein the vinyl part cannot be linked to the oxygen atom, a $C_{3-6}$-alkynyloxy group, wherein the ethynyl part cannot be linked to the oxygen atom, a 4- to 8-membered alkylenimino group which is optionally substituted by 1 to 4 alkyl groups or an aryl group and can additionally be substituted by the radical $R_5$, wherein
$R_5$ is an aryl, aralkyl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl, 4-alkylpiperazinocarbonyl, cyano, hydroxyl, alkoxy, aryloxy, amino, alkylamino, dialkylamino, hydroxy-$C_{2-4}$-alkylamino, amino, N-alkyl-hydroxy-$C_{2-4}$-alkylamino, di-(hydroxy-$C_{2-4}$-alkyl)amino, formylamino, cyanoamino, alkylcarbonylamino, N-alkyl-alkylcarbonylamino, alkoxycarbonylamino, N-alkyl-alkoxycarbonyl-amino, alkylsulphonyl amino, N-alkyl-alkylsulphonylamino, aryl carbonylamino, N-alkyl-arylcarbonylamino, arylsulphonyl-amino, N-alkyl-arylsulphonylamino, carboxyalkyl, alkoxycarbonylalkyl, aminocarbonylalkyl, alkylaminocarbonylalkyl, dialkylaminocarbonylalkyl, pyrrolidinocarbonylalkyl, piperidinocarbonylalkyl, morpholinocarbonylalkyl, piperazinocarbonylalkyl, 4-alkyl-piperazinocarbonylalkyl, cyanoalkyl, hydroxyalkyl, alkoxyalkyl, aryloxyalkyl, aminoalkyl, alkylaminoalkyl, dialkylaminoalkyl, alkylcarbonylaminoalkyl, N-alkyl-alkylcarbonylaminoalkyl, alkylsulphonylaminoalkyl, N-alkyl-alkylsulphonylaminoalkyl, arylcarbonylaminoalkyl, N-alkyl-arylcarbonylaminoalkyl, arylsulphonylaminoalkyl, N-alkyl-arylsulphonylaminoalkyl, alkylsulphenyl, alkylsulphinyl, alkylsulphonyl, arylsulphenyl, arylsulphinyl, arylsulphonyl, alkylsulphenylalkyl, alkylsulphinylalkyl, alkylsulphonylalkyl, arylsulphenylalkyl, arylsulphinylalkyl, arylsulphonylalkyl, carboxyalkoxy, alkoxycarbonylalkoxy, aminocarbonylalkoxy, alkylaminocarbonylalkoxy, dialkylaminocarbonylalkoxy, pyrrolidinocarbonylalkoxy, piperidinocarbonylalkoxy, morpholinocarbonylalkoxy or an $(R_8NR_7)$—CO—$NR_6$— group, wherein, $R_6$, $R_7$ and $R_8$, which can be identical or different, are each a hydrogen atom or an alkyl group, or $R_6$ and $R_7$ together are an n-$C_{2-3}$-alkylene group and $R_8$ is a hydrogen atom or an alkyl group, a pyrrolidino, piperidino, morpholino, piperazino, 4-alkylpiperazino or 4-alkoxycarbonylpiperazino group, optionally substituted by one or two alkyl groups or a hydroxymethyl group, wherein, in the heterocyclic residue of the abovementioned groups, in each case one or two of the methylene groups adjacent to the nitrogen atoms can be replaced by a carbonyl group, or $R_c$ is a 6- to 8-membered alkylenimino group which is optionally substituted by 1 to 4 alkyl groups or by an aryl group and can additionally be substituted by the radical $R_5$, wherein, in the abovementioned alkylenimino groups, in each case a methylene group in the 4-position is replaced by an oxygen or sulphur atom or by a carbonyl, sulphinyl, sulphonyl, N-oxido-N-alkylimino or $R_9N$ group, wherein $R_9$ is a hydrogen atom or an alkyl, hydroxy-$C_{2-4}$-alkyl, alkoxy-$C_{2-4}$-alkyl, hydroxy-$C_{2-4}$-alkoxy-$C_{2-4}$-alkyl, aminocarbonylalkyl, alkylaminocarbonylalkyl, dialkylaminocarbonylalkyl, amino-$C_{2-4}$-alkyl, alkylamino-$C_{2-4}$-alkyl, dialkylamino-$C_{2-4}$-alkyl, aryl, aralkyl, formyl, alkylcarbonyl, alkylsulphonyl, arylcarbonyl, arylsulphonyl, aralkylcarbonyl, aralkylsulphonyl, alkoxycarbonyl, cyano, aminocarbonyl, alkylaminocarbonyl or dialkylaminocarbonyl group, or $R_c$ is a 1-pyrrolidinyl group which is optionally substituted by 1 or 2 alkyl groups and in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, a 1-piperidinyl or 1-azacyclohept-1-yl group which is optionally substituted by 1 or 2 alkyl groups and in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, or contains 1 or 2 carbon atoms if the two hydrogen atoms are on carbon atoms which are separated by two atoms, a 1-pyrrolidinyl group in which two hydrogen atoms in the 3-position are replaced by a —O—$CH_2CH_2$—O— or —O—$CH_2CH_2CH_2$—O— group, a 1-piperidinyl or 1-azacyclohept-1-yl group in which two hydrogen atoms in the 3-position or in the 4-position are replaced by a —O—$CH_2CH_2$—O— or —O—$CH_2CH_2CH_2$—O— group, a 2-isoindolinyl, 1,2,3,4-tetrahydro-isoquinolin-2-yl or 2,3,4,5-tetrahydro-1H-3-benzazepin-3-yl group, wherein the benzo part of the abovementioned groups can in each case be substituted by a fluorine, chlorine, bromine or iodine atom, by a trifluoromethyl group or by one or two alkyl or alkoxy groups, or a $(R_{10}NR_{11})$— group, in which $R_{10}$ is a hydrogen atom or a $C_{1-8}$-alkyl group, which can be substituted from position 2 by a hydroxyl or alkoxy group, $R_{11}$ is a hydrogen atom, a $C_{1-10}$-alkyl group, which can be substituted by an aryl, $C_{3-7}$-cycloalkyl, hydroxyl, alkoxy, aryloxy, carboxyl, alkoxycarbonyl, aminocarbonyl, alkylaminocarbonyl, dialkylaminocarbonyl, hydroxy-$C_{2-4}$-alkylaminocarbonyl, cyano, formylamino, amino, alkylamino or dialkylamino group, by a pyrrolidinocarbonyl, piperidinocarbonyl, morpholinocarbonyl, piperazinocarbonyl or 4-alkyl-piperazinocarbonyl group, by a 5- to 7-membered alkylenimino group which is optionally substituted by 1 or 2 alkyl groups, Wherein, in the abovementioned 6- or 7-membered alkylenimino residues, in each case a methylene group in the 4-position can be replaced by an oxygen or sulphur atom or by a sulphinyl, sulphonyl or $R_9N$ group, wherein $R_9$ is as defined above, by a pyrrolidino, piperidino, piperazino or 4-alkylpiperazino group, wherein in each case one or two of the methylene groups adjacent to the nitrogen atoms are replaced by a carbonyl group, by an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino or N-alkyl-alkoxycarbonylamino group, by an $(R_8NR_7)$—CO—$NR_6$— group, wherein $R_6$ to $R_8$ are as defined above, by an alkylsulphenyl, alkylsulphinyl, alkylsulphonyl, arylsulphenyl, arylsulphinyl, arylsulphonyl, aralkylsulphenyl, aralkylsulphinyl or aralkylsulphonyl group or by a $C_{5-7}$-cycloalkyl group in which a methylene group is replaced by an oxygen atom or by an imino or alkylimino group, a $C_{2-4}$-alkyl group substituted by a chlorine atom or by one to three fluorine atoms, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a $C_{3-10}$-alkyl group which is substituted by 2 to 5 hydroxyl groups, a $C_{2-6}$-alkyl group which is substituted by a hydroxyl and additionally by an aryl group and which can optionally additionally be substituted by a hydroxyl or alkoxy group, a $C_{3-6}$-alkyl group which is substituted by a hydroxyl and additionally by an amino, alkylamino or dialkylamino group, an alkenyl or alkynyl group which has in each case 3 to 6 carbon atoms and is optionally substituted by an aryl group, wherein the vinyl or ethynyl part cannot be linked to the nitrogen atom, a $C_{2-4}$-alkyl group, which is substituted by a $C_{2-4}$-alkoxy group, which is substituted in the ω-position by a hydroxyl or alkoxy group, an aryl group, a cyclopropyl group, which can be substituted by 1 or 2 alkyl groups or by an aryl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group, a $C_{4-7}$-cycloalkyl group which is optionally substituted by 1 or 2 alkyl groups and can additionally be substituted by $R_5$, wherein $R_5$ is as defined above, a $C_{5-7}$-cycloalkyl group which is optionally substituted by 1 or 2 alkyl groups and is additionally substituted by an N,N-dialkyl-N-oxido-amino group, a $C_{5-7}$-cycloalkenyl group which is optionally substituted by 1 or 2 alkyl groups, wherein the vinyl part cannot be linked to the nitrogen atom of the $(R_{11}NR_{10})$— group, a $C_{5-7}$-cycloalkyl group which is optionally substituted by 1 or 2 alkyl groups, wherein, in the cycloalkyl part, in each case a methylene group is replaced by an oxygen or sulphur atom or by a sulphinyl, sulphonyl, N-alkyl-N-oxido-imino or $R_9N$ group, wherein $R_9$ is as defined above, a $C_{5-7}$-cycloalkyl group which is optionally substituted by 1 to 4 alkyl groups and in which in each case a methylene group is replaced by a carbonyl group, a $C_{4-7}$-cycloalkylmethyl group which is optionally substituted by 1 or 2 alkyl groups and is additionally substituted in the cycloalkyl part by $R_5$, wherein $R_5$ is defined as mentioned above, a cyclopentyl or cyclopentylalkyl group which is optionally substituted by 1 to 4 alkyl groups and in which in each case two hydrogen atoms in the cyclopentyl part are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by a carbon atom, a cyclohexyl, cyclohexylalkyl, cycloheptyl or cycloheptylalkyl group which is optionally substituted by 1 to 4 alkyl groups and in which in each case two hydrogen atoms in the cycloalkyl part are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by a carbon atom, or contains 1 or 2 carbon atoms if the two hydrogen atoms are on carbon atoms which are separated by two carbon atoms, a 5-norbornen-2-yl or 5-norbornen-2-yl-alkyl group which is optionally substituted by 1 to 4 alkyl groups, a 3-quinuclidinyl, 4-quinuclidinyl, 3-quinuclidinyl-alkyl, 4-quinuclidinyl-alkyl, azabicyclo[2.2.1]hept-4-yl, azabicyclo[2.2.1]hept-4-yl-alkyl or adamantyl group, or $R_{10}$ is a hydrogen atom or an alkyl group and $R_{11}$ is a hydroxyl or alkoxy group, their tautomers, their stereoisomers and their salts, wherein, unless mentioned otherwise, the aryl parts mentioned in the definition of the abovementioned radicals are to be understood as meaning a phenyl group, which can in each case be monosubstituted by $R_{12}$, mono-, di- or trisubstituted by $R_{13}$ or monosubstituted by $R_{12}$ and additionally mono- or disubstituted by $R_{13}$, wherein the substituents can be identical or different, and $R_{12}$ is a cyano, carboxyl, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylamino, hydroxy-$C_{2-4}$-alkylamino, N-alkyl-hydroxy-$C_{2-4}$-alkylamino, di(hydroxy-$C_{2-4}$-alkyl) amino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkylphenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl or dialkylaminosulphonyl group, a 5- to 7-membered alkylenimino group which is optionally substituted by 1 to 2 alkyl groups or a hydroxyalkyl group, wherein, in the abovementioned 6- to 7-membered alkylenimino groups, in each case a methylene group in the 4-position can be replaced by an oxygen atom or an $R_9N$ group, wherein a 5- to 7-membered alkylenimino group which is optionally substituted by 1 to 2 alkyl groups or a hydroxyalkyl group, wherein in each case one or two methylene groups adjacent to the nitrogen atom are replaced by in each case a carbonyl group, an $(R_8NR_7)$—CO—$NR_6$— group, wherein $R_6$ to $R_8$ are defined as mentioned above, $R_{13}$ is an alkyl, hydroxyl or alkoxy group or a fluorine, chlorine, bromine or iodine atom, wherein two radicals $R_{13}$, if these are bonded to adjacent carbon atoms, can also be an alkylene group having 3 to 6 carbon atoms, a 1,3-butadiene-1,4-diylene group or a methylenedioxy group, and, unless mentioned otherwise, the abovementioned alkyl, alkylene and alkoxy parts in each case contain 1 to 4 carbon atoms and, unless mentioned otherwise, each carbon atom in the abovementioned alkylene or cycloalkylene parts which is bonded to a nitrogen, oxygen or sulphur atom cannot be bonded to a further halogen, nitrogen, oxygen or sulphur atom.

Particularly preferred compounds of the general formula I are those in which $R_a$ is a hydrogen atom or an alkyl group, $R_b$ is a phenyl group which is substituted by the radicals $R_1$ to $R_3$, wherein $R_1$ is a hydrogen, fluorine, chlorine, bromine or iodine atom, an alkyl, hydroxyl, alkoxy, $C_{3-6}$-cycloalkyl or $C_{5-6}$-cycloalkoxy group, an ethoxy group which is substituted in the 2-position by a hydroxyl, alkoxy or phenoxy group, a $C_{2-5}$-alkenyl or $C_{3-5}$-alkenyloxy group, wherein the vinyl part cannot be linked to the oxygen atom, a $C_{2-5}$-alkynyl or $C_{3-5}$-alkynyloxy group, wherein the ethynyl part cannot be linked to the oxygen atom, a phenyl, phenoxy, phenylalkyl, phenylalkoxy, alkoxyalkyl, phenoxyalkyl, carboxyalkyl, alkoxycarbonylalkyl, aminocarbonylalkyl, alkylaminocarbonylalkyl, dialkylaminocarbonylalkyl, cyanoalkyl, alkylsulphenyl, alkylsulphinyl, alkylsulphonyl, alkylsulphonyloxy, trifluoromethylsulphenyl, trifluoromethylsulphonyl, nitro, amino, alkylamino, dialkylamino, pyrrolidino, piperidino, morpholino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino, alkylcarbonyl, carboxyl, alkoxycarbonyl, aminocarbonyl, alkylaminocarbonyl, dialkylaminocarbonyl, pyrrolidinocarbonyl, piperidinocarbonyl, morpholinocarbonyl or cyano group, a methyl or methoxy group which is substituted by 1 to 3 fluorine atoms, an ethyl or ethoxy group which is substituted by 1 to 5 fluorine atoms, $R_2$ is a hydrogen, fluorine, chlorine or bromine atom or an alkyl, trifluoromethyl, amino, alkylamino, dialkylamino, alkylcarbonylamino, alkylsulphonylamino, trifluoromethylsulphonylamino, hydroxyl or alkoxy group, $R_3$ is a hydrogen, fluorine, chlorine or bromine atom or an alkyl group, or $R_2$ together with $R_3$, if these are bonded to adjacent carbon atoms, is a methylenedioxy or n-$C_{3-6}$-alkylene group or a 1,3-butadiene-1,4-diylene group which is optionally substituted by a fluorine, chlorine or bromine atom or by an alkyl, alkoxy or trifluoromethyl group and $R_c$ is a hydrogen or chlorine atom, an alkyl, phenyl, mercapto, alkylsulphenyl, alkylsulphinyl or alkylsulphonyl group, a hydroxyl, phenoxy or phenyl-$C_{1-2}$-alkoxy group, an alkoxy group, a $C_{2-4}$-alkoxy group, which is substituted by a hydroxyl, alkoxy, (2-hydroxyethyl)amino, dialkylamino, morpholino, 1-pyrrolidinyl, 1-piperidinyl, 4-methyl-1-piperazinyl, 4-acetyl-1-piperazinyl, 4-methylsulphonyl-1-piperazinyl, 4-methoxycarbonyl-1-piperazinyl, 4-formyl-1-piperazinyl or 4-dimethylaminocarbonyl-1-piperazinyl group, a $C_{3-4}$-alkoxy group, which is substituted by two hydroxyl groups, a $C_{1-2}$-alkoxy group, which is substituted by a $C_{3-7}$-cycloalkyl group which is optionally substituted by one or two methyl groups, wherein, in the abovementioned $C_{4-6}$-cycloalkyl groups, in each case a methylene group can be replaced by an oxygen atom, a $C_{4-6}$-cycloalkoxy group which is optionally substituted by a hydroxyl, diahydroxyl, dialkylamino, alkoxy, carboxyl, alkoxycarbonyl, aminocarbonyl, alkylaminocarbonyl, dialkylaminocarbonyl, alkylcarbonylamino, alkylsulphonylamino or alkoxycarbonylamino group, a cyclopentyloxy group in which the methylene group in the 3-position is replaced by an oxygen atom or by an alkylimino group, a cyclohexyloxy group in which the methylene group in the 3- or 4-position is replaced by an oxygen atom or by an alkylimino, alkylcarbonyl-imino, alkoxycarbonyl-imino or alkylsulphonyl-imino group, an allyloxy or propargyloxy group which is optionally substituted by one or two methyl groups, a 1-azetidinyl group, a 1-pyrrolidinyl group, which can be substituted by 1 to 2 alkyl groups, by a phenyl, carboxyl, hydroxyalkyl, aminoalkyl, alkylaminoalkyl, dialkylaminoalkyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group or in the 3-position also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino, N-alkyl-dialkylaminocarbonylamino or cyano group, a 1-pyrrolidinyl group in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, a 1-piperidinyl group, which can be substituted by 1 to 4 alkyl groups, by a phenyl, hydroxyalkyl, aminoalkyl, alkylaminoalkyl, dialkylaminoalkyl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group or in the 3- or 4-position also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group, a 1-piperidinyl group, which is substituted by 1 to 2 alkyl groups or a phenyl group and additionally by a hydroxyl group, a 1-piperidinyl group in which two hydrogen atoms in the 3-position or in the 4-position are replaced by a —O—$CH_2CH_2$—O— or —O—$CH_2CH_2CH_2$—O— group, a 1-piperidinyl group in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, or contains 1 or 2 carbon atoms if the two hydrogen atoms are on carbon atoms which are separated by two atoms, a 1-piperidinyl group which is optionally substituted by 1 or 2 alkyl groups and in which the methylene group in the 4-position is replaced by an oxygen or sulphur atom or by a carbonyl, sulphinyl, sulphonyl, imino, alkyl-imino, hydroxy-$C_{2-4}$-alkyl-imino, alkoxy-$C_{2-4}$-alkyl-imino, aminocarbonylalkylimino, alkylaminocarbonylalkyl-imino, dialkylaminocarbonylalkyl-imino, amino-$C_{2-4}$-alkyl-imino, alkylamino-$C_{2-4}$-alkyl-imino, dialkylamino-$C_{2-4}$-alkyl-imino, hydroxy-$C_{2-4}$-alkoxy-$C_{2-4}$-alkyl-imino, phenyl-imino, phenylalkyl-imino, alkylcarbonyl-imino, alkylsulphonyl-imino, phenylcarbonyl-imino, phenylsulphonyl-imino or N-oxido-N-alkyl-imino group, a 1-azacyclohept-1-yl group which is optionally substituted by 1 or 2 alkyl groups and in which in each case the methylene group in the 4-position can be replaced by an oxygen atom or by an imino, N-alkyl-imino, N-phenyl-imino, N-phenylalkylimino, N-alkylcarbonyl-imino, N-alkylsulphonyl-imino, N-phenylcarbonyl-imino or N-phenylsulphonyl-imino group or two hydrogen atoms in the 3,6-position can be replaced by a —$CH_2CH_2$— group, a 2-isoindolinyl, 1,2,3,4-tetrahydro-isoquinolin-2-yl or 2,3,4,5-tetrahydro-1H-3-benzazepin-3-yl group, which can in each case be substituted in the benzo part by a fluorine, chlorine or bromine atom or by an alkyl, trifluoromethyl or alkoxy group, or an $(R_{10}NR_{11})$— group, in which $R_{10}$ is a hydrogen atom or a $C_{1-6}$-alkyl group, which can be substituted by a hydroxyl or alkoxy group from position 2, and $R_{11}$ is a hydrogen atom, a $C_{1-8}$-alkyl group, which can be substituted by a phenyl, $C_{3-6}$-cycloalkyl, hydroxyl, alkoxy, cyano, carboxyl, alkoxycarbonyl, aminocarbonyl, alkylaminocarbonyl, dialkylaminocarbonyl, (2-hydroxyethyl) aminocarbonyl, pyrrolidinocarbonyl, piperidinocarbonyl, morpholinocarbonyl, 1-piperazinylcarbonyl, 4-alkyl-1-piperazinylcarbonyl, amino, formylamino, alkylamino, dialkylamino, alkylcarbonylamino, N-alkyl-alkylcarbonylamino, alkoxycarbonylamino, N-alkyl-alkoxycarbonyl-amino, alkylsulphonylamino, N-alkyl-alkylsulphonylamino, phenylcarbonylamino, N-alkyl-phenylcarbonylamino, phenyl-sulphonylamino, N-alkylphenylsulphonylamino, alkylsulphenyl, alkylsulphinyl, alkylsulphonyl, 1-pyrrolidinyl, 2-oxo-1-pyrrolidinyl, 1-piperidinyl, 2-oxo-1-piperidinyl, morpholino, 1-piperazinyl, 4-alkyl-1-piperazinyl, 4-alkylcarbonyl-1-piperazinyl, 4-alkylsulphonyl-1-piperazinyl, 4-alkoxycarbonyl-1-piperazinyl, 4-cyano-1-piperazinyl, 4-formyl-1-piperazinyl, 4-aminocarbonyl-1-piperazinyl, 4-alkylaminocarbonyl-1-piperazinyl or 4-dialkylaminocarbonyl-1-piperazinyl or a $(R_8NR_7)$—CO—$NR_6$— group, wherein $R_6$ and $R_7$ together are an n-$C_{2-3}$-alkylene bridge and $R_8$ is a hydrogen atom or an alkyl group, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a 2,2,2-trifluoroethyl group, a $C_{3-10}$-alkyl group which is substituted by 2 to 5 hydroxyl groups, a $C_{3-5}$-alkyl group which is substituted by a hydroxyl and additionally by an amino group, a $C_{2-4}$-alkyl group which is substituted by a phenyl group and additionally by a hydroxyl group and which can optionally additionally be substituted by a hydroxyl or alkoxy group, an alkenyl or alkynyl group which has in each case 3 to 6 carbon atoms and is optionally substituted by a phenyl group, wherein the vinyl or ethynyl part cannot be linked to the nitrogen atom, a $C_{2-4}$-alkyl group which is substituted by a $C_{2-4}$-alkoxy group which is substituted in the ω-position by a hydroxyl or alkoxy group, a phenyl group, a phenyl group which is substituted by an alkylcarbonylamino, N-alkyl-alkylcarbonylamino, (2-hydroxyethyl)amino, di-(2-hydroxyethyl)amino, N-alkyl-(2-hydroxyethyl)amino, amino, alkylamino or dialkylamino group or by an $(R_8NR_7)$—CO—$NR_6$— group wherein $R_6$ to $R_8$ are defined as mentioned above, a phenyl group, which is substituted by a pyrrolidino, piperidino, 2-oxo-pyrrolidino, 2-oxo-piperidino, morpholino, 1-piperazinyl or 4-alkyl-1-piperazinyl group, wherein the abovementioned heterocyclic parts can be substituted on the carbon skeleton in each case by 1 or 2 alkyl groups or by a hydroxyalkyl group, a $C_{3-7}$-cycloalkyl group which can be substituted by 1 or 2 alkyl groups or by a phenyl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group, a $C_{5-7}$-cycloalkyl group which is optionally substituted by 1 or 2 methyl groups and is substituted by a hydroxymethyl, cyano, hydroxyl, alkoxy, amino, alkylamino, dialkylamino, 2-hydroxyethylamino, di-(2-hydroxyethyl)amino, N-alkyl-2-hydroxyethylamino, N,N-dialkyl-N-oxido-amino, alkoxycarbonylamino, N-alkyl-alkoxycarbonylamino, alkylcarbonylamino, N-alkyl-alkylcarbonylamino, alkylsulphonylamino, N-alkyl-alkylsulphonylamino, phenylcarbonylamino, N-alkyl-phenylcarbonyl-amino, phenylsulphonylamino, N-alkylphenylsulphonylamino or by an $(R_8NR_7)$—CO—$NR_6$— group, wherein $R_6$ to $R_8$ are defined as mentioned above, a $C_{5-7}$-cycloalkyl group which is optionally substituted by 1 or 2 methyl groups and is substituted by a pyrrolidino, piperidino, 2-oxo-pyrrolidino, 2-oxo-piperidino, morpholino, 1-piperazinyl, 4-alkyl-1-piperazinyl or 4-alkylcarbonyl-1-piperazinyl group, wherein the abovementioned heterocyclic parts can in each case be substituted on the carbon skeleton by 1 or 2 alkyl groups or by a hydroxymethyl group, a $C_{5-7}$-cycloalkenyl group which is optionally substituted by 1 or 2 alkyl groups, wherein the vinyl part cannot be bonded to the nitrogen atom of the $(R_{11}NR_{10})$— group, a tetrahydrofurfuryl group, a cyclopentyl group in which the methylene group in the 3-position is replaced by an oxygen atom or an imino, alkylimino, alkylcarbonylimino, formylimino, aminocarbonylimino, alkylaminocarbonylimino, alkoxycarbonylimino, alkylsulphonylimino, dialkylaminocarbonylimino or cyanoimino group, a cyclohexyl group in which the methylene group in the 3-position is replaced by an imino, alkyl-imino, alkylcarbonyl-imino, alkoxycarbonyl-imino or alkylsulphonyl-imino group, a cyclohexyl group in which the methylene group in the 4-position is replaced by an oxygen atom or an imino, N-alkyl-imino, N-phenyl-imino, N-phenylalkyl-imino, N-formyl-imino, N-alkylcarbonyl-imino, N-phenylcarbonyl-imino, N-alkoxy-carbonyl-imino, N-cyano-imino, N-aminocarbonyl-imino, N-alkylamino-carbonyl-imino, N,N-dialkylaminocarbonyl-imino, N-alkyl-N-oxido-imino, N-alkylsulphonyl-imino or N-phenylsulphonylimino group, a cyclohexyl group in which a methylene group is replaced by a carbonyl group, a cyclopentyl or cyclohexyl group which is optionally substituted by 1 to 2 methyl groups and is substituted by a carboxyalkoxy, alkoxycarbonylalkoxy, aminocarbonylalkoxy, alkylaminocarbonylalkoxy, dialkylaminocarbonylalkoxy, pyrrolidinocarbonylalkoxy, piperidinocarbonylalkoxy, morpholino-carbonylalkoxy, carboxyalkyl, alkoxycarbonylalkyl, aminocarbonylalkyl, alkylaminocarbonylalkyl, dialkylaminocarbonylalkyl, pyrrolidinocarbonylalkyl, piperidinocarbonylalkyl or morpholinocarbonylalkyl group, a cyclohexylmethyl group, wherein the cyclohexyl part is substituted by a carboxyl, aminocarbonyl, alkylaminocarbonyl, dialkylaminocarbonyl, pyrrolidinocarbonyl, piperidinocarbonyl, morpholinocarbonyl, alkoxycarbonyl or hydroxymethyl group, a cyclohexyl or cyclohexylmethyl group which is optionally substituted by 1 to 3 methyl groups and in which in each case two hydrogen atoms in the cyclohexyl part are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by a carbon atom, or contains 1 or 2 carbon atoms if the two hydrogen atoms are on carbon atoms which are separated by two carbon atoms, a 5-norbornen-2-yl or 5-norbornen-2-yl-methyl group which is optionally substituted by 1 to 3 methyl groups, a 3-quinuclidinyl, 4-quinuclidinyl or adamantyl group, or $R_{10}$ is a hydrogen atom or an alkyl group and $R_{11}$ is a hydroxyl or alkoxy group, their tautomers, their stereoisomers and their salts, wherein the abovementioned phenyl radicals in each case can be substituted by a fluorine, chlorine or bromine atom or by a nitro, alkyl, alkoxy, trifluoromethyl or hydroxyl group and, unless mentioned otherwise, the abovementioned alkyl, alkylene and alkoxy parts in each case contain 1 to 4 carbon atoms and, unless mentioned otherwise, each carbon atom in the abovementioned alkylene or cycloalkylene parts which is bonded to a nitrogen, oxygen or sulphur atom cannot be bonded to a further halogen, nitrogen, oxygen or sulphur atom.

Especially preferred compounds of the general formula I are those in which $R_a$ is a hydrogen atom or a methyl group, $R_b$ is a 2-naphthyl, 1,2,3,4-tetrahydro-6-naphthyl or 5-indanyl group, or a phenyl group which is substituted by the radicals $R_1$ to $R_3$, wherein $R_1$ is a hydrogen, fluorine, chlorine, bromine or iodine atom, a $C_{1-4}$-alkyl, $C_{1-4}$-alkoxy, $C_{3-6}$-cycloalkyl, $C_{5-6}$-cycloalkoxy, cyano, methoxycarbonyl, ethoxycarbonyl, ethynyl or nitro group, a methyl or methoxy group which is substituted by 1 to 3 fluorine atoms, an ethyl or ethoxy group which is substituted by 1 to 5 fluorine atoms, $R_2$ is a hydrogen, fluorine or chlorine atom or a methyl, hydroxyl, methoxy, amino, $C_{1-2}$-alkylamino, di-$C_{1-2}$-alkylamino, $C_{1-2}$-alkylcarbonylamino, $C_{1-2}$-alkylsulphonylamino, trifluoromethylsulphonylamino or trifluoromethyl group, $R_3$ is a hydrogen, fluorine, chlorine or bromine atom or a methyl group and $R_c$ is a hydrogen atom or a methyl, phenyl, 4-methoxyphenyl, methylsulphenyl, methylsulphinyl or methylsulphonyl group, a hydroxyl group, a $C_{1-4}$-alkoxy group, an ethoxy group which is substituted in the 2-position by a hydroxyl, methoxy, morpholino or (2-hydroxyethyl)amino group, a 2-propyloxy group which is substituted in the 1-position by a methoxy or dimethylamino group, a methoxy group which is substituted by a 2-tetrahydrofuryl, 2-tetrahydropyranyl or 3-methyl-3-oxetanyl group, a cyclobutyloxy group, a cyclopentyloxy group which is optionally substituted in the 3-position by a hydroxyl group, a cyclopentyloxy group in which the methylene group in the 3-position is replaced by an oxygen atom or by a methyl-imino group, a cyclohexyloxy group which can be substituted in the 2-, 3- or 4-position by a hydroxyl group or in the 4-position also by a di-($C_{1-2}$-alkyl)amino, methoxy, carboxyl, methoxycarbonyl, dimethylaminocarbonyl, methylaminocarbonyl, aminocarbonyl, acetylamino, methylsulphonylamino, methoxycarbonylamino or tert-butyloxycarbonylamino group, a cyclohexyloxy group in which the methylene group in the 3-position is replaced by a methyl-imino group or the methylene group in the 4-position is replaced by an oxygen atom or by a methyl-imino, acetyl-imino, tertbutyloxycarbonyl-imino, methoxycarbonyl-imino or methylsulphonyl-imino group, an allyloxy group, a 1-azetidinyl group, a 1-pyrrolidinyl group which can be substituted by 1 or 2 methyl groups, by a carboxyl, methoxycarbonyl, ethoxycarbonyl, aminocarbonyl, $C_{1-2}$-alkylaminocarbonyl, or di-($C_{1-2}$)-alkylamino-carbonyl group or in the 3-position by an amino, $C_{1-2}$-alkylamino, di-($C_{1-2}$-alkyl)amino, $C_{1-2}$-alkoxycarbonylamino, $C_{1-2}$-alkylcarbonylamino, $C_{1-2}$-alkylsulphonylamino, cyanoamino, formylamino or dimethylaminocarbonylamino group, a 1-pyrrolidinyl group in which two hydrogen atoms in the 3-position are replaced by an n-$C_{4-5}$-alkylene bridge, a 1-piperidinyl group which can be substituted by 1 to 4 methyl groups, by a phenyl, hydroxy-$C_{1-2}$-alkyl, carboxyl, $C_{1-2}$-alkoxycarbonyl, aminocarbonyl, $C_{1-2}$-alkylaminocarbonyl, di-($C_{1-2}$)-alkylaminocarbonyl, pyrrolidinocarbonyl or morpholinocarbonyl group or in the 3- or 4-position by a hydroxyl, $C_{1-2}$-alkoxy, amino, $C_{1-2}$-alkylamino, di-($C_{1-2}$)alkylamino, $C_{1-2}$-alkylcarbonylamino, $C_{1-2}$-alkoxycarbonylamino, formylamino, cyanoamino, di-($C_{1-2}$-alkyl)aminocarbonylamino, $C_{1-2}$-alkylsulphonylamino or cyano group, a 1-piperidinyl group in which two hydrogen atoms in the 3-position or in the 4-position are replaced by an n-$C_{4-5}$-alkylene bridge or by an —O—$CH_2CH_2$—O— bridge, a 1-piperidinyl group which is substituted by 1 or 2 methyl groups or a phenyl group and additionally in the 3- or 4-position by a hydroxyl group, a 1-piperidinyl group in which two hydrogen atoms in the 2,5-position are replaced by a —CH$_2$— or —CH$_2$CH$_2$— bridge, a 1-piperidinyl group which is optionally substituted by 1 to 2 methyl groups and in which the methylene group in the 4-position is replaced by an oxygen or sulphur atom or by a carbonyl, sulphinyl, sulphonyl, imino, C$_{1-2}$-alkyl-imino, (2-hydroxyethyl)-imino, 2-(2-hydroxyethoxy)ethyl-imino, (2-aminoethyl)-imino, C$_{1-3}$-alkylaminocarbonylmethyl-imino, N-oxido-N-C$_{1-2}$-alkylimino, phenyl-imino, benzyl-imino, acetylimino or methanesulphonyl-imino group, a 1-azacyclohept-1-yl group in which two hydrogen atoms in the 3,6-position can be replaced by a —CH$_2$CH$_2$— group, a 1,2,3,4-tetrahydro-isoquinolin-2-yl or 2,3,4,5-tetrahydro-1H-3-benzazepin-3-yl group or an (R$_{10}$NR$_{11}$)— group in which R$_{10}$ is a hydrogen atom, a C$_{1-4}$-alkyl group or a 2-hydroxyethyl group and R$_{11}$ is a hydrogen atom, a C$_{1-6}$-alkyl, C$_{3-6}$-cycloalkyl-methyl or phenyl-C$_{1-3}$-alkyl group, a C$_{3-6}$-cycloalkyl, allyl or propargyl group which optionally substituted by 1 or 2 methyl groups, a phenyl group which can be substituted by a hydroxyl or methyl group or in the 4-position by an N-C$_{1-2}$-alkyl-C$_{1-2}$-alkylcarbonyl-amino, N-C$_{1-2}$-alkyl-(2-hydroxyethyl)amino, di-(2-hydroxyethyl)amino, 1-pyrrolidinyl, 2-oxo-1-pyrrolidinyl, 2-hydroxymethyl-1-pyrrolidinyl, 2-oxo-1-imidazolidinyl, 3-methyl-2-oxo-1-imidazolidinyl or morpholino group a methyl group which is substituted by a carboxyl, C$_{1-2}$-alkoxycarbonyl, aminocarbonyl, C$_{1-2}$-alkylaminocarbonyl, di-C$_{1-2}$-alkylaminocarbonyl, pyrrolidinocarbonyl, piperidinocarbonyl or morpholinocarbonyl group, an ethyl group which is optionally substituted by a methyl group and is substituted in the 2-position by a hydroxyl, C$_{1-2}$-alkoxy, amino, C$_{1-2}$-alkylamino, di-C$_{1-2}$-alkylamino, acetylamino, 1-pyrrolidinyl, morpholino, 1-piperazinyl, 4-methyl-1-piperazinyl, 4-acetyl-1-piperazinyl, 4-aminocarbonyl-1-piperazinyl, 4-dimethylaminocarbonyl-1-piperazinyl, 4-methylaminocarbonyl-1-piperazinyl, 4-methylsulphonyl-1-piperazinyl, 4-methoxycarbonyl-1-piperazinyl or 4-cyano-1-piperazinyl group, a 2-hydroxyethyl group which is substituted in the ethyl part by a phenyl, 3-hydroxyphenyl, 4-hydroxyphenyl, 4-nitrophenyl or benzyl group, wherein the ethyl part of the abovementioned groups can additionally be substituted by a methyl, hydroxymethyl or methoxymethyl group, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a 2,2,2-trifluoroethyl group, a propyl group which is substituted in the 3-position by a hydroxyl, cyano, carboxyl, aminocarbonyl, methylaminocarbonyl, dimethylaminocarbonyl, formylamino, methoxycarbonylamino, morpholino or 2-oxo-1-pyrrolidinyl group, a butyl group which is substituted in the 4-position by a hydroxyl group, a 3-butyl group which is substituted in the 1-position by a hydroxyl group and additionally in the 3-position by a methyl group, a 2-butyl group which is substituted in the 1-position by a hydroxyl group and additionally in the 3-position by a methyl group, a 4-pentyl group which is substituted in the 1-position by a hydroxyl group and additionally in the 4-position by a methyl group, a 2,3-dihydroxypropyl, 3-amino-2-hydroxypropyl, tris-(3-hydroxypropyl)methyl, 1,3-dihydroxy-2-propyl, 1,3-didhydroxy-2-methyl-2-propyl or tris-(hydroxymethyl)methyl group, a 2-propyl group which is substituted in the 2-position by a hydroxymethyl, C$_{1-2}$-alkoxymethyl, carboxyl, C$_{1-2}$-alkoxycarbonyl, aminocarbonyl, N-C$_{1-2}$-alkylaminocarbonyl, N,N-di-C$_{1-2}$-alkylaminocarbonyl, pyrrolidinocarbonyl, morpholinocarbonyl or (2-hydroxyethyl)aminocarbonyl group, a 4-tetrahydropyranyl, tetrahydrofurfuryl, 1-deoxy-1-D-sorbityl or 2-(2-hydroxyethyloxy)ethyl group, a cyclopentyl group which is substituted in the 2- or 3-position by a hydroxyl group or in the 1-position by a hydroxymethyl group, a cyclohexyl group which is substituted in the 2-, 3- or 4-position by a hydroxymethyl, hydroxy, C$_{1-2}$-alkoxy, (C$_{1-4}$-alkoxy)-carbonylamino, amino, C$_{1-2}$-alkylamino, di-C$_{1-2}$-alkylamino, carboxyl, C$_{1-2}$-alkoxycarbonyl, aminocarbonyl, C$_{1-2}$-alkylaminocarbonyl, di-C$_{1-2}$-alkylaminocarbonyl, N-oxido-di-C$_{1-2}$-alkylamino, pyrrolidinocarbonyl, morpholinocarbonyl, C$_{1-2}$-alkylcarbonyl-amino or C$_{1-2}$-alkylsulphonylamino group and can additionally be substituted by a methyl group, a cyclohexyl group which is substituted in the 4-position by a 1-pyrrolidinyl, 2-oxo-1-pyrrolidinyl, 2-hydroxymethyl-1-pyrrolidinyl, N-C$_{1-2}$-alkyl-(2-hydroxyethyl)amino, di-(2-hydroxyethyl)amino, N-C$_{1-2}$-alkyl-C$_{1-2}$-alkylcarbonylamino, morpholino, 2-oxo-1-imidazolidinyl, 3-methyl-2-oxo-1-imidazolidinyl, carboxy-C$_{1-2}$-alkyl, carboxy-C$_{1-2}$-alkoxy, C$_{1-2}$-alkoxycarbonyl, C$_{1-2}$-alkyl, C$_{1-2}$-alkoxycarbonyl-C$_{1-2}$-alkoxy, aminocarbonyl-C$_{1-2}$-alkyl, aminocarbonyl-C$_{1-2}$-alkoxy, C$_{1-2}$-alkylamino-carbonyl-C$_{1-2}$-alkyl, C$_{1-2}$-alkylamino-carbonyl-C$_{1-2}$-aloxy, di-C$_{1-2}$-alkylamino-carbonyl-C$_{1-2}$-alkyl, di-C$_{1-2}$-alkylamino-carbonyl-C$_{1-2}$-alkoxy, pyrrolidinocarbonyl-C$_{1-2}$-alkyl, pyrrolidinocarbonyl-C$_{1-2}$-alkoxy, morpholinocarbonyl-C$_{1-2}$-alkyl, morpholinocarbonyl-C$_{1-2}$-alkoxy, piperidinocarbonyl-C$_{1-2}$-alkyl or piperidinocarbonyl-C$_{1-2}$-alkoxy group, a cyclohexyl group in which two hydrogen atoms in the 4-position are replaced by an oxo group or an n-C$_{4-5}$-alkylene bridge, a cyclohexyl group in which the methylene group in the 4-position is replaced by an imino, C$_{1-2}$-alkyl-imino, phenyl-C$_{1-2}$-alkyl-imino, N-methyl-N-oxido-imino, formyl-imino, C$_{1-2}$-alkylcarbonyl-imino, C$_{1-2}$-alkylsulfonyl-imino, C$_{1-2}$-alkoxycarbonyl-imino, cyano-imino, aminocarbonyl-imino, C$_{1-2}$- alkylaminocarbonyl-imino or N,N-di-$C_{1-2}$-alkylaminocarbonyl-imino group, a cyclohexyl group in which the methylene group in the 3-position is replaced by an imino, $C_{1-2}$-alkyl-imino, $C_{1-2}$-alkylcarbonyl-imino, $C_{1-2}$-alkylsulphonyl-imino or $C_{1-2}$-alkoxycarbonyl-imino group, a cyclopentyl group in which the methylene group in the 3-position is replaced by an oxygen atom or an imino, $C_{1-2}$-alkyl-imino, formyl-imino, $C_{1-2}$-alkylcarbonyl-imino, $C_{1-2}$-alkylsulphonyl-imino, $C_{1-2}$-alkoxycarbonyl-imino, cyano-imino or N,N-di-$C_{1-2}$-alkylaminocarbonylimino group, a cyclohexylmethyl group, wherein the cyclohexyl part is substituted in the 4-position by a carboxyl, $C_{1-2}$-alkoxycarbonyl, N,N-di-$C_{1-2}$-alkylaminocarbonyl or morpholinocarbonyl group, a norbornan-2-yl, norbornan-2-yl-methyl, 5-norbornen-2-yl-methyl, bornyl, 3-quinuclidinyl or adamantyl group or $R_{10}$ is a hydrogen atom or a methyl group and $R_{11}$ is a hydroxyl or methoxy group, in particular those compounds in which $R_a$ is a hydrogen atom or a methyl group, $R_b$ is a 2-naphthyl or 5-indanyl group or a phenyl group which is substituted by the radicals $R_1$ to $R_3$, wherein $R_1$ is a hydrogen, fluorine, chlorine, bromine or iodine atom or a methyl, ethyl, tert-butyl, trifluoromethyl, ethynyl, methoxy, cyclopropyl, trifluoromethoxy, cyano, ethoxycarbonyl or nitro group, $R_2$ is a hydrogen, fluorine or chlorine atom or an amino, methyl or trifluoromethyl group and $R_3$ is a hydrogen, chlorine or bromine atom, and $R_c$ is a hydrogen atom or a hydroxyl, methoxy, butyloxy, cyclopentyloxy, 2-[(2-hydroxyethyl)amino]-ethoxy, methylsulphenyl, methylsulphinyl or methylsulphonyl group, a 1-azetidinyl group or a 1-pyrrolidinyl group which is optionally substituted by one or two methyl groups, a 1-piperidinyl group which is substituted by a hydroxymethyl group, a 1-piperidinyl group which is optionally substituted by one or two methyl groups and in which the methylene group in the 4-position can be replaced by an oxygen or sulphur atom or by a carbonyl, sulphinyl, sulphonyl, imino, methyl-imino, N-oxido-N-methyl-imino, 2-propylaminocarbonyl-methyl-imino, phenyl-imino, benzyl-imino, acetyl-imino or methylsulphonylimino group, a 1-piperidinyl group which is substituted in the 3-position by a hydroxyl or diethylaminocarbonyl group or in the 4-position by a hydroxyl, carboxyl, methoxycarbonyl, aminocarbonyl, methylaminocarbonyl, dimethylaminocarbonyl, pyrrolidinocarbonyl, morpholinocarbonyl, amino, acetylamino, methoxycarbonylamino, formylamino, cyanoamino, dimethylaminocarbonylamino, methylsulphonylamino or phenyl group, a 4-hydroxy-4-phenyl-1-piperidinyl group, a 1,2,3,4-tetrahydro-isoquinolin-2-yl or 2,3,4,5-tetrahydro-1H-3-benzazepin-3-yl group, a 1-piperidinyl group in which two hydrogen atoms in the 4-position are replaced by a —$OCH_2CH_2$—O— bridge, a 1-azacyclohept-1-yl group in which two hydrogen atoms in the 3- and 6-position are replaced by a —$CH_2$—$CH_2$— group or an ($R_{10}NR_{11}$)— group, in which $R_{10}$ is a hydrogen atom, a $C_{1-4}$-alkyl group or a 2-hydroxyethyl group and $R_{11}$ is a hydrogen atom, a phenyl group which is optionally substituted by a methyl group, a phenyl group which is substituted in the 4-position by a morpholino or 2-(hydroxymethyl)-1-pyrrolidinyl group, a $C_{1-6}$-alkyl, $C_{3-6}$-cycloalkyl, phenyl-$C_{1-3}$-alkyl, cyclopropylmethyl, allyl, propargyl, 2-hydroxyethyl, 1-hydroxy-2-propyl, 3-hydroxypropyl, 4-hydroxybutyl, 2-methoxyethyl, 1-adamantyl, norbornan-2-yl, aminocarbonylmethyl, 2-(dimethylamino)ethyl, 3-quinuclidinyl, 2,2,2-trifluoroethyl, 4-piperidinyl, 1-methyl-4-piperidinyl, 1-methyl-1-oxido-4-piperidinyl, 1-ethoxycarbonyl-4-piperidinyl, 1-benzyl-4-piperidinyl, 2-(2-hydroxyethoxy)ethyl, 4-tetrahydropyranyl, 1-hydroxy-2-methyl-2-propyl, 1-methoxy-2-methyl-2-propyl, 2-(methylaminocarbonyl)-2-propyl, 2,3-dihydroxy-1-propyl, 2-(morpholino)ethyl, 1-deoxy-1-D-sorbityl, 3-(2-oxo-1-pyrrolidinyl)-propyl, tris-(hydroxymethyl)methyl, 1,3-dihydroxy-2-propyl, 1,3-dihydroxy-2-methyl-2-propyl or bornyl group, a 2-hydroxyethyl group which is substituted in the 2-position by a phenyl group and in the 1-position additionally by a methyl or hydroxymethyl group, a methylcyclohexyl, 4-carboxy-cyclohexyl, 4-methoxycarbonylcyclohexyl, 4-dimethylaminocarbonyl-cyclohexyl, 4-(1-pyrrolidinylcarbonyl)-cyclohexyl, 4-(morpholinocarbonyl)cyclohexyl, 4-[2-(methoxycarbonyl)ethyl]cyclohexyl, 4-(2-carboxyethyl)cyclohexyl, 4-(tert-butyloxycarbonylamino)cyclohexyl, 4-methoxycyclohexyl, 4-aminocyclohexyl, 4-(dimethylamino)cyclohexyl, 4-(N,N-dimethyl-N-oxidoamino)cyclohexyl, 4-(acetylamino)-cyclohexyl, 4-(methylsulphonylamino)-cyclohexyl, 2-hydroxycyclohexyl, 4-hydroxycyclohexyl, 4-(hydroxymethyl)-cyclohexyl, 4-hydroxy-4-methyl-cyclohexyl or 4-oxocyclohexyl group, a methyl group which is substituted by a 1,4,7,10,13-pentaoxacyclopentadecyl or a 1,4,7,10,13,16-hexaoxacyclooctadecyl group, or $R_{10}$ is a methyl group and $R_{11}$ is a methoxy group, their tautomers, their stereoisomers and their salts.

Particularly preferred compounds of the general formula I which may be mentioned are the following:

(1) 4-[(3,4-Dichlorophenyl)amino]-6-[(trans-4-hydroxycyclohexyl)-amino]-pyrimido-[5,4-d]-pyrimidine, (2) 4-[(3-Chloro-4-fluoro-phenyl)amino]-6-[(trans-4-hydroxycyclohexyl)-amino]-pyrimido-[5,4-d]-pyrimidine, (3) 4-[(3-Bromophenyl)amino]-6-[(trans-4-hydroxycyclohexyl)-amino]-pyrimido-[5,4-d]-pyrimidine, (4) 4-[(3-Chlorophenyl)amino]-6-(cyclopropylamino)-pyrimido-[5,4-d]-pyrimidine, (5) 4-[(3-Methylphenyl)amino]-6-(4-amino-1-piperidinyl)-pyrimido[5,4-d]pyrimidine, (6) 4-[(3-Methylphenyl)amino]-6-[(trans-4-aminocyclohexyl)-amino]-pyrimido-[5,4-d]-pyrimidine, (7) 4-[(3-Methylphenyl)amino]-6-(N-(trans-4-hydroxycyclohexyl)-N-methyl-amino)-pyrimido-[5,4-d]-pyrimidine, (8) 4-[(3-Methylphenyl)amino]-6-(4-methoxycarbonylamino-1-piperidinyl)-pyrimido-[5,4-d]-pyrimidine,
(9) 4-[(3-Methylphenyl)amino]-6-[trans-4-(morpholinocarbonyl)-cyclohexylamino]-pyrimido-[5,4-d]-pyrimidine,
(10) 4-[(3-Methylphenyl)amino]-6-[trans-4-(pyrrolidinocarbonyl)cyclohexylamino]-pyrimido-[5,4-d]-pyrimidine,
(11) 4-[(3-Chloro-4-fluoro-phenyl)amino]-6-[N-(trans-4-hydroxycyclohexyl)-N-methyl-amino]-pyrimido-[5,4-d]-pyrimidine,
(12) 4-[(4-Amino-3,5-dichloro-phenyl)amino]-6-[(trans-4-hydroxycyclohexyl)-amino]-pyrimido-[5,4-d]-pyrimidine,
(13) 4-[(3-Chloro-4-fluoro-phenyl)amino]-6-[2-(morpholino)-ethylamino]-pyrimido-[5,4-d]-pyrimidine,
(14) 4-[(4-Amino-3,5-dibromo-phenyl)amino]-6-[(trans-4-hydroxycyclohexyl)-amino]-pyrimido-[5,4-d]-pyrimidine,
(15) 4-[(3-Chloro-4-fluoro-phenyl)amino]-6-morpholino-pyrimido-[5,4-d]-pyrimidine,
(16) 4-[(3-Chloro-4-fluoro-phenyl)amino]-6-(1-hydroxy-2-methyl-2-propylamino)-pyrimido-[5,4-d]-pyrimidine,
(17) 4-[(3-Chloro-4-fluoro-phenyl)amino]-6-(1-hydroxy-2-propylamino)-pyrimido-[5,4-d]-pyrimidine,
(18) 4-[(3-Chloro-4-fluoro-phenyl)amino]-6-(1,3-dihydroxy-2-propylamino)-pyrimido-[5,4-d]-pyrimidine,
(19) 4-[(3-Chloro-4-fluoro-phenyl)amino]-6-[4-amino-1-piperidinyl]-pyrimido-[5,4-d]-pyrimidine,
(20) 4-[(3-Methylphenyl)amino]-6-(4-piperidinyl-amino)-pyrimido[5,4-d]pyrimidine,
(21) 4-[(3-Methylphenyl)amino]-6-(4-formylamino-1-piperidinyl)-pyrimido[5,4-d]pyrimidine,
(22) 4-[(3-Methylphenyl)amino]-6-[(1-ethoxycarbonyl-4-piperidinyl)amino]-pyrimido[5,4-d]pyrimidine, (23) 4-[(3-Methylphenyl)amino]-6-[(3-quinuclidinyl)amino]-pyrimido[5,4-d]pyrimidine,
(24) 4-[(3-Chloro-4-fluoro-phenyl)amino]-6-[(4-aminocyclohexyl)amino]-pyrimido-[5,4-d]-pyrimidine,
(25) 4-[(3-Chloro-4-fluoro-phenyl)amino]-6-(4-piperidinyl-amino)-pyrimido-[5,4-d]-pyrimidine,
(26) 4-[(3-Chloro-4-fluoro-phenyl)amino]-6-[trans-4-(morpholinocarbonyl)cyclohexylamino]-pyrimido-[5,4-d]-pyrimidine,
(27) 4-[(3-Chloro-4-fluoro-phenyl)amino]-6-[trans-4-(pyrrolidinocarbonyl)cyclohexylamino]-pyrimido-[5,4-d]-pyrimidine,
(28) 4-[(4-Fluorophenyl)amino]-6-(cyclopropylamino)-pyrimido-[5,4-d]-pyrimidine,
(29) 4-[(3-Chloro-4-fluoro-phenyl)amino]-6-(cyclopropylamino)-pyrimido-[5,4-d]-pyrimidine, and
(30) 4-[(3,4-Dichlorophenyl)amino]-6-(cyclopropylamino)-pyrimido-[5,4-d]-pyrimidine, and their salts.

The compounds of the general formula I can be prepared, for example, by the following processes:

a) reaction of a compound of the general formula

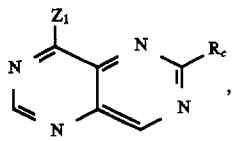

(II)

in which
$R_c$ is as defined above and
$Z_1$ is a leaving group, such as a halogen atom, for example a chlorine or bromine atom, or a methylsulphonyl or hydroxy group, with an amine of the general formula $$H—(R_aNR_b)$$ (III)

in which
$R_a$ and $R_b$ are as defined above.

The reaction is expediently carried out in a solvent, such as isopropanol, butanol, tetrahydrofuran, dioxane, toluene, chlorobenzene, dimethylformamide, dimethylsulphoxide, ethylene glycol monomethyl ether, ethylene glycol diethyl ether or sulpholane, if appropriate in the presence of an inorganic base, for example sodium carbonate or potassium hydroxide, or a tertiary organic base, for example triethylamine or pyridine, where the latter can also simultaneously serve as the solvent, and if appropriate in the presence of a reaction accelerator, such as a copper salt, a corresponding amine hydrohalide or an alkali metal halide, at temperatures between 0° and 200° C., but preferably at temperatures between 60° and 150° C. However, the reaction can also be carried out without a solvent or in an excess of the compound of the general formula III employed.

When $Z_1$ is a hydroxy group the reaction is suitably carried out in the presence of hexamethyldisilazane, preferably without further solvent and optionally in the presence of an accelerator such as an organic acid, for example toluenesulphonic acid, at temperatures between 0° and 200° C., preferably however at temperatures between 60° and 180° C.

b) To prepare compounds of the general formula I in which $R_c$ is one of the radicals mentioned above for $R_c$ linked to the pyrimido[5,4-d]pyrimidine via an oxygen or nitrogen atom or via a mercapto or sulphenyl group:

reaction of a compound of the general formula

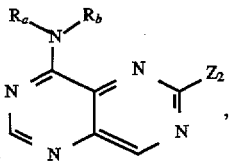

(IV)

in which
$R_a$ and $R_b$ are as defined above and
$Z_2$ is a leaving group, such as a halogen atom or a substituted hydroxyl, mercapto, sulphinyl or sulphonyl group, such as a chlorine or bromine atom or a methoxy, ethoxy, phenoxy, methylsulphinyl, ethylsulphinyl, methylsulphonyl or ethylsulphonyl group, with a compound of the general formula $$X_1—H$$ (V)

in which
$X_1$ is one of the radicals mentioned above for $R_c$ linked to the pyrimido[5,4-d]pyrimidine via an oxygen or nitrogen atom or via a mercapto or sulphenyl group.

The reaction is expediently carried out in a solvent, such as isopropanol, butanol, tetrahydrofuran, dioxane, toluene, chlorobenzene, dimethylformamide, dimethyl sulphoxide, ethylene glycol monomethyl ether, ethylene glycol diethyl ether or sulpholane, if appropriate in the presence of an inorganic base, for example sodium carbonate or potassium hydroxide, or a tertiary organic base, for example triethylamine or pyridine, where the latter can simultaneously also serve as the solvent, and if appropriate in the presence of a reaction accelerator, such as a copper salt, a corresponding amine hydrohalide or an alkali metal halide, at temperatures between 0° and 150° C., but preferably at temperatures between 20° and 120° C. However, the reaction can also be carried out without a solvent or in an excess of the compound of the general formula V employed.

With an alcohol of the general formula V, the reaction is preferably carried out in a corresponding alcohol, and if appropriate in the presence of an organic or inorganic base, such as with the corresponding alkali metal alcoholate, at temperatures between 0° and 100° C.

With a mercapto compound of the general formula V, the reaction is preferably carried out in a solvent with the corresponding alkali metal thiolate or the corresponding thiol and an organic or inorganic base at temperatures between 0° and 80° C.

With water, the reaction is preferably carried out in water or in a mixture of water and an organic solvent, in the presence of an alkali metal hydroxide or a mineral acid, such as hydrochloric acid or sulphuric acid, at temperatures between 20° and 100° C.

c) To prepare compounds of the general formula I in which $R_c$ is one of the radicals mentioned above for $R_c$ linked to the pyrimido[5,4-d]pyrimidine via a sulphinyl or sulphonyl group:

oxidation of a compound of the general formula

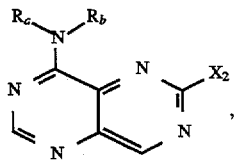

(VI)

in which $R_a$ and $R_b$ are as defined above and $X_2$ is one of the radicals mentioned above for $R_c$ linked to the pyrimido[5,4-d]pyrimidine via a sulphur atom.

The oxidation is preferably carried out in a solvent or solvent mixture, for example in water, water/pyridine, acetone, methylene chloride, glacial acetic acid, glacial acetic acid/acetic anhydride, dilute sulphuric acid or triftrifluoroacetic acid, and, depending on the oxidizing agent used, expediently at temperatures between −80° and 100° C.

To prepare a corresponding sulphinyl compound of the general formula I, the oxidation is expediently carried out with one equivalent of the oxidizing agent used, for example with hydrogen peroxide in glacial acetic acid, trifluoroacetic acid or formic acid at 0° to 20° C. or in acetone at 0° to 60° C., with a per-acid, such as performic acid, in glacial acetic acid or trifluoroacetic acid at 0° to 50° C., or with m-chloroperbenzoic acid in methylene chloride, chloroform or dioxane at −20° to 80° C., with sodium metaperiodate in aqueous methanol or ethanol at −15° to 25° C., with bromine in glacial acetic acid or aqueous acetic acid, optionally in the presence of a weak base, such as sodium acetate, with N-bromosuccinimide in ethanol, with tert-butylhypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C., and with sulphuryl chloride in methylene chloride at −70° C., the thioether-chlorine complex thereby obtained expediently being hydrolyzed with aqueous ethanol.

To prepare a sulphonyl compound of the general formula I, the oxidation is carried out starting from a corresponding sulphinyl compound, expediently with one or more equivalents of the oxidizing agent used, or starting from a corresponding sulphenyl compound, expediently with two or more equivalents of the oxidizing agent used, for example with hydrogen peroxide in glacial acetic acid/acetic anhydride, trifluoroacetic acid or in formic acid at 20° to 100° C. or in acetone at 0° to 60° C., with a per-acid, such as performic acid or m-chloroperbenzoic acid, in glacial acetic acid, trifluoroacetic acid, methylene chloride or chloroform at temperatures between 0° and 60° C., with nitric acid in glacial acetic acid at 0° to 20° C., and with chromic acid or potassium permanganate in glacial acetic acid, water/sulphuric acid or in acetone at 0° to 20° C.

To prepare mixtures of a sulphinyl and sulphonyl compound of the general formula I, the oxidation is carried out starting from a corresponding sulphenyl compound, preferably in methylene chloride, by treatment with a corresponding amount of m-chloroperbenzoic acid at temperatures between 20° C. and the reflux temperature of the reaction mixture.

d) To prepare a compound of the general formula I in which $R_c$ is a hydrogen atom:

dehalogenation of a compound of the general formula

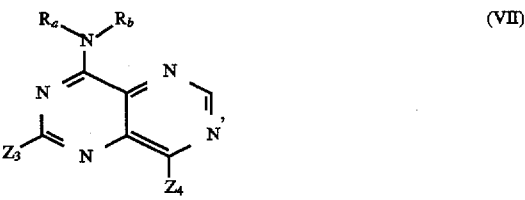

(VII)

in which $R_a$ and $R_b$ are as defined above and $Z_3$ and $Z_4$, which can be identical or different, are each a halogen atom, such as a chlorine or bromine atom.

The dehalogenation is carried out with hydroiodic acid and diphosphorus tetraiodide, where the hydriodic acid can simultaneously serve as the solvent, at temperatures between 20° and 100° C., preferably at 50° C., and by subsequent heating with a hydrogenation catalyst, such as palladium/charcoal, in a suitable solvent, such as dioxane, ethyl acetate or ethylglycol diethyl ether, to 70° to 125° C., preferably to the reflux temperature of the solvent used.

If a compound of the general formula I which contains an amino, alkylamino or imino group is obtained according to the invention, this can be converted into a corresponding acyl or sulphonyl compound of the general formula I by means of acylation or sulphonylation, or if a compound of the general formula I which contains an amino, alkylamino or imino group is obtained according to the invention, this can be converted into a corresponding alkyl compound of the general formula I by means of alkylation or reductive alkylation, or if a compound of the general formula I which contains a carboxyl group is obtained according to the invention, this can be converted into a corresponding ester of the general formula I by means of esterification, or if a compound of the general formula I which contains a carboxyl or ester group is obtained according to the invention, this can be converted into a corresponding amide of the general formula I by means of amidation, or if a compound of the general formula I which contains a primary or secondary hydroxyl group is obtained according to the invention, this can be converted into a corresponding carbonyl compound of the general formula I by means of oxidation.

If appropriate, the subsequent esterification is carried out in a solvent or solvent mixture, such as methylene chloride, dimethylformamide, benzene, toluene, chlorobenzene, tetrahydrofuran, benzene/tetrahydrofuran or dioxane, or particularly advantageously in a corresponding alcohol, if appropriate in the presence of an acid, such as hydrochloric acid, or in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, and if appropriate additionally in the presence of 4-dimethylamino-pyridine, N,N'-carbonyldiimidazole or triphenylphosphine/carbon tetrachloride, expediently at temperatures between 0° and 150° C., preferably at temperatures between 0° and 80° C.

If appropriate, the subsequent acylation or sulphonylation is carried out in a solvent or solvent mixture, such as methylene chloride, dimethylformamide, benzene, toluene, chlorobenzene, tetrahydrofuran, benzene/tetrahydrofuran or dioxane, which a corresponding acyl or sulphonyl derivative, if appropriate in the presence of a tertiary organic base or in the presence of an inorganic base or in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, and if appropriate additionally in the presence of 4-dimethylaminopyridine, N,N'-carbonyldiimidazole or triphenylphosphine/carbon tetrachloride, expediently at temperatures between 0° and 150° C., preferably at temperatures between 0° and If appropriate, the subsequent alkylation is carried out in a solvent or solvent mixture, such as methylene chloride, dimethylformamide, benzene, toluene, chlorobenzene, tetrahydrofuran, benzene/tetrahydrofuran or dioxane, with an alkylating agent, such as a corresponding halide or sulphonic acid ester, for example with methyl iodide, ethyl bromide, dimethyl sulphate or benzyl chloride, if appropriate in the presence of a tertiary organic base or in the presence of an inorganic base, expediently at temperatures between 0° and 150° C., preferably at temperatures between 0° and 100° C.

The subsequent reductive alkylation is carried out with a corresponding carbonyl compound, such as formaldehyde, acetaldehyde, propionaldehyde, acetone or butyraldehyde, in the presence of a complex metal hydride, such as sodium borohydride, lithium borohydride or sodium cyanoborohydride, expediently at a pH of 6–7 and at room temperature or in the presence of a hydrogenation catalyst, for example with hydrogen in the presence of palladium/charcoal, under a hydrogen pressure of 1 to 5 bar. However, the methylation is preferably carried out in the presence of formic acid as the reducing agent at elevated temperatures, for example at temperatures between 60° and 120° C.

The subsequent amidation is carried out by reaction of a corresponding reactive carboxylic acid derivative with a corresponding amine, if appropriate in a solvent or solvent mixture, such as methylene chloride, dimethylformamide, benzene, toluene, chlorobenzene, tetrahydrofuran, benzene/tetrahydrofuran or dioxane, where the amine employed can simultaneously serve as the solvent, if appropriate in the presence of a tertiary organic base or in the presence of an inorganic base, or with a corresponding carboxylic acid in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N,-dicyclohexylcarbodiimide, N,N'-dicyclohexylcarbodiimide/N-hydroxysuccinimide or 1-hydroxybenzotriazole, and if appropriate additionally in the presence of 4-dimethylamino-pyridine, N,N'-carbonyldiimidazole or triphenylphosphine/carbon tetrachloride, expediently at temperatures between 0° and 150° C., preferably at temperatures between 0° and 80° C.

If appropriate, the subsequent oxidation is carried out in a solvent, such as methylene chloride, water, dimethylformamide, benzene, chlorobenzene, tetrahydrofuran or dioxane, with an oxidizing agent, such as chromosulphuric acid, chromium trioxide and pyridine, pyridinium dichromate, pyridinium chlorochromate, oxalyl chloride/dimethylsulphoxide/triethylamine, tetra-n-propyl peruthenate/N-methylmorpholine N-oxide or ruthenium trichloride/sodium metaperiodate, expediently at temperatures between −80° and 100° C., preferably at temperatures between −80° C. and room temperature.

In the reactions described above, any reactive groups present, such as hydroxyl, carboxyl, phosphono, O-alkylphosphono, amino, alkylamino or imino groups, can be protected during the reaction by customary protective groups, which are split off again after the reaction.

For example, a possible protective radical for a hydroxyl group is the trimethylsilyl, acetyl, benzoyl, methyl, ethyl, tert-butyl, trityl, benzyl or tetrahydropyranyl group, a possible protective radical for a carboxyl group is the trimethylsilyl, methyl, ethyl, tert-butyl, benzyl or tetrahydropyranyl group, a possible protective radical for a phosphono group is an alkyl group, such as the methyl, ethyl, isopropyl or n-butyl group, or the phenyl or benzyl group, a possible protective radical for an amino, alkylamino or imino group is the formyl, acetyl, trifluoroacetyl, ethoxycarbonyl, tert-butoxycarbonyl, benzyloxycarbonyl, benzyl, methoxybenzyl or 2,4-dimethoxybenzyl group, and additionally the phthalyl group for the amino group, and a possible protective radical for the nitrogen atom of a 1-aza-bicycloalkyl group such as the quinuclidinyl group, is the benzyl group or borane.

The subsequent splitting off, where appropriate, of a protective radical used is carried out, for example, hydrolyrically in an aqueous solvent, for example in water, isopropanol/water, acetic acid/water, tetrahydrofuran/water or dioxane/water, in the presence of an acid, such as trifluoroacetic acid, hydrochloric acid or sulphuric acid, or in the presence of an alkali metal base, such as sodium hydroxide or potassium hydroxide, or aprotically, for example in the presence of iodotrimethylsilane, at temperatures between 0° and 120° C., preferably at temperatures between 10° and 100° C.

However, a benzyl, methoxybenzyl or benzyloxycarbonyl radical is split off, for example hydrogenolytically, for example with hydrogen in the presence of a catalyst, such as palladium/charcoal, in a suitable solvent, such as methanol, ethanol, ethyl acetate or glacial acetic acid, if appropriate with the addition of an acid, such as hydrochloric acid, at temperatures between 0° and 100° C., but preferably at room temperatures of between 20° and 60° C., and under a hydrogen pressure of 1 to 7 bar, but preferably 3 to 5 bar. However, a 2,4-dimethoxybenzyl radical is preferably split off in trifluoroacetic acid in the presence of anisole.

A tert-butyl or tert-butyloxycarbonyl radical is preferably split off by treatment with an acid, such as trifluoroacetic acid or hydrochloric acid, or by treatment with iodotrimethylsilane, if appropriate using a solvent, such as methylene chloride, dioxane, methanol or diethyl ether.

A trifluoroacetyl radical is preferably split off by treatment with an acid, such as hydrochloric acid, if appropriate in the presence of a solvent, such as acetic acid, at temperatures between 50° and 120° C., or by treatment with sodium hydroxide solution, if appropriate in the presence of a solvent, such as tetrahydrofuran, at temperatures between 0° and 50° C.

A phthalyl radical is preferably split off in the presence of hydrazine or a primary amine, such as methyl-amine, ethylamine or n-butylamine, in a solvent, such as methanol, ethanol, isopropanol, toluene/water or dioxane, at temperatures between 20° and 50° C.

The complex of a 1-aza-bicycloalkyl group, such as the quinuclidinyl group, with borane is preferably split by treatment with an acid, such as hydrochloric acid, and if appropriate in the presence of a solvent, such as methanol, ethanol, acetic acid or dioxane, at temperatures between 0° C. and the boiling point of the reaction mixture. During this reaction, any ester group present can be converted simultaneously into the corresponding carboxyl group.

The splitting of only one alkyl radical from an O,O'-dialkylphosphono group is carried out, for example, with sodium iodide in a solvent, such as acetone, ethyl methyl ketone, acetonitrile or dimethylformamide, at temperatures between 40° and 150° C., but preferably at temperatures between 60° and 100° C.

Both alkyl radicals are split off from an O,O'-dialkylphosphono group, for example, with iodotrimethylsilane, bromotrimethylsilane or chlorotrimethylsilane/sodium iodide in a solvent, such as methyl chloride, chloroform or acetonitrile, at temperatures between 0° C. and the boiling point of the reaction mixture, but preferably at temperatures between 20° and 60° C.

Furthermore, the resulting compounds of the general formula I, as has already been mentioned above, can be separated into their enantiomers and/or diastereomers. Thus, for example, cis/trans mixtures can be separated into their cis and trans isomers and compounds having at least one optically active carbon atom can be separated into their enantiomers.

Thus, for example, the cis/trans mixtures obtained can be separated by chromatography into their cis and trans isomers, the resulting compounds of the general formula I which occur in racemates can be separated into their optical antipodes by methods known per se (see Allinger N. L. and Eliel E. L. in "Topics in Stereochemistry", Volume 6, Wiley Interscience 1971) and compounds of the general formula I with at least 2 asymmetric carbon atoms can be separated on the basis of their physico-chemical differences by methods known per se, for example by chromatography and/or fractional crystallization, into their diastereomers which, if these are obtained in the racemic form, can then be separated into the enantiomers as mentioned above.

The separation of enantiomers is preferably carried out by column separation over chiral phases or by recrystallization from an optically active solvent or by reaction with an optically active substance which forms salts or derivatives, such as, for example, esters or amides, with the racemic compound, in particular acids and their activated derivatives or alcohols, and separation of the diastereomeric salt mixture or derivative obtained in this manner, for example on the basis of different solubilities, it being possible for the free antipodes to be liberated from the pure diastereomeric salts or derivatives by the action of suitable agents. Particularly customary optically active acids are, for example, the D and L forms of tartaric acid or dibenzoyltartaric acid, di-o-tolyltartaric acid, malic acid, mandelic acid, camphorsulphonic acid, glutamic acid, aspartic acid or quinic acid. A possible optically active alcohol is, for example, (+)- or (−)-menthol, and a possible optically active acyl radical in amides is, for example, (+)- or (−)-menthyloxycarbonyl.

The resulting compounds of the formula I furthermore can be converted into their salts, in particular into their physiologically tolerated salts with inorganic or organic acids for pharmaceutical use. Possible acids for this are, for example, hydrochloric acid, hydrobromic acid, sulphuric acid, phosphoric acid, fumaric acid, succinic acid, lactic acid, citric acid, tartaric acid or maleic acid.

If desired, the new compounds of the formula I thus obtained, if these contain a carboxyl, phosphono, O-alkylphosphono, sulpho or 5-tetrazolyl group, can furthermore subsequently be converted into their salts, with inorganic or organic bases, in particular into their physiologically tolerated salts for pharmaceutical use.

Possible bases for this are, for example, sodium hydroxide, potassium hydroxide, arginine, cyclohexylamine, ethanolamine, diethanolamine and triethanolamine.

The compounds of the general formulae II to V used as starting substances are known from the literature in some cases, or these are obtained by processes known per se from the literature (see Examples I to XVII).

As already mentioned above, the compounds of the general formula I according to the invention and their physiologically tolerated salts have valuable pharmacological properties, in particular a specific inhibiting action on signal transduction mediated by epidermal growth factor receptor (EGF-R), it being possible for this to be caused, for example, by inhibition of ligand bonding, receptor dimerization or tyrosine kinase itself. It is furthermore possible for the signal transmission to be blocked at signals situated further down.

The biological properties of the new compounds were tested as follows:

The inhibition of EGF-R-mediated signal transmission can be detected, for example, with cells which express human EGF-R, the survival and proliferation of which depend on stimulation by EGF or TGF-alpha. An interleukin-3 (IL-3)-dependent cell line of murine origin which was changed genetically such that it expresses functional human EGF-R was used here. The proliferation of these cells, called F/L-HERc, can therefore be stimulated either by murine IL-3 or by EGF (see von Rüden, T. et al. in EMBO J. 7, 2749–2756 (1988) and Pierce, J. H. et al. in Science 239, 628–631 (1988)).

The starting material used for the F/L-HERc cells was the cell line $FDC-P_1$, the preparation of which has been described by Dexter, T. M. et al. in J. Exp. Med. 152, 1036–1047 (1980). Alternatively, however, other growth factor-dependent cells can also be used (see, for example, Pierce, J. H. et al. in Science 239, 628–631 (1988), Shibuya, H. et al. in Cell 70, 57–67 (1992) and Alexander, W. S. et al. in EMBO J. 10, 3683–3691 (1991)). Recombinant retroviruses were used for expression of the human EGF-R cDNA (see Ullrich, A. et al. in Nature 309, 418–425 (1984)), as described in yon Rüden, T. et al., EMBO J. 7, 2749–2756 (1988), with the difference that the retroviral vector LXSN (see Miller, A. D. et al. in BioTechniques 7, 980–990 (1989)) was used for expression of the EGF-R cDNA and the line GP+E86 (see Markowitz, D. et al. in J. Virol. 62, 1120–1124 (1988)) was used as the packing cell.

The test was carried out as follows:

F/L HERc cells were cultured at 37° C. and 5% $CO_2$ in RPMI/1640 medium (BioWhittaker), supplemented with 10% foetal bovine serum (FCS, Boehringer Mannheim), 2 mM glutamine (BioWhittaker), standard antibiotics and 20 ng/ml of human EGF (Promega). For investigation of the inhibitory activity of the compounds according to the invention, $1.5 \times 10^4$ cells per well were cultured in triplicate in 96-well plates in the above medium (200 μl), proliferation of the cells being stimulated with either EGF (20 ng/ml) or murine IL-3. Culture stocks of the cell line X63/0 mIL-3 were used as the source for IL-3 (see Karasuyama, H. et al. in Eur. J. Immunol. 18, 97–104 (1988)). The compounds according to the invention were dissolved in 100% dimethyl sulphoxide (DMSO) and added to the cultures in various dilutions, the maximum DMSO concentration being 1%. The cultures were incubated at 37° C. for 48 hours.

To determine the inhibitory activity of the compounds according to the invention, the relative cell count was measured in OD units with Cell Titer 96™ Aqueous Non-Radioactive Cell Proliferation Assay (Promega). The relative cell count was calculated in per cent of the control (F/LHERc cells without inhibitor) and the active compound concentration which inhibits the proliferation of the cells to 50% ($IC_{50}$) was deduced. The following results were obtained here:

| Compound (Example No.) | Inhibition of EGF-dependent proliferation $IC_{50}$ [μM] | Inhibition of IL-3-dependent proliferation $IC_{50}$ [μM] |
| --- | --- | --- |
| 1(3)   | 2.5    | >10 |
| 1(5)   | 1.0    | >10 |
| 1(6)   | 0.005  | >10 |
| 1(10)  | 0.5    | >10 |
| 1(13)  | 0.3    | >10 |
| 1(17)  | 0.04   | >3  |
| 1(19)  | 0.05   | >10 |
| 1(23)  | 0.025  | >3  |
| 1(58)  | 0.02   | >3  |
| 1(62)  | 0.040  | >1  |
| 1(72)  | 0.003  | >3  |
| 1(108) | 0.050  | >10 |
| 1(109) | 0.015  | 10  |
| 1(110) | 0.002  | >10 |
| 3(5)   | 0.05   | >3  |
| 3(18)  | 0.05   | >3  |
| 3(19)  | 0.015  | >3  |
| 3(45)  | 0.020  | >1  |
| 4(1)   | 2      | >10 |
| 1(129) | 0.008  | >20 |
| 1(183) | 0.005  | >20 |
| 1(204) | 0.0008 | >10 |
| 1(134) | 0.013  | >10 |
| 1(207) | 0.002  | >10 |
| 1(201) | 0.032  | >10 |
| 1(61)  | 0.032  | 9   |
| 1(140) | 0.005  | >10 |
| 1(170) | 0.015  | >10 |
| 1(197) | 0.9    | 10  |
| 1(193) | 0.004  | 10  |

The compounds according to the invention also inhibit EGF-stimulated proliferation of the human tumour cell line KB, which originates from an oral epidermoid carcinoma and over-expresses the EGF receptor (e.g. Aboud-Pirak, E. et al., J. Natl. Cancer. Inst. 80, 1605–11 (1988)). KB cells (obtained from ATCC) were passaged in DMEM (BioWhittaker) in the presence of 10% FCS (Boehringer Mannheim), 50 μM beta-mercaptoethanol and standard antibiotics. As an indicator of EGF/TGF-alpha-stimulated cell proliferation, the EGF-inducedDNA synthesis was determined by measurement of the incorporation of radioactively labelled thymidine. For this, the celels were washed twice and 1500 cells per well were plated out in a 96-well plate in 200 μl IMDM (BioWhittaker) without serum in the presence of 50 μM beta-mercaptoethanol, standard antibiotics, TGF-alpha [10 ng/ml] or EGF [20 ng/ml] and various concentrations of the substances according to the invention (triplicates, maximum DMSO concentration 1%, see proliferation test with F/L-HERc cells). After 60 hours, [$^3$H]-thymidine (0.1 μCi in 10 μl) was added for about 16–18 hours. Subsequent measurement of the thymidine incorporation gave $IC_{50}$ values of 0.1–1 μM for inhibition of the EGF/TGF-alpha-stimulated KB cell proliferation for compounds 2, 6, 17, 18, 19, 72, 83, 93, 95, 96 and 104 of Example 1.

The compounds of the general formula I according to the invention thus inhibit signal transduction of tyrosine kinases, as has been demonstrated by. the example of the human EGF receptor, and are therefore useful for the treatment of pathophysiological processes caused by hyperfunction of tyrosine kinases. These are, for example, benign or malignant tumours, in particular tumours of epithelial and neuroepithelial origin, metastatic spread and abnormal proliferation of vascular endothelial cells (neoangiogenesis).

The compounds of .the general formula I and their physiologically tolerated salts furthermore can be used for the treatment of other diseases caused by aberrant functioning of tyrosine kinases, such as, for example, epidermal hyperproliferation (psoriasis), inflammatory processes, diseases of the immune system, hyperproliferation of hematopoietic cells and the like.

On the basis of their biological properties, the compounds according to the invention can be used by themselves or in combination with other pharmacologically active compounds, for example in tumour therapy by monotherapy or in combination with other anti-tumour therapeutics, for example in combination with topoisomerase inhibitors (for example etoposide), mitosis inhibitors (for example vinblastin), compounds which interact with nucleic acids (for example cis-platin, cyclophosphamide and adriamycin), hormone antagonists (for example tamoxifen), inhibitors of metabolic processes (for example 5-FU and the like), cytokines (for example interferons), antibodies and the like. These combinations can be administered either simultaneously or sequentially.

When used pharmaceutically, the compounds according to the invention are as a rule used on warm-blooded vertebrates, in particular on humans, in dosages of 0.01–100 mg/kg of body weight, preferably 0.1–15 mg/kg. For administration, these are incorporated into customary galenical formulations, such as tablets, coated tablets, capsules, powders, suspensions, solutions, sprays or suppositories, with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances, such as hard fat, or suitable mixtures thereof.

The following examples are intended to illustrate the present invention in more detail without limiting it:

EXAMPLE I

4-[(3-Methylphenyl)amino]-2,8-dichloro-pyrimido [5,4-d]-pyrimidine 0.45 g of 3-methylaniline and 0.42 g of triethylamine are added to 1.0 g of 2,4,8-trichloro-pyrimido[5,4-d]pyrimidine in 20 ml of methylene chloride at 0° to −10° C. and the mixture is stirred at this temperature for 1.5 hours. Water is then added and the organic phase is separated off, dried and concentrated. The residue is purified by chromatography over an aluminium oxide column with petroleum ether/ethyl acetate (10:2).

Yield: 0.51 g (39% of theory),

Melting point: 180°–181° C.

The following compounds are obtained analogously to Example I:

(1) 4-[(3-Trifluoromethylphenyl)amino]-2,8-dichloro-pyrimido[5,4-d]pyrimidine $R_f$ value: 0.56 (aluminium oxide; petroleum ether/ethyl acetate =2:1)

(2) 4-[(3-Bromophenyl)amino]-2,8-dichloro-pyrimido[5,4-d]pyrimidine

Melting point: 205°–208° C.

$R_f$ value: 0.50 (aluminium oxide; petroleum ether/ethyl acetate =2:1)

(3) 4-[(3-Chlorophenyl)amino]-2,8-dichloropyrimido[5,4-d]pyrimidine $R_f$ value: 0.67 (aluminium oxide; petroleum ether/ethyl acetate =2:1)

(4) 4-(Phenylamino)-2,8-dichloro-pyrimido[5,4-d]pyrimidine $R_f$ value: 0.50 (aluminium oxide; petroleum ether/ethyl acetate =2:1)

EXAMPLE II

4-Hydroxy-6-methylsulphinyl-pyrimido[5,4-d]pyrimidine and 4-hydroxy-6-methylsulphonyl-pyrimido[5,4-d]pyrimidine 2.0 g of 4-hydroxy-6-methylthio-pyrimido[5,4-d]pyrimidine and 8 g of 3-chloroperoxybenzoic acid (content: 50%) are stirred vigorously in 50 ml of methylene chloride for 3 hours. The precipitate is filtered off with suction, washed with ethyl acetate and dried.

Yield: 2.2 g $R_f$ value: 0.27 and 0.50 (silica gel; methylene chloride/ethyl acetate/methanol=10:4:3)

EXAMPLE III

4-Hydroxy-6-(cyclopropylamino)-pyrimido[5,4-d]pyrimidine 2.2 g of a mixture of 4-hydroxy-6-methylsulphinyl-pyrimido[5,4-d]pyrimidine and 4-hydroxy-6-methylsulphonylpyrimido[5,4-d]pyrimidine are heated under reflux in 10 ml of cyclopropylamine for 3 hours. After cooling, the mixture is concentrated, the residue is stirred with water and the solid is filtered off with suction and dried.

Yield: 1.7 g

Melting point: >240° C.

$R_f$ value: 0.45 (silica gel; methylene chloride/ethyl acetate/methanol=10:4:3)

EXAMPLE IV

4-Chloro-6-(cyclopropylamino)-pyrimido[5,4-d]pyrimidine 1.7 g of 4-hydroxy-6-(cyclopropylamino)-pyrimido[5,4-d]pyrimidine are heated under reflux with 50 ml of thionyl chloride with the addition of 4 drops of dimethylformamide for 1.5 hours. The reaction mixture is concentrated, methylene chloride is added and the mixture is concentrated again. The residue is then partitioned between methylene chloride and an aqueous potassium carbonate solution. The aqueous phase is extracted twice more with methylene chloride and the combined organic phases are dried and concentrated. The product is reacted further without further purification.

Melting point: 135° C. (decomposition)

$R_f$ value: 0.53 (silica gel; petroleum ether/ethyl acetate= 2:1)

The following compound is obtained analogously to Example IV:

(1) 4-chloro-6-methylthio-pyrimido[5,4-d]pyrimidine

Melting point: 90°–92° C.

$R_f$ value: 0.63 (silica gel; petroleum ether/ethyl acetate= 7:3)

EXAMPLE V

5-Amino-2-methylthio-pyrimidine-4-carboxylic acid 131.4 g of 5-bromo-2-methylthio-pyrimidine-4-carboxylic acid, 860 ml of concentrated aqueous ammonia and 2.42 g of copper(II) sulphate, dissolved in 34 ml of water, are shaken in a bomb tube at 95° C. for 4 hours. After cooling, the precipitate is filtered off with suction. The precipitate is dissolved in 600 ml of hot water and the solution is filtered over active charcoal. The filtrate is cooled in an ice bath and brought to a pH of 3 with concentrated hydrochloric acid. The precipitate is filtered off with suction and purified by dissolving in dilute sodium hydroxide solution and precipitating with hydrochloric acid.

Yield: 54.6 g (56% of theory),

Melting point: 187° C.

$R_f$ value: 0.35 (silica gel; ethyl acetate/methanol=2:1)

EXAMPLE VI

4-Hydroxy-6-methylthio-pyrimido[5,4-d]pyrimidine

Method A 25 g of 5-amino-2-methylthio-pyrimidine-4-carboxylic acid and 150 ml of formamide are stirred in an oil bath, the oil bath temperature being increased to 180° C. in the course of half an hour. The mixture is stirred at this temperature for a further 1.5 hours. The reaction mixture is then poured hot onto 750 ml of an ice/water mixture. After 2 hours, the precipitate is filtered off with suction, washed with water and dried.

Method B

A mixture of 69 g of 5-amino-2-methylthio-pyrimidine-4-carboxylic acid, 155 g of formamidine acetate and 300 ml of ethoxyethanol is heated at boiling point for 2 hours. The reaction mixture is then cooled to 10° C., 250 ml of water is added and the reaction mixture is allowed to stand for one hour at 10° C. The precipitate is then filtered off with suction, washed with water and dried.

Yield: 59 g (82% of theory)

Melting point: >240° C.

$R_f$ value: 0.63 (silica gel; methylene chloride/ethyl acetate/methanol=10:4:3)

EXAMPLE VII

4-Dibenzylamino-cyclohexanone 1.0 ml of oxalyl chloride is dissolved in 40 ml of methylene chloride and the solution is cooled to −60° C. 1.7 ml of dimethylsulphoxide in 20 ml of methylene chloride are added dropwise, the mixture is stirred for a further two minutes, and 2.95 g of 4-N,N-dibenzylamino-cyclohexanol in 20 ml of methylene chloride are then slowly added dropwise. After 15 minutes, 7.0 ml of triethylamine are added dropwise. After a further 5 minutes, the mixture is warmed to room temperature and stirred for 12 hours. The reaction mixture is washed once with 100 ml each of water and saturated sodium chloride solution. After drying over sodium sulphate, the solvent is distilled off in a rotary evaporator and the crude product is purified over a silica gel column with petroleum ether/ethyl acetate (10:3, then 10:5, then 10:10).

Yield: 2.91 g (99% of theory),

Melting point: 63°–64° C.

EXAMPLE VIII

4-Dibenzylamino-1-methyl-cyclohexanol

A solution of 15.1 ml of 3.0 molar methylmagnesium bromide in 200 ml of ether is added dropwise to a solution of 10.7 g of 4-dibenzylamino-cyclohexanone in 200 ml of ether. The mixture is then heated at the boiling point for 45 minutes and cooled to 0° C. and 300 ml of saturated ammonium chloride solution are cautiously added. The ether phase is separated off, washed with 100 ml each of saturated sodium bicarbonate solution and saturated sodium chloride solution and dried over sodium sulphate. After the solvent has been distilled off in a rotary evaporator, the crude product is purified over an aluminium oxide column with petroleum ether/ethyl acetate (10:1, then 10:3); the diastereomers are thereby separated.

cis-Diastereomer

Yield: 3.73 g (33% of theory),

Melting point: 91°–95° C.

$R_f$ value: 0.52 (aluminium oxide; petroleum ether/ethyl acetate =10:3)

trans-Diastereomer

Yield: 2.33 g (21% of theory),

Melting point: 111°–115° C.

$R_f$ value: 0.29 (aluminium oxide; petroleum ether/ethyl acetate =10:3)

EXAMPLE IX cis-4-Amino-1-methylcyclohexanol 1.5 g of palladium-on-charcoal (10%) are added to a solution of 4.2 g of cis-4-dibenzylamino-methyl-cyclohexanol in 30 ml of methanol and hydrogenation is carried out at room temperature under 3.5 bar until no further hydrogen is taken up. After filtration and evaporation of the solvent in a rotary evaporator, 2.75 g of an oily residue which is employed without further purification are obtained.

$R_f$ value: 0.06 (aluminium oxide; petroleum ether/ethyl acetate =10:4)

The following compound is obtained analogously to Example IX:

(1) trans-4-amino-1-methylcyclohexanol

Melting point: 225°–230° C.

$R_f$ value: 0.13 (aluminium oxide; petroleum ether/ethyl acetate =10:4)

EXAMPLE X trans-4-(Hydroxymethyl)-cyclohexylamine

A solution of 1.4 g of trans-4-amino-cyclohexanecarboxylic acid methyl ester in 30 ml of tetrahydrofuran is added dropwise to 0.9 g of lithium aluminium hydride in 70 ml of tetrahydrofuran at room temperature, while stirring. The mixture is then heated at the boiling point for a further hour. It is cooled to 0° C. and 10% strength potassium hydroxide solution is cautiously added dropwise until a white precipitate has formed. The mixture is decanted and the precipitate is washed four times by addition of 50 ml of tetrahydrofuran each time and decanting off. The organic phases are combined, the solvent is distilled off in a rotary evaporator and the residue is purified by column chromatography over aluminium oxide with an ethyl acetate/methanol/concentrated ammonia mixture (500:180:1).

Melting point: 135°–139° C.

Yield: 0.99 g (84% of theory), $R_f$ value: 0.48 (aluminium oxide; ethyl acetate/methanol/concentrated ammonia=500:180:1)

EXAMPLE XI

4-Tetrahydropyranone oxime 5.0 g of 4-tetrahydropyranone are added dropwise to a mixture of 5.2 g of hydroxylamine hydrochloride and 4.8 g of sodium acetate in 50 ml of water at 60° C., while stirring. After a further hour at 60° C., the mixture is allowed to cool and the solution is extracted three times with 50 ml of ether each time. The combined organic phases are then dried over sodium sulphate, the solvent is distilled off in a rotary evaporator and the residue is employed in the next reaction without further purification.

Melting point: 50°–52° C.

Yield: 4.2 g (74% of theory), $R_f$ value: 0.30 (silica gel; petroleum ether/ethyl acetate= 1:1)

EXAMPLE XII

4-Amino-tetrahydropyran 4.2 g of 4-tetrahydropyranone oxime are dissolved in 100 ml of ethanol and, after addition of 0.5 g of palladium-on-charcoal (10%), are hydrogenated in a Parr apparatus at 90° C. under a hydrogen pressure of 5 bar for 2.5 hours. After cooling, the solvent is distilled off in a rotary evaporator and the residue is used further without further purification.

Yield: 0.7 g (19% of theory) of a colourless oil, $R_f$ value: 0.45 (silica gel; methylene chloride/ethyl acetate/methanol=10:4:2)

EXAMPLE XIII

4-Bromo-cyclopropylbenzene 16 g of bromine are slowly added dropwise to a mixture of 11.8 g of cyclopropylbenzene, 11 g of potassium acetate and 100 ml of glacial acetic acid at 5° C. After 5 hours at 5° C. and 2 hours at 10° C., the mixture is poured onto ice-water and extracted three times with 100 ml of ether each time. The combined organic phases are washed in each case once with sodium thiosulphate solution, water and saturated sodium chloride solution and dried over sodium sulphate. The solvent is distilled off in a rotary evaporator and the residue is filtered with petroleum ether over aluminium oxide. Distillation of the residue gives 6.2 g of a colourless oil (boiling point$_{12}$=108°–112° C.).

$R_f$ value: 0.65 (aluminium oxide; petroleum ether)

EXAMPLE XIV

4-Bromo-2-nitro-cyclopropylbenzene

A mixture of 4.3 ml of 65% strength nitric acid and 5 ml of concentrated sulphuric acid is added to a mixture of 12 g of 4-bromo-cyclopropylbenzene and 20 ml of concentrated sulphuric acid at 0° C. in the course of 30 minutes. The mixture is then poured onto ice-water and extracted three times with 100 ml of methylene chloride each time. The combined organic phases are dried over sodium sulphate. The solvent is distilled off in a rotary evaporator and the residue is purified by column chromatography over aluminium oxide with petroleum ether.

Yield: 3.6 g (25% of theory) of a colourless oil, $R_f$ value: 0.30 (aluminium oxide; petroleum ether)

EXAMPLE XV

2-Amino-cyclopropylbenzene 3.5 g of 4-bromo-2-nitro-cyclopropylbenzene are dissolved in 30 ml of ethanol and, after addition of 0.5 g of palladium-on-charcoal (10%), are hydrogenated in a Parr apparatus at room temperature under a hydrogen pressure of 5 bar for 2.5 hours. After cooling, the solvent is distilled off in a rotary evaporator and the residue is rendered alkaline with 1N sodium hydroxide solution and extracted three times with 50 ml of ether each time. The combined organic phases are dried over sodium sulphate, the solvent is distilled off in a rotary evaporator and the residue is purified by column chromatography.

Yield: 1.3 g (72% of theory) of a colourless oil, $R_f$ value: 0.43 (silica gel; petroleum ether/ethyl acetate= 2:1)

EXAMPLE XVI

2,5-Diamino-benzonitrile 10 g of 2-cyano-4-nitro-aniline are dissolved in 50 ml of dimethylformamide and, after addition of 0.5 g of palladium-on-charcoal (10%), are hydrogenated in a Parr apparatus at room temperature under a hydrogen pressure of 3 bar for 2 hours. After cooling, the mixture is filtered, the solvent is distilled off in a rotary evaporator and the residue is used further without further purification.

Yield: 10.2 g (100% of theory) of a brown, chromatographically uniform oil, $R_f$ value: 0.63 (Silica gel; methylene chloride/ethyl acetate/methanol=10:4:2)

EXAMPLE XVII

1,4-Diamino-2,6-dibromo-benzene 3.0 g of 2,6-dibromo-4-nitro-aniline are dissolved in 150 ml of ethanol, 150 ml of ethyl acetate and 30 ml of dimethylformamide and, after addition of 0.5 g of platinum-on-charcoal (5%), are hydrogenated in a Parr apparatus at room temperature under a hydrogen pressure of 1.5 bar for 1 hour. After cooling, the mixture is filtered, the solvent is distilled off in a rotary evaporator and the residue is purified by column chromatography.

Yield: 1.4 g of a colourless oil, $R_f$ value: 0.47 (silica gel; petroleum ether/ethyl acetate 2:1)

EXAMPLE XVIII

3-(N-Benzyloxycarbonyl)amino-tetrahydrofuran

A solution of 0.74 g of 4-tetrahydrofuran carboxylic acid, 2 ml of triethylamine and 2.2 g of diphenylphosphorylazide in 10 ml of dioxane is heated to boiling for 1 hour. After the addition of 2.7 g of benzylalcohol, the mixture is heated to boiling for a further 12 hours. After evaporation of the solvent in a rotary evaporator the residue is purified by chromatography over a silica gel column using petroleum ether/ethyl acetate (10:3).

Yield: 2.24 g (86% of theory)

Melting point: 54°–56° C.

$R_f$ value: 0.53 (silica gel; petroleum ether/ethyl acetate= 1:1)

EXAMPLE XIX

3-Amino-tetrahydrofuran

A solution of 2.2 g of 3-(N-benzyloxycarbonyl) aminotetrahydrofuran in 30 ml of methanol is combined with 0.49 g of palladium on charcoal (10%) and hydrogenated at ambient temperature under 5 bar until no further hydrogen is taken up. After filtration and evaporation of the solvent in a rotary evaporator, 0.31 g of an oily residue is obtained which is used without any further purification.

Yield: 0.31 g (33% of theory)

$R_f$ value: 0.45 (aluminium oxide; methylene chloride/ ethyl acetate/methanol=10:4:3)

Mass spectrum: $M^+=87$

EXAMPLE XX

4-(2-Hydroxymethyl-1-pyrrolidinyl)aniline

A solution of 1.0 g of 1-(4-nitrophenyl)-2-hydroxymethyl-pyrrolidine in 40 ml of methanol is combined with 0.5 g of palladium on charcoal (5%) and hydrogenated at ambient temperature under 5 bar until no further hydrogen is taken up. After filtration and evaporation of the solvent in a rotary evaporator, a dark coloured residue is obtained which is used without further purification.

Yield: 1.1 g (quant.), $R_f$ value: 0.81 (silica gel; methylene chloride/methanol= 10:3)

EXAMPLE XXI

3-(4-Amino-phenyl)-propionic acid

A mixture of 155 g of 4-nitro-cinnamic acid in 1 l of methanol is mixed with 15 g of palladium on charcoal (10%) and 30 ml of water and hydrogenated at ambient temperature under 3 bar until no more hydrogen is taken up (2 hours). After filtration and evaporation of the solvent in a rotary evaporator, 2 lots of 300 ml of toluene are added in order to eliminate residual water and the solvent is distilled off in a rotary evaporator. In this way 132 g (quant.) of 3-(4-aminophenyl)propionic acid are obtained.

Melting point: 124°–128° C.

EXAMPLE XXII

3-(trans-4-Acetylamino-cyclohexyl)propionic acid

A mixture of 397 g of 3-(4-amino-phenyl)propionic acid, 125 g of NaOH and 160 g of Raney nickel in 5.7 l of water is hydrogenated at 170° C. and 100 bar until no further hydrogen is taken up (30 hours). After filtration and washing the residue with water, 6.3 l of a colourless solution are obtained as the filtrate, which is combined with a solution of 129 g of NaOH in 400 ml of water, after which 454 ml of acetic anhydride are added dropwise thereto within 35 minutes. After 5 hours the precipitate is filtered off, the filtrate is adjusted to pH 4 by the addition of concentrated hydrochloric acid and stirred for 3 hours at 0° C. It is then suction filtered, washed with 250 ml of ice water and dried at 70° C. In this way, 216 g of 3-(trans-4-acetylaminocyclohexyl)propionic acid are obtained.

Yield: 216 g (42% of theory)
Melting point: 193°–196° C.

EXAMPLE XXIII

Methyl 3-(trans-4-amino-cyclohexyl)propionate hydrochloride

A mixture of 185 g of 3-(trans-4-acetylaminocyclohexyl) propionic acid, 500 ml of water and 500 ml of conc. hydrochloric acid is heated to boiling for 68 hours. It is then evaporated to dryness in a rotary evaporator, 5 lots of 300 ml of a 2:1 methanol/toluene mixture are added and the resulting mixture is evaporated down again. The residue is stirred with 450 ml of a 1:2 mixture of acetone and tert.butylmethylether, suction filtered and dried in vacuo over NaOH. In order to complete esterification it is then dissolved in 1 l of methanol and 50 ml of thionylchloride are added dropwise whilst cooling with ice. After 30 minutes the solvent is distilled off in the rotary evaporator, the residue is combined with 300 ml of methanol and evaporated down again. The residue is stirred with 450 ml of a 1:2 mixture of acetone and tert.butylmethylether, suction filtered and dried.

Yield: 178 g (92% of theory)
Melting point: 196°–198° C.

EXAMPLE XXIV trans-4-Dibenzylamino-cyclohexanol 140 ml of benzylbromide are added dropwise to a mixture of 61 g of trans-4-amino-cyclohexanol, 350 ml of water, 350 ml of ethanol and 110 g of potassium carbonate. The mixture is then heated to boiling for 1 hour, cooled and the crystalline residue is suction filtered. The residue is taken up in 1.5 l of cyclohexane, the mixture is boiled, cooled and suction filtered. Washing with cyclohexane and drying in vacuo yields 108 g (92% of theory) of trans-4-dibenzylamino-cyclohexanol.

Melting point: 97°–99° C.

EXAMPLE XXV tert.-Butyl α-(trans-4-amino-cyclohexyloxy)acetate

At ambient temperature, a solution of 262 g of NaOH in 260 ml of water is added dropwise to a mixture of 76 g of trans-4-dibenzylamino-cyclohexanol, 57 ml of tert.-butyl-α-bromo acetate, 700 ml of toluene and 2.8 g of tetrabutylammonium hydrogen sulfate. After 20 hours the organic phase is separated off, washed twice with 100 ml of water and once with saturated sodium chloride solution then dried over magnesium sulfate and the solvent is distilled off using a rotary evaporator.

In this way, 116 g of a pale yellow solid are obtained which is taken up in 1.5 l of methanol without further purification, mixed with 20 g of palladium on charcoal (10%) and hydrogenated at ambient temperature under 5 bar until the uptake of hydrogen ceases (3 hours). After filtration the solvent is distilled off in a rotary evaporator.

Yield: 68 g (quant.) of a yellow oil which is used without further purification in the next reaction.

EXAMPLE XXVI

Methyl α-(trans-4-amino-cyclohexyloxy)acetate hydrochloride 59 g of the oil obtained above are dissolved in 500 ml of methanol. HCl gas is bubbled in at 0° C. for 1 hour and the mixture is stirred for a further 12 hours at ambient temperature. The solvent is distilled off using a rotary evaporator, the residue is triturated with acetone and suction filtered. After drying in vacuo, 34 g (59% of theory) of methyl α-(trans-4-amino-cyclohexyloxy)acetate hydrochloride are obtained in the form of colourless crystals.

Melting point: 157°–160° C.

EXAMPLE XXVII

Methyl trans-4-aminomethyl-cyclohexanecarboxylate hydrochloride 103 g of trans-4-aminomethyl-cyclohexanecarboxylic acid are dissolved in 1 l of methanol and 48 ml of thionylchloride are added dropwise thereto whilst cooling with ice. After 2 hours at ambient temperature the solvent is distilled off using a rotary evaporator, the residue is stirred with 300 ml of tert.-butylmethylether, suction filtered and dried.

Yield: 137 g (quant.)
Melting point: 170°–172° C.

EXAMPLE 1

4-[(3-Methylphenyl)amino]-6-(cyclohexylamino)-pyrimido[5,4-d]pyrimidine 1.3 ml of cyclohexylamine are added to 0.4 g of a mixture of 4-[(3-methylphenyl)amino]-6-methylsulphinyl-pyrimido [5,4-d]pyrimidine and 4-[(3-methylphenyl)amino]-6-methylsulphonylpyrimido[5,4-d]pyrimidine in 10 ml of dioxane and the mixture is stirred at room temperature overnight. The reaction mixture is evaporated, water is added to the residue and the solid is filtered off with suction. The crude product is purified by chromatography over a silica gel column with petroleum ether/ethyl acetate (2:1).

Yield: 0.23 g (54% of theory),
Melting point: 165°–167° C.
$R_f$ value: 0.51 (silica gel; petroleum ether/ethyl acetate= 2:1) Calculated: C 68.24 H 6.63 N 25.13 Found: 68.44 6.79 25.01

The following compounds are obtained analogously to Example 1:

(1) 4-[(3-Methylphenyl)amino]-6-(isobutylamino)-pyrimido[5,4-d]pyrimidine

Melting point: 164°–166° C. Calculated: C 66.21 H 6.54 N 27.25 Found: 66.28 6.64 27.13

(2) 4-[(3-Methylphenyl)amino]-6-(isopropylamino)-pyrimido[5,4-d]pyrimidine

Melting point: 176°–178° C.
$R_f$ value: 0.60 (silica gel; petroleum ether/ethyl acetate 1:1) Calculated: C 65.29 H 6.16 N 28.55 Found: 65.04 6.17 28.26

(3) 4-[(3-Methylphenyl)amino]-6-(1-phenyl-4-piperazinyl)-pyrimido[5,4-d]pyrimidine Melting point: 190°–192° C.
$R_f$ value: 0.43 (silica gel; petroleum ether/ethyl acetate= 2:1) Calculated: C 69.50 H 5.83 N 24.67 Found: 69.70 6.01 24.31

(4) 4-[(3-Methylphenyl)amino]-6-(piperidinyl)-pyrimido[5,4-d]pyrimidine

Melting point: 111°–113° C.

$R_f$ value: 0.84 (silica gel; petroleum ether/ethyl acetate=1:1) Calculated: C 67.48 H 6.29 N 26.23 Found: 67.51 6.36 26.26

(5) 4-[(3-Methylphenyl)amino]-6-methoxy-pyrimido[5,4-d]pyrimidine

Reaction in methanol with sodium methylate

Melting point: 121°–123° C.

$R_f$ value: 0.31 (silica gel; petroleum ether/ethyl acetate=2:1) Calculated: C 62.91 H 4.90 N 26.20 Found: 62.90 4.99 26.13

(6) 4-[(3-Methylphenyl)amino]-6-(tert-butylamino)-pyrimido[5,4-d]pyrimidine

Melting point: 206°–208° C.

$R_f$ value: 0.50 (silica gel; petroleum ether/ethyl acetate=2:1) Calculated: C 66.21 H 6.54 N 27.25 Found: 66.17 6.59 27.12

(7) 4-[(3-Methylphenyl)amino]-6-(2,3,4,5-tetrahydro-1H-3-benzazepin-3-yl)-pyrimido[5,4-d]pyrimidine Melting point: 154°–156° C.

$R_f$ value: 0.86 (silica gel; petroleum ether/ethyl acetate=1:1) Calculated: C 72.23 H 5.80 N 21.97 Found: 71.93 5.82 21.93

(8) 4-[(3-Methylphenyl)amino]-6-(ethylamino)-pyrimido[5,4-d]pyrimidine

Melting point: 160° C.

$R_f$ value: 0.44 (silica gel; petroleum ether/ethyl acetate=1:1) Calculated: C 64.27 H 5.75 N 29.98 Found: 64.22 5.91 29.99

(9) 4-[(3-Methylphenyl)amino]-6-(n-hexylamino)-pyrimido[5,4-d]pyrimidine

Melting point: 116°–118° C.

$R_f$ value: 0.46 (silica gel; petroleum ether/ethyl acetate=1:1) Calculated: C 67.83 H 7.19 N 24.98 Found: 67.77 7.19 24.99

(10) 4-[(3-Methylphenyl)amino]-6-(diethylamino)-pyrimido[5,4-d]pyrimidine

Melting point: 119°–121° C.

$R_f$ value: 0.62 (silica gel; petroleum ether/ethyl acetate=2:1) Calculated: C 66.21 H 6.49 N 27.25 Found: 66.27 6.67 27.31

(11) 4-[(3-Methylphenyl)amino]-6-(dimethylamino)-pyrimido[5,4-d]pyrimidine

Melting point: 120°–121° C.

$R_f$ value: 0.57 (silica gel; petroleum ether/ethyl acetate=1:1) Calculated: C 64.27 H 5.75 N 29.98 Found: 64.17 5.77 30.22

(12) 4-[(3-Methylphenyl)amino]-6-(benzylamino)-pyrimido[5,4-d]pyrimidine

Melting-point: 198°–204° C.

$R_f$ value: 0.66 (silica gel; petroleum ether/ethyl acetate/methanol=10:8:1)

Mass spectrum: $M^+=342$

(13) 4-[(3-Methylphenyl)amino]-6-amino-pyrimido[5,4-d]pyrimidine

Melting point: >260° C.

$R_f$ value: 0.67 (silica gel; petroleum ether/ethyl acetate/methanol=10:8:1.5; application in dimethylformamide)

Mass spectrum: $M^+=252$

(14) 4-(Phenylamino)-6-(1-pyrrolidinyl)-pyrimido[5,4-d]pyrimidine

Melting point: 172°–174° C.

Mass spectrum: $M^+=292$

(15) 4-[(3-Methylphenyl)amino]-6-(methylamino)-pyrimido[5,4-d]pyrimidine

Melting point: 195°–197° C.

$R_f$ value: 0.31 (silica gel; petroleum ether/ethyl acetate 1:1) Calculated: C 63.14 H 5.29 N 31.55 Found: 62.74 5.31 31.09

(16) 4-[(3-Methylphenyl)amino]-6-(4-methyl-1-piperazinyl)-pyrimido[5,4-d]pyrimidine Melting point: 133°–135° C.

$R_f$ value: 0.53 (aluminium oxide; petroleum ether/ethyl acetate=1:1) Calculated: C 64.45 H 6.31 N 29.23 Found: 64.36 6.39 29.03

(17) 4-[(3-Methylphenyl)amino]-6-(cyclopropylamino)-pyrimido[5,4-d]pyrimidine

Melting point: 168°–170° C.

$R_f$ value: 0.48 (silica gel; petroleum ether/ethyl acetate=1:1) Calculated: C 65.96 H 5.18 N 28.84 Found: 65.48 5.69 28.22

(18) 4-[(3-Methylphenyl)amino]-6-(1-pyrrolidinyl)-pyrimido[5,4-d]pyrimidine

Melting point: 145°–147° C.

$R_f$ value: 0.65 (silica gel; petroleum ether/ethyl acetate/methanol=10:5:1)

(19) 4-[(3-Methylphenyl)amino]-6-(morpholino)-pyrimido[5,4-d]pyrimidine

Melting point: 125°–127° C.

$R_f$ value: 0.53 (silica gel; petroleum ether/ethyl acetate/methanol=10:5:1)

(20) 4-(N-Methyl-N-phenyl-amino)-6-(1-pyrrolidinyl)-pyrimido[5,4-d]pyrimidine

Melting point: 128°–130° C.

$R_f$ value: 0.45 (silica gel; petroleum ether/ethyl acetate=1:1) Calculated: C 66.64 H 5.92 N 27.43 Found: 66.54 5.83 27.11

(21) 4-[(3-Methylphenyl)amino]-6-(allylamino)-pyrimido[5,4-d]pyrimidine

Melting point: 152°–156° C.

$R_f$ value: 0.63 (silica gel; petroleum ether/ethyl acetate/methanol=10:8:1)

(22) 4-[(3-Methylphenyl)amino]-6-[(2-methyl-2-buten-4-yl)amino]-pyrimido[5,4-d]pyrimidine

(23) 4-[(3-Methylphenyl)amino]-6-(propargylamino)-pyrimido[5,4-d]pyrimidine

Melting point: 185°–187° C.

$R_f$ value: 0.68 (silica gel; petroleum ether/ethyl acetate/methanol=10:8:1)

(24) 4-[(3-Methylphenyl)amino]-6-[(cyclopropylmethyl)amino)-pyrimido[5,4-d]pyrimidine Melting point: 141°–144° C.

$R_f$ value: 0.71 (silica gel; petroleum ether/ethyl acetate/methanol=10:8:1)

(25) 4-[(3-Methylphenyl)amino]-6-(cyclobutylamino)-pyrimido[5,4-d]pyrimidine

Melting point: 184°–186° C.

$R_f$ value: 0.54 (silica gel; petroleum ether/ethyl acetate/methanol=10:8:1)

(26) 4-[(3-Methylphenyl)amino]-6-[(2-hydroxyethyl)amino-pyrimido[5,4-d]pyrimidine Melting point: 167°–171° C.

$R_f$ value: 0.42 (silica gel; petroleum ether/ethyl acetate/methanol=10:8:2)

(27) 4-[(3-Methylphenyl)amino]-6-[(2-methoxyethyl)amino]pyrimido[5,4-d]pyrimidine Melting point: 128°–131° C.

$R_f$ value: 0.56 (silica gel; petroleum ether/ethyl acetate/methanol=10:8:1)

(28) 4-[(3-Methylphenyl)amino]-6-(1-piperazinyl)-pyrimido[5,4-d]pyrimidine

Melting point: 125°–128° C.

$R_f$ value: 0.37 (silica gel; methylene chloride/methanol=6:1)

Mass spectrum: $M^+=321$

(29) 4-[(3-Methylphenyl)amino]-6-(1-acetyl-4-piperazinyl)-pyrimido[5,4-d]pyrimidine Melting point: 180°–182° C.
R_f value: 0.38 (silica gel; ethyl acetate/methanol=15:1)
Mass spectrum: M⁺=363

(30) 4-[(3-Methylphenyl)amino]-6-(1-methanesulphonyl-4-piperazinyl)-pyrimido[5,4-d]pyrimidine Prepared from the compounds of Example 2 by reaction with piperazine and subsequent reaction with methanesulphonyl chloride in the presence of triethylamine.
Melting point: 248°–250° C.
R_f value: 0.53 (silica gel; methylene chloride/methanol=30:1)
Mass spectrum: M⁺=399

(31) 4-[(3-Methylphenyl)amino]-6-(4-hydroxy-1-piperidinyl)-pyrimido[5,4-d]pyrimidine
Melting point: 205°–207° C.
R_f value: 0.33 (silica gel; petroleum ether/ethyl acetate/methanol=10:10:1)

(32) 4-[(3-Methylphenyl)amino]-6-(3-hydroxy-1-piperidinyl)-pyrimido[5,4-d]pyrimidine
Melting point: 171°–173° C.
R_f value: 0.46 (silica gel; methylene chloride/methanol 9:1)

(33) 4-[(3-Methylphenyl)amino]-6-(4-phenyl-1-piperidinyl)-pyrimido[5,4-d]pyrimidine
Melting point: 148°–150° C.
R_f value: 0.77 (silica gel; petroleum ether/ethyl acetate=1:1)

(34) 4-[(3-Methylphenyl)amino]-6-(1-benzyl-4-piperazinyl)-pyrimido[5,4-d]pyrimidine
Melting point: 132°–134° C.

(35) 4-[(3-Methylphenyl)amino]-6-[(2-phenylethyl)amino]pyrimido[5,4-d]pyrimidine
Melting point: 150°–151° C.
R_f value: 0.56 (silica gel; petroleum ether/ethyl acetate=1:1) Calculated: C 70.77 H 5.66 N 23.58 Found: 70.85 5.82 23.52

(36) 4-[(3-Methylphenyl)amino]-6-(cyclopentylamino)-pyrimido[5,4-d]pyrimidine
Melting point: 178°–180° C.
R_f value: 0.49 (silica gel; petroleum ether/ethyl acetate=1:1) Calculated: C 67.48 H 6.29 N 26.23 Found: 67.42 6.33 25.70

(37) 4-[(3-Methylphenyl)amino]-6-(thiomorpholino)-pyrimido[5,4-d]pyrimidine
Melting point: 125°–127° C.
R_f value: 0.81 (silica gel; petroleum ether/ethyl acetate=1:1)

(38) 4-[(3-Methylphenyl)amino]-6-(S-oxido-thiomorpholino)-pyrimido[5,4-d]pyrimidine
Melting point: 212° C.
R_f value: 0.40 (silica gel; ethyl acetate/methanol=10:1)

(39) 4-[(3-Methylphenyl)amino]-6-(S,S-dioxido-thiomorpholino)-pyrimido[5,4-d]pyrimidine
Melting point: 240° C.
R_f value: 0.30 (silica gel; petroleum ether/ethyl acetate=1:1)

(40) 4-[(3-Methylphenyl)amino]-6-[(carboxymethyl)amino]pyrimido[5,4-d]pyrimidine

(41) 4-[(3-Methylphenyl)amino]-6-[(aminocarbonylmethyl)amino]-pyrimido[5,4-d]pyrimidine
Melting point: 290° C. (decomposition)
R_f value: 0.26 (aluminium oxide; methylene chloride/methanol=9:1)

(42) 4-[(3-Methylphenyl)amino]-6-[(methylaminocarbonylmethyl)amino]-pyrimido[5,4-d]pyrimidine

(43) 4-[(3-Methylphenyl)amino]-6-[(dimethylaminocarbonylmethyl)amino]-pyrimido[5,4-d]pyrimidine

(44) 4-[(3-Methylphenyl)amino]-6-[[(1-pyrrolidinyl)carbonylmethyl]amino]-pyrimido[5,4-d]pyrimidine

(45) 4-[(3-Methylphenyl)amino]-6-[[(morpholinocarbonyl)methyl]amino]-pyrimido[5,4-d]pyrimidine

(46) 4-[(3-Methylphenyl)amino]-6-(4-carboxy-1-piperidinyl)pyrimido[5,4-d]pyrimidine Prepared from the compounds of Example 2 by reaction with piperidine-4-carboxylic acid in a dioxane/sodium hydroxide solution mixture
Melting point: 255°–258° C. (decomposition)
R_f value: 0.21 (silica gel; petroleum ether/ethyl acetate/methanol=10:10:1)
Mass spectrum: M⁺=364

(47) 4-[(3-Methylphenyl)amino]-6-(4-aminocarbonyl-1-piperidinyl)-pyrimido[5,4-d]pyrimidine
Melting point: 242°–244° C. (decomposition)
R_f value: 0.48 (silica gel; petroleum ether/ethyl acetate/methanol=10:10:5)
Mass spectrum: M⁺=363

(48) 4-[(3-Methylphenyl)amino]-6-(3-diethylaminocarbonyl-1-piperidinyl)-pyrimido[5,4-d]pyrimidine
Melting point: 119°–121° C.
R_f value: 0.36 (silica gel; petroleum ether/ethyl acetate/methanol=10:10:1) Calculated: C 65.85 H 6.97 N 23.37 Found: 65.80 7.07 23.17

(49) 4-[(3-Methylphenyl)amino]-6-(8-aza-1,4-dioxaspiro[4,5]decan-8-yl)-pyrimido[5,4-d]pyrimidine
Melting point: 184°–186° C.
R_f value: 0.56 (silica gel; petroleum ether/ethyl acetate=1:1) Calculated: C 63.48 H 5.86 N 22.21 Found: 63.35 6.00 21.89

(50) 4-[(3-Methylphenyl)amino]-6-[(2-dimethylaminoethyl)amino]-pyrimido[5,4-d]pyrimidine
Melting point: 140°–142° C.
R_f value: 0.66 (aluminium oxide; petroleum ether/ethyl acetate/methanol=10:10:1)
Mass spectrum: M⁺=323

(51) 4-[(3-Methylphenyl)amino]-6-[bis-(2-hydroxyethyl)amino]-pyrimido[5,4-d]pyrimidine
Melting point: 180°–182° C.
R_f value: 0.29 (silica gel; petroleum ether/ethyl acetate/methanol/ammonia=5:5:1.25:0.1)
Mass spectrum: M⁺=340

(52) 4-[(3-Methylphenyl)amino]-6-(dibutylamino)-pyrimido[5,4-d]pyrimidine
Melting point: 56°–58° C.
R_f value: 0.57 (silica gel; petroleum ether/ethyl acetate=1:1) Calculated: C 69.20 H 7.74 N 23.06 Found: 69.38 7.80 22.91

(53) 4-[(3-Methylphenyl)amino]-6-(cyclopentyloxy)-pyrimido[5,4-d]pyrimidine
Melting point: 83°–85° C.
R_f value: 0.50 (silica gel; petroleum ether/ethyl acetate=2:1)

Prepared from the compounds of Example 2 using cyclopentanol and metallic sodium.

(54) 4-[(3-Methylphenyl)amino]-6-(4-cyano-1-piperidinyl)-pyrimido[5,4-d]pyrimidine

(55) 4-[(3-Methylphenyl)amino]-6-(2-azaspiro[4,5]decan-2-yl)-pyrimido[5,4-d]pyrimidine

(56) 4-[(3-Methylphenyl)amino]-6-(7-azaspiro[4,5]decan-7-yl)-pyrimido[5,4-d]pyrimidine

(57) 4-[(3-Methylphenyl)amino]-6-(2-butylamino)-pyrimido[5,4-d]pyrimidine
Melting point: 178°–180° C.
R_f value: 0.67 (silica gel; petroleum ether/ethyl acetate=1:1) Calculated: C 66.21 H 6.54 N 27.25 Found: 66.23 6.59 27.19

Mass spectrum: M$^+$=308

(58) 4-[(3-Methylphenyl)amino]-6-(1-hydroxy-2-propylamino)pyrimido[5,4-d]pyrimidine
Melting point: 176°–178° C.
R$_f$ value: 0.33 (silica gel; petroleum ether/ethyl acetate/methanol=10:10:1) Calculated: C 61.92 H 5.85 N 27.08 Found: 61.60 5.97 26.72

(59) 4-[(3-Methylphenyl)amino]-6-(2-carboxy-1-pyrrolidinyl)-pyrimido[5,4-d]pyrimidine

(60) 4-[(3-Methylphenyl)amino]-6-(2-aminocarbonyl-1-pyrrolidinyl)-pyrimido[5,4-d]pyrimidine

(61) 4-[(3-Methylphenyl)amino]-6-(4-amino-1-piperidinyl)-pyrimido[5,4-d]pyrimidine
Melting point: 105°–110° C.
R$_f$ value: 0.12 (silica gel; methylene chloride/methanol=1:1)

(62) 4-[(3-Methylphenyl)amino]-6-[(1-methyl-4-piperidinyl)amino]-pyrimido[5,4-d]pyrimidine
Melting point: 204°–205° C.
R$_f$ value: 0.37 (aluminium oxide; petroleum ether/ethyl acetate/methanol=10:10:0.5) Calculated: C 65.31 H 6.63 N.28.06 Found: 65.23 6.68 27.72

(63) 4-[(3-Methylphenyl)amino]-6-(1,2,3,4-tetrahydro-2-isoquinolinyl)-pyrimido[5,4-d]pyrimidine
Melting point: 95°–97° C.
R$_f$ value: 0.38 (silica gel; petroleum ether/ethyl acetate=7:3)
Mass spectrum: M$^+$=368

(64) 4-[(3-Methylphenyl)amino]-6-(2-aza-bicyclo[2.2.2]octan- 2-yl)-pyrimido[5,4-d]pyrimidine

(65) 4-[(3-Methylphenyl)amino]-6-[(endo-2-norbornyl)amino]-pyrimido[5,4-d]pyrimidine
Melting point: 149°–154° C.
R$_f$ value: 0.78 (silica gel; petroleum ether/ethyl acetate/methanol=10:8:2) Calculated: C 69.34 H 6.40 N 24.26 Found: 69.65 6.49 24.23

(66) 4-[(3-Methylphenyl)amino]-6-[(norbornan-2-yl-methyl)amino]-pyrimido[5,4-d]pyrimidine

(67) 4-[(3-Methylphenyl)amino]-6-[(5-norbornen-2-yl-methyl)amino]-pyrimido[5,4-d]pyrimidine

(68) 4-[(3-Methylphenyl)amino]-6-(R (+)-bornylamino)-pyrimido[5,4-d]pyrimidine
Melting point: 184°–187° C.
R$_f$ value: 0.80 (silica gel; petroleum ether/ethyl acetate/methanol=10:6:1)

(69) 4-[(3-Methylphenyl)amino]-6-[(3-quinuclidinyl)amino]-pyrimido[5,4-d]pyrimidine
Melting point: 186°–189° C.
R$_f$ value: 0.48 (silica gel; petroleum ether/ethyl acetate/methanol 10:5:2) Calculated: C 66.46 H 6.41 N 27.13 Found: 66.09 6.40 27.10

(70) 4-[(3-Methylphenyl)amino]-6-[(cyclopentylmethyl)amino]-pyrimido[5,4-d]pyrimidine

(71) 4-[(3-Methylphenyl)amino]-6-[(1-adamantyl)amino]-pyrimido[5,4-d]pyrimidine
Melting point: 262°–266° C.
R$_f$ value: 0.69 (silica gel; petroleum ether/ethyl acetate/methanol=10:8:1)

(72) 4-[(3-Methylphenyl)amino]-6-[(trans-4-hydroxycyclohexyl)amino]-pyrimido[5,4-d]pyrimidine
Melting point: 226°–228° C.
R$_f$ value: 0.30 (silica gel; petroleum ether/ethyl acetate/methanol=10:8:2)

(73) 4-[(3-Methylphenyl)amino]-6-[(2-hydroxycyclopentyl)amino]-pyrimido[5,4-d]pyrimidine

(74) 4-[(3-Methylphenyl)amino]-6-[(4-dimethylaminocyclohexyl)amino]-pyrimido[5,4-d]pyrimidine

(75) 4-[(3-Methylphenyl)amino]-6-[(3-methylcyclohexyl)amino]-pyrimido[5,4-d]pyrimidine
Melting point: 150°–152° C.
R$_f$ value: 0.76 (silica 9el; petroleum ether/ethyl acetate/methanol=10:8:1)

(76) 4-[(3-Methylphenyl)amino]-6-[(spiro[5,5]undecan-3-yl)amino]-pyrimido[5,4-d]pyrimidine

(77) 4-[(3-Methylphenyl)amino]-6-[(3-cyanopropyl)amino]pyrimido[5,4-d]pyrimidine

(78) 4-[(3-Methylphenyl)amino]-6-(2-aza-bicyclo[2.2.1]heptan-2-yl)-pyrimido[5,4-d]pyrimidine

(79) 4-[(3-Methylphenyl)amino]-6-(3-aza-bicyclo[3.2.2]nonan-3-yl)-pyrimido[5,4-d]pyrimidine
Melting point: 116°–119° C.
R$_f$ value: 0.75 (silica-gel; petroleum ether/ethyl acetate/methanol=10:6:1)

(80) 4-[(3-Methylphenyl)amino]-6-(exo-2-norbornylamino)-pyrimido[5,4-d]pyrimidine
Melting point: 245°–247° C.
R$_f$ value: 0.70 (silica gel; petroleum ether/ethyl acetate/methanol=10:8:1)

(81) 4,6-Bis-[(3-methylphenyl)amino]-pyrimido[5,4-d]pyrimidine
Melting point: 220°–222° C.
R$_f$ value: 0.37 (silica gel; petroleum ether/ethyl acetate=1:2)

(82) 4-[(3-Fluorophenyl)amino]-6-(cyclopropylamino)-pyrimido[5,4-d]pyrimidine
Melting point: 180°–182° C.
R$_f$ value: 0.45 (silica gel; petroleum ether/ethyl acetate=1:1)

(83) 4-[(3-Chlorophenyl)amino]-6-(cyclopropylamino)-pyrimido[5,4-d]pyrimidine
Melting point: 182°–184° C. Calculated: C 57.60 H 4.18 N 26.87 Cl 11.33 Found: 57.66 4.39 26.40 11.24

(84) 4-[(3-Bromophenyl)amino]-6-(cyclopropylamino)-pyrimido[5,4-d]pyrimidine
Melting point: 205°–207° C.
R$_f$ value: 0.63 (silica gel; petroleum ether/ethyl acetate=1:1) Calculated: C 50.42 H 3.66 N 23.52 Br 22.39 Found: 50.29 3.82 23.42 22.65

(85) 4-[(3-Trifluoromethylphenyl)amino]-6-(cyclopropylamino)-pyrimido[5,4-d]pyrimidine
Melting point: 146°–148° C.
R$_f$ value: 0.22 (silica gel; petroleum ether/ethyl acetate 2:1)

(86) 4-[(3-Methoxyphenyl)amino]-6-(cyclopropylamino)-pyrimido[5,4-d]pyrimidine
Melting point: 143°–145° C.
R$_f$ value: 0.50 (silica gel; petroleum ether/ethyl acetate=1:1)

(87) 4-[(3-Ethylphenyl)amino]-6-(cyclopropylamino)-pyrimido[5,4-d]pyrimidine
Melting point: 140°–142° C.
R$_f$ value: 0.55 (silica gel; petroleum ether/ethyl acetate=1:1) Calculated: C 66.86 H 5.61 N 27.52 Found: 66.51 5.92 27.12

(88) 4-[(3-Methylphenyl)amino]-6-hydroxy-pyrimido[5,4-d]pyrimidine
Melting point: >220° C.
R$_f$ value: 0.28 (silica gel; ammonia/methanol=10:1)
Prepared from the compounds of Example 2 and sodium hydroxide solution.

(89) 4-[(3-Methylphenyl)amino]-6-(hydroxyamino)-pyrimido[5,4-d]pyrimidine

(90) 4-[(3-Methylphenyl)amino]-6-(methoxyamino)-pyrimido[5,4-d]pyrimidine

(91) 4-[(3-Methylphenyl)amino]-6-(N-methyl-N-methoxy-amino)-pyrimido[5,4-d]pyrimidine
Melting point: 118°–121° C.
$R_f$ value: 0.60 (silica gel; petroleum ether/ethyl acetate/methanol=10:7:1)

(92) 4-[(3-Methylphenyl)amino]-6-(2,2,2-trifluoroethylamino)-pyrimido[5,4-d]pyrimidine
Melting point: 172°–175° C.
$R_f$ value: 0.59 (silica gel; petroleum ether/ethyl acetate/methanol=10:8:1)

(93) 4-[(3-Chlorophenyl)amino]-6-(1-pyrrolidinyl)-pyrimido[5,4-d]pyrimidine
Melting point: 170°–173° C.
$R_f$ value: 0.68 (silica gel; petroleum ether/ethyl acetate/methanol=10:5:1) Calculated: C 58.81 H 4.63 N 25.72 Cl 10.85 Found: 58.93 4.77 25.52 11.10

(94) 4-[(3-Fluorophenyl)amino]-6-(1-pyrrolidinyl)-pyrimido[5,4-d]pyrimidine
Melting point: 169°–172° C.
$R_f$ value: 0.60 (silica gel; petroleum ether/ethyl acetate/methanol=10:5:1) Calculated: C 61.93 H 4.87 N 27.08 Found: 62.00 4.95 27.07

(95) 4-[(3-Bromophenyl)amino]-6-(isopropylamino)-pyrimido[5,4-d]pyrimidine
Melting point: 181°–184° C.
$R_f$ value: 0.50 (silica gel; petroleum ether/ethyl acetate/methanol=10:5:1) Calculated: C 50.15 H 4.21 N 23.39 Br 22.24 Found: 49.86 4.37 23.11 22.30

(96) 4-[(3-Chlorophenyl)amino]-6-(isopropylamino)-pyrim-ido[5,4-d]pyrimidine
Melting point: 193°–196° C.
$R_f$ value: 0.53 (silica gel; petroleum ether/ethyl acetate/methanol=10:5:1) Calculated: C 57.24 H 4.80 N 26.70 Cl 11.26 Found: 57.48 4.97 26.54 11.85

(97) 4-[(3-Fluorophenyl)amino]-6-(isopropylamino)-pyrim-ido[5,4-d]pyrimidine
Melting point: 195°–200° C.
$R_f$ value: 0.50 (silica gel; petroleum ether/ethyl acetate/methanol=10:5:1) Calculated: C 60.39 H 5.07 N 28.17 Found: 60.13 5.13 28.03

(98) 4-[(3-Bromophenyl)amino]-6-(morpholino)-pyrimido[5,4-d]pyrimidine
Melting point: 183°–187° C.
$R_f$ value: 0.40 (silica gel; petroleum ether/ethyl acetate/methanol=10:5:1) Calculated: C 49.63 H 3.90 N 21.70 Found: 49.59 4.17 21.64

(99) 4-[(3-Chlorophenyl)amino]-6-(morpholino)-pyrimido[5,4-d]pyrimidine
Melting point: 188°–192° C.
$R_f$ value: 0.41 (silica gel; petroleum ether/ethyl acetate/methanol=10:5:1) Calculated: C 56.06 H 4.41 N 24.52 Cl 10.34 Found: 55.75 4.67 24.43 10.97

(100) 4-[(3-Fluorophenyl)amino]-6-(morpholino)-pyrimido[5,4-d]pyrimidine
Melting point: 166°–169° C.
$R_f$ value: 0.48 (silica gel; petroleum ether/ethyl acetate/methanol=10:5:1)

(101) 4-[(3-Methylphenyl)amino]-6-[2-(2'-hydroxyethylamino)ethyloxy]pyrimido[5,4-d]pyrimidine
$R_f$ value: 0.10 (silica gel; petroleum ether/ethyl acetate/methanol/ammonia=5:5:1.25:0.1)
Mass spectrum: $M^+$=340

(102) 4-[(3-Methylphenyl)amino]-6-(1-azetidinyl)-pyrimido[5,4-d]pyrimidine
Melting point: 129°–131° C.
$R_f$ value: 0.51 (silica gel; petroleum ether/ethyl acetate/methanol=10:6:1)

(103) 4-[(3-Bromophenyl)amino]-6-(1-pyrrolidinyl)-pyrimido[5,4-d]pyrimidine
Melting point: 206°–208° C.
$R_f$ value: 0.63 (silica gel; petroleum ether/ethyl acetate/methanol=10:5:1) Calculated: C 51.76 H 4.07 N 22.64 Br 21.52 Found: 51.67 4.22 22.44 22.14

(104) 4-[(3-Bromophenyl)amino]-6-[(trans-4-hydroxycyclohexyl)-amino]pyrimido[5,4-d]pyrimidine
Melting point: 226°–231° C.
$R_f$ value: 0.43 (silica gel; petroleum ether/ethyl acetate/methanol=10:10:2) Calculated: C 52.06 H 4.61 N 20.24 Br 19.24 Found: 52.23 4.83 20.30 19.38

(105) 4-[(3-Methylphenyl)amino]-6-[(3-hydroxypropyl)amino]pyrimido[5,4-d]pyrimidine
Melting point: 186°–190° C.
$R_f$ value: 0.38 (silica gel; petroleum ether/ethyl acetate/methanol=10:10:2) Calculated: C 61.92 H 5.84 N 27.08 Found: 61.90 6.08 26.66

(106) 4-[(3-Methylphenyl)amino]-6-[(4-hydroxybutyl)amino]pyrimido[5,4-d]pyrimidine
Melting point: 195°–201° C.
$R_f$ value: 0.32 (silica gel; petroleum ether/ethyl acetate/methanol=10:10:2) Calculated: C 62.95 H 6.21 N 25.91 Found: 63.04 6.41 25.51

(107) 4-[(3-Methylphenyl)amino]-6-[(cis-4-hydroxycyclohexyl)amino]pyrimido[5,4-d]pyrimidine
Melting point: 212°–216° C.
$R_f$ value: 0.48 (silica gel; petroleum ether/ethyl acetate/methanol=10:8:3) Calculated: C 65.12 H 6.33 N 23.98 Found: 65.06 6.46 23.86

(108) 4-[(3-Methylphenyl)amino]-6-[(trans-4-tert-butyloxycarbonylamino-cyclohexyl)amino]pyrimido[5,4-d]pyrimidine
Melting point: 198°–200° C.
$R_f$ value: 0.55 (silica gel; petroleum ether/ethyl acetate/methanol=10:8:1)
Mass spectrum: $M^+$=449

(109) 4-[(3-Methylphenyl)amino]-6-[(4-oxo-cyclohexyl)amino]pyrimido[5,4-d]pyrimidine
Prepared from the compounds of Example 2 by reaction with trans-4-hydroxycyclohexylamine and subsequent reaction with pyridinium chlorochromate.
Melting point: 215°–218° C.
$R_f$ value: 0.50 (silica gel; petroleum ether/ethyl acetate/methanol=10:8:3)
Mass spectrum: $M^+$=348

(110) 4-[(3-Chlorophenyl)amino]-6-[(trans-4-hydroxycyclohexyl)amino]pyrimido[5,4-d]pyrimidine
Melting point: 219°–223° C.
$R_f$ value: 0.34 (silica gel; petroleum ether/ethyl acetate/methanol=10:8:2) Calculated: C 58.30 H 5.16 N 22.66 Cl 19.56 Found: 58.22 5.06 22.88 9.61

(111) 4-[(3-Fluorophenyl)amino]-6-[(trans-4-hydroxycyclohexyl)amino]pyrimido[5,4-d]pyrimidine
Melting point: 220°–223° C.
$R_f$ value: 0.38 (silica gel; petroleum ether/ethyl acetate/methanol=10:8:2) Calculated: C 61.01 H 5.40 N 23.71 Found: 61.14 5.46 23.83

(112) 4-[(3-Methylphenyl)amino]-6-[(trans-4-methoxycyclohexyl)amino]pyrimido[5,4-d]pyrimidine
Melting point: 188°–191° C.
$R_f$ value: 0.53 (silica gel; petroleum ether/ethyl acetate/methanol=10:8:2) Calculated: C 65.91 H 6.64 N 23.06 Found: 65.75 6.79 22.83

(113) 4-[(3-Methylphenyl)amino]-6-[(trans-4-aminocyclohexyl)amino]pyrimido[5,4-d]pyrimidine
Prepared from the compounds of Example 2 by reaction with trans-4-tert-butyloxy-carbonylamino-cyclohexylamine and subsequent reaction with ethereal hydrogen chloride solution and methanol.

Melting point: >260° C.

$R_f$ value: 0.28 (reversed phase silica gel; methanol/5% strength sodium chloride solution=10:4)

(114) 4-[(3-Methylphenyl-)amino]-6-[(trans-4-methylsulphonylaminocyclohexyl)amino]pyrimido[5,4-d]pyrimidine Prepared from the compounds of Example 2 by reaction with trans-4-tert-butyloxycarbonylamino-cyclohexylamine and subsequent reaction with ethereal hydrogen chloride solution and methanol, as well as subsequent reaction with methanesulphonyl chloride.

Melting point: 192°–195° C.

$R_f$ value: 0.37 (silica gel; petroleum ether/ethyl acetate/methanol=10:8:2)

(115) 4-[(3-Methylphenyl)amino]-6-[(trans-4-acetylaminocyclohexyl)amino]-pyrimido[5,4-d]pyrimidine Prepared from the compounds of Example 2 by reaction with trans-4-tert-butyloxycarbonylamino-cyclohexylamine and subsequent reaction with ethereal hydrogen chloride solution and methanol, as well as subsequent reaction with acetic anhydride and triethylamine.

Melting point: 302°–305° C.

$R_f$ value: 0.38 (silica gel; petroleum ether/ethyl acetate/methanol=10:8:3)

(116) 4-[(3-Methylphenyl)amino]-[6-(trans-4-dimethylaminocyclohexyl)amino]-pyrimido[5,4-d]pyrimidine Prepared from the compounds of Example 2 by reaction with trans-4-tert-butyloxycarbonylamino-cyclohexylamine and subsequent reaction with ethereal hydrogen chloride solution and methanol, as well as subsequent reaction with formic acid, formaldehyde and sodium bicarbonate.

Melting point: 161°–165° C.

$R_f$ value: 0.71 (aluminium oxide, methylene chloride/methanol =20:1) Calculated: C 66.82 H 7.21 N 25.97 Found: 66.74 7.32 26.12

(117) 4-[(3-Methylphenyl)amino]-6-[(cis-4-hydroxy-4-methylcyclohexyl)amino]-pyrimido[5,4-d]pyrimidine
Prepared from the compounds of Examples IX and 2.
Melting point: 194°–196° C.

$R_f$ value: 0.36 (silica gel; petroleum ether/ethyl acetate/methanol=10:8:2)

(118) 4-[(3-Methylphenyl)amino]-6-[(trans-4-hydroxy-4-methylcyclohexyl)amino]-pyrimido[5,4-d]pyrimidine
Prepared from the compounds of Examples IX(1) and 2.
Melting point: 217°–221° C.

$R_f$ value: 0.36 (silica gel; petroleum ether/ethyl acetate/methanol=10:8:2) Calculated: C 65.91 H 6.64 N 23.06 Found: 65.80 6.70 23.26

(119) 4-[(3-Methylphenyl)amino]-6-(N-isopropyl-N-methyl-amino)-pyrimido[5,4-d]pyrimidine
Melting point: 91°–96° C.

$R_f$ value: 0.55 (silica gel; petroleum ether/ethyl acetate/methanol=10:8:2) Calculated: C 66.21 H 6.54 N 27.25 Found: 66.33 6.79 26.99

(120) 4-[(3-Methylphenyl)amino]-6-(N-tert-butyl-N-methylamino)-pyrimido[5,4-d]pyrimidine
Melting point: 136°–139° C.

$R_f$ value: 0.89 (silica gel; petroleum ether/ethyl acetate/methanol=10:8:2)

(121) 4-[(3-Methylphenyl)amino]-6-(N-(trans-4-hydroxycyclohexyl)-N-methyl-amino)-pyrimido[5,4-d]pyrimidine
Melting point: 220°–222° C.

$R_f$ value: 0.40 (silica gel; petroleum ether/ethyl acetate/methanol=10:8:2)

(122) 4-[(3-Methylphenyl)amino]-6-(1-hydroxy-2-methyl-2-propylamino)-pyrimido[5,4-d]pyrimidine
Melting point: 207°–210° C.

$R_f$ value: 0.47 (silica gel; ethyl acetate/methanol=20:1) Calculated: C 62.95 H 6.21 N 25.91 Found: 63.16 6.38 25.41

(123) 4-[(3-Methylphenyl)amino]-6-(cis-2,6-dimethylmorpholino)-pyrimido[5,4-d]pyrimidine
Melting point: 134°–139° C.

$R_f$ value: 0.70 (silica gel; petroleum ether/ethyl acetate/methanol=10:8:2) Calculated: C 65.12 H 6.33 N 23.98 Found: 65.05 6.41 24.06

(124) 4-[(3-Methylphenyl)amino]-6-(trans-2,6-dimethylmorpholino)-pyrimido[5,4-d]pyrimidine (125) 4-[(3-Methylphenyl)amino]-6-(3-methyl-morpholino)-pyrimido[5,4-d]pyrimidine (126) 4-[(3-Methylphenyl)amino]-6-(3,3-dimethylmorpholino)-pyrimido[5,4-d]pyrimidine (127) 4-[(3-Methylphenyl)amino]-6-(3,5-dimethylmorpholino)-pyrimido[5,4-d]pyrimidine (128) 4-[(3-Methylphenyl)amino]-6-(2-methyl-1-piperidinyl)-pyrimido[5,4-d]pyrimidine
Melting point: 131°–134° C.

$R_f$ value: 0.66 (silica gel; petroleum ether/ethyl acetate/methanol=10:5:1) Calculated: C 68.24 H 6.63 N 25.13 Found: 68.25 6.72 24.68

(129) 4-[(3-Chloro-4-fluoro-phenyl)amino]-6-[2-(morpholino)-ethylamino]-pyrimido[5,4-d]pyrimidine
Melting point: 148°–150° C.

$R_f$ value: 0.48 (silica gel; petroleum ether/ethyl acetate/methanol=10:10:3) Calculated: C 53.53 H 4.74 N 24.27 Found: 53.13 4.83 24.00

(130) 4-[(3-Methylphenyl)amino]-6-(2-hydroxy-cyclohexylamino]-pyrimido[5,4-d]pyrimidine
Melting point: 218°–220° C.

$R_f$ value: 0.36 (silica gel; petroleum ether/ethyl acetate/methanol=10:10:2)

(131) 4-[(3-Methylphenyl)amino]-6-(2-methyl-1-pyrrolidinyl)-pyrimido[5,4-d]pyrimidine (132) 4-[(3-Methylphenyl)amino]-6-(2,2-dimethyl-1-pyrrolidinyl)-pyrimido[5,4-d]pyrimidine (133) 4-[(3-Methylphenyl)amino]-6-(2,5-dimethyl-1-pyrrolidinyl)-pyrimido[5,4-d]pyrimidine
Melting point: 123°–125° C.

$R_f$ value: 0.55 (silica gel; petroleum ether/ethyl acetate 10:4)

(134) 4-[(3-Methylphenyl)amino]-6-[trans-4-carboxy-cyclohexylamino]-pyrimido[5,4-d]pyrimidine
Prepared from compound 135 of Example 1 by reaction with methanolic sodium hydroxide solution.
Melting point: >325° C.
Mass spectrum: M$^+$=378

(135) 4-[(3-Methylphenyl)amino]-6-[trans-4-(methoxycarbonylcyclohexylamino]-pyrimido[5,4-d]pyrimidine
Melting point: 170°–174° C.

$R_f$ value: 0.31 (silica gel; petroleum ether/ethyl acetate= 3:5)

(136) 4-[(3-Methylphenyl)amino]-6-[trans-4-aminocarbonylcyclohexylamino]-pyrimido[5,4-d]pyrimidine
Prepared from compound 134 of Example 1 by reaction with thionyl chloride and ammonia.
Melting point: 312°–315° C.

$R_f$ value: 0.38 (silica gel; petroleum ether/ethyl acetate/methanol=10:8:3)

(137) 4-[(3-Methylphenyl)amino]-6-[trans-4-(N-methylaminocarbonyl)cyclohexylamino]-pyrimido[5,4-d]pyrimidine Prepared from compound 134 of Example 1 by reaction with thionyl chloride and methylamine.

Melting point: 298°–304° C.

$R_f$ value: 0.43 (silica gel; petroleum ether/ethyl acetate/methanol=10:8:3)

(138) 4-[(3-Methylphenyl)amino]-6-[trans-4-(N,N-dimethylaminocarbonyl)cyclohexylamino]-pyrimido[5,4-d]pyrimidine Prepared from compound 135 of Example 1 by reaction with O-(benzotriazol-1-yl)-N,N,N',N'-tetramethyluronium tetrafluoroborate, triethylamine and dimethylamine.

Melting point: 214°–217° C.

$R_f$ value: 0.40 (silica gel; petroleum ether/ethyl acetate/methanol=10:8:3)

Mass spectrum: $M^+=405$ (139) 4-[(3-Methylphenyl)amino]-6-[trans-4-(pyrrolidinocarbonyl)cyclohexylamino]-pyrimido[5,4-d]pyrimidine Prepared from compound 135 of Example 1 by reaction with O-(benzotriazol-1-yl)-N,N,N',N'-tetramethyluronium tetrafluoroborate, triethylamine and pyrrolidine.

Melting point: 210°–214° C.

$R_f$ value: 0.47 (silica gel; petroleum ether/ethyl acetate/methanol=10:8:3)

Mass spectrum: $M^+=431$ (140) 4-[(3-Methylphenyl)amino]-6-[trans-4-(morpholinocarbonyl)cyclohexylamino]-pyrimido[5,4-d]pyrimidine Prepared from compound 135 of Example i by reaction with N,N'-carbonyldiimidazole and morpholine.

Melting point: 150°–160° C.

$R_f$ value: 0.48 (silica gel; petroleum ether/ethyl acetate/methanol=10:8:3)

Mass spectrum: $M^+=447$ (141) 4-[(3-Methylphenyl)amino]-6-[trans-4-(hydroxymethyl)cyclohexylamino]-pyrimido[5,4-d]pyrimidine Prepared from the compounds of Examples 2 and X.

Melting point: 264°–267° C.

$R_f$ value: 0.41 (silica gel; petroleum ether/ethyl acetate/methanol=10:8:2)

Mass spectrum: $M^+=364$ (142) 4-[(3-Methylphenyl)amino]-6-(4-piperidinyl-amino)-pyrimido[5,4-d]pyrimidine Prepared from compound 194 of Example 1 by reaction with palladium hydroxide and hydrogen to split off the benzyl group. The partly hydrogenated pyrimidopyrimidine parent substance is reformed by subsequent treatment with palladium-on-charcoal in a boiling dioxane/water mixture.

Melting point: 187°–192° C.

$R_f$ value: 0.56 (aluminium oxide; methylene chloride/methanol=20:1.6)

Mass spectrum: $M^+=335$ (143) 4-[(3-Methylphenyl)amino]-6-[(1-formyl-4-piperidinyl)amino]-pyrimido[5,4-d]pyrimidine (144) 4-[(3-Methylphenyl)amino]-6-[(1-acetyl-4-piperidinyl)amino]-pyrimido[5,4-d]pyrimidine Prepared from compound 142 of Example 1 by reaction with acetic anhydride and triethylamine.

Melting point: 174°–177° C.

$R_f$ value: 0.48 (silica gel; methylene chloride/methanol=10:1)

(145) 4-[(3-Methylphenyl)amino]-6-[(1-methylsulfonyl-4-piperidinyl)amino]-pyrimido[5,4-d]pyrimidine Prepared from compound 142 of Example 1 by reaction with methylsulfonyl chloride and triethylamine.

Melting point: 229°–233° C.

$R_f$ value: 0.59 (silica gel; methylene chloride/methanol=10:1)

(146) 4-[(3-Methylphenyl)amino]-6-[(1-methoxycarbonyl-4-piperidinyl)amino]-pyrimido[5,4-d]pyrimidine Prepared from compound 142 of Example 1 by reaction with methyl chloroformate and triethylamine.

Melting point: 141°–146° C.

$R_f$ value: 0.45 (silica gel; methylene chloride/methanol=20:1)

(147) 4-[(3-Methylphenyl)amino]-6-[(1-cyano-4-piperidinyl)amino]-pyrimido[5,4-d]pyrimidine (148) 4-[(3-Methylphenyl)amino]-6-[(1-aminocarbonyl-4-piperidinyl)amino]-pyrimido[5,4-d]pyrimidine (149) 4-[(3-Methylphenyl)amino]-6-[(1-(N-methylamino)carbonyl-4-piperidinyl)amino]-pyrimido[5,4-d]pyrimidine (150) 4-[(3-Methylphenyl)amino]-6-[(1-(N,N-dimethylamino)carbonyl-4-piperidinyl)amino]-pyrimido[5,4-d]pyrimidine (151) 4-[(3-Methylphenyl)amino]-6-(4-methoxycarbonyl-1-piperidinyl)-pyrimido[5,4-d]pyrimidine Prepared from compound 46 of Example 1 by reaction with thionyl chloride and methanol.

Melting point: 114°–118° C.

$R_f$ value: 0.50 (silica gel; petroleum ether/ethyl acetate/methanol=10:5:1)

Mass spectrum: $M^+=378$ (152) 4-[(3-Methylphenyl)amino]-6-[4-(N-methylamino)carbonyl-1-piperidinyl]-pyrimido[5,4-d]pyrimidine Prepared from compound 46 of Example 1 by reaction with O-(benzotriazol-1-yl)-N,N,N',N'-tetramethyluronium tetrafluoroborate, triethylamine and methylamine.

Melting point: 226°–230° C.

$R_f$ value: 0.43 (silica gel; petroleum ether/ethyl acetate/methanol=10:8:3)

Mass spectrum: $M^+=377$ (153) 4-[(3-Methylphenyl)amino]-6-[4-(N,N-dimethylamino)carbonyl-1-piperidinyl]-pyrimido[5,4-d]pyrimidine Prepared from compound 46 of Example 1 by reaction with O-(benzotriazol-1-yl)-N,N,N',N'-tetramethyluronium tetrafluoroborate, triethylamine and dimethylamine.

Melting point: 174°–177° C.

$R_f$ value: 0.53 (silica gel; petroleum ether/ethyl acetate/methanol=10:8:4)

(154) 4-[(3-Methylphenyl)amino]-6-[4-(pyrrolidino)carbonyl-1-piperidinyl]-pyrimido[5,4-d]pyrimidine Prepared from compound 46 of Example 1 by reaction with O-(benzotriazol-1-yl)-N,N,N',N'-tetramethyluronium tetrafluoroborate, triethylamine and pyrrolidine.

Melting point: 181°–184° C.

$R_f$ value: 0.46 (silica gel; petroleum ether/ethyl acetate/methanol=10:8:3)

Mass spectrum: $M^+=417$ (155) 4-[(3-Methylphenyl)amino]-6-[4-hydroxymethyl-1-piperidinyl]-pyrimido[5,4-d]pyrimidine Melting point: 170°–175° C.

$R_f$ value: 0.55 (silica gel; petroleum ether/ethyl acetate/methanol=10:7:1.5) Calculated: C 65.12 H 6.33 N 23.98 Found: 65.07 6.52 23.80

(156) 4-[(3-Methylphenyl)amino]-6-[3-hydroxymethyl-1-piperidinyl]-pyrimido[5,4-d]pyrimidine Melting point: 141°–145° C.

$R_f$ value: 0.50 (silica gel; petroleum ether/ethyl acetate/methanol=10:8:2) Calculated: C 65.12 H 6.33 N 23.98 Found: 64.96 6.47 23.88

(157) 4-[(3-Methylphenyl)amino]-6-[2-hydroxymethyl-1-piperidinyl]-pyrimido[5,4-d]pyrimidine
Melting point: 164°–168° C.
$R_f$ value: 0.40 (silica gel; petroleum ether/ethyl acetate=1:1) Calculated: C 65.12 H 6.33 N 23.98 Found: 64.94 6.22 24.00

(158) 4-[(3-Methylphenyl)amino]-6-(n-propylamino)-pyrimido[5,4-d]pyrimidine
Melting point: 145°–149° C.
$R_f$ value: 0.76 (silica gel; petroleum ether/ethyl acetate/methanol=10:8:2) Calculated: C 65.29 H 6.16 N 28.55 Found: 64.40 6.33 28.13

(159) 4-[(3-Methylphenyl)amino]-6-(n-butylamino)-pyrimido[5,4-d]pyrimidine
Melting point: 136°–140° C.
$R_f$ value: 0.53 (silica gel; petroleum ether/ethyl acetate/methanol=10:8:2)
Mass spectrum: M⁺=308 Calculated: C 66.21 H 6.54 N 27.25 Found: 65.96 6.65 27.05

(160) 4-[(3-Methylphenyl)amino]-6-(3-phenyl-n-propylamino)pyrimido[5,4-d]pyrimidine
Melting point: 118°–122° C.
$R_f$ value: 0.66 (silica gel; petroleum ether/ethyl acetate/methanol=10:8:2)
Mass spectrum: M⁺=370 Calculated: C 71.33 5.99 N 22.68 Found: 71.48 6.06 22.69

(161) 4-[(3-Methylphenyl)amino]-6-[4-hydroxy-4-phenyl-1-piperidinyl]-pyrimido[5,4-d]pyrimidine
Melting point: 185°–188° C.
$R_f$ value: 0.50 (silica gel; petroleum ether/ethyl acetate/methanol=10:5:1)

(162) 4-[(3-Methylphenyl)amino]-6-[(1-carboxy-1-methyl]ethylamino]-pyrimido[5,4-d]pyrimidine (163) 4-[(3-Methylphenyl)amino]-6-[(1-methoxycarbonyl-1-methyl)ethylamino]-pyrimido[5,4-d]pyrimidine (164) 4-[(3-Methylphenyl)amino]-6-[(1-aminocarbonyl-1-methyl)ethylamino]-pyrimido[5,4-d]pyrimidine (165) 4-[(3-Methylphenyl)amino]-6-[(1-(N-methylamino)carbonyl-1-methyl)ethylamino]-pyrimido[5,4-d]pyrimidine
Melting point: 214°–216° C.
$R_f$ value: 0.41 (silica gel; petroleum ether/ethyl acetate/methanol=10:10:3)
Mass spectrum: M⁺=351

(166) 4-[(3-Methylphenyl)amino]-6-[(1-(N,N-dimethylamino)carbonyl-1-methyl)ethylamino]-pyrimido[5,4-d]pyrimidine (167) 4-[(3-Methylphenyl)amino]-6-[(1-(1-pyrrolidino)carbonyl-1-methyl)ethylamino]-pyrimido[5,4-d]pyrimidine (168) 4-[(3-Methylphenyl)amino]-6-[(1-(morpholino)carbonyl-1-methyl)ethylamino]-pyrimido[5,4-d]pyrimidine (169) 4-[(3-Methylphenyl)amino]-6-(3-tetrahydrofuranylamino)-pyrimido[5,4-d]pyrimidine (170) 4-[(3-Methylphenyl)amino]-6-(4-tetrahydropyranylamino)-pyrimido[5,4-d]pyrimidine
Melting point: 226°–228° C.
$R_f$ value: 0.46 (silica gel; petroleum ether/ethyl acetate/methanol=10:10:1) Calculated: C 64.26 5.99 N 24.98 Found: 64.03 5.99 24.28

(171) 4-[(3-Methylphenyl)amino]-6-(tetrahydrofurfurylamino)-pyrimido[5,4-d]pyrimidine (172) 4-[(3-Methylphenyl)amino]-6-[(1-(2-hydroxyethyl)aminocarbonyl-1-methyl)ethylamino]-pyrimido[5,4-d]pyrimidine (173) 4-[(3-Methylphenyl)amino]-6-[(1-deoxy-1-D-sorbityl)amino]-pyrimido[5,4-d]pyrimidine
Melting point: 179°–182° C.
$R_f$ value: 0.45 (silica gel; petroleum ether/ethyl acetate=1:2) Calculated: C 54.79 H 5.81 N 20.18 Found: 54.69 5.84 20.38

(174) 4-[(3-Methylphenyl)amino]-6-(p-hydroxyphenylamino)-pyrimido[5,4-d]pyrimidine (175) 4-[(3-Methylphenyl)amino]-6-[(trans-4-(N-oxido-N,N-dimethylamino)-cyclohexyl)-amino]-pyrimido[5,4-d]pyrimidine
Melting point: 182°–184° C.
$R_f$ value: 0.55 (silica gel; petroleum ether/ethyl acetate/methanol=10:10:4)
Prepared from compound 116 of Example 1 by reaction with hydrogen peroxide.

(176) 4-[(3-Methylphenyl)amino]-6-[(1-methyl-N-oxido-4-piperidinyl)-amino]-pyrimido[5,4-d]pyrimidine
Melting point: 212°–214° C.
$R_f$ value: 0.53 (aluminium oxide; petroleum ether/ethyl acetate/methanol=2:8:3)
Prepared from compound 62 of Example 1 by reaction with hydrogen peroxide.

(177) 4-[(3-Methylphenyl)amino]-6-(4-oxo-1-piperidinyl)-pyrimido[5,4-d]pyrimidine
Prepared from compound 31 of Example 1 by reaction with pyridinium dichromate.
Melting point: 122°–124° C.
$R_f$ value: 0.40 (aluminium oxide; petroleum ether/ethyl acetate=1:1)

(178) 4-[(3-Methylphenyl)amino]-6-[2-(2-hydroxyethyloxy)ethylamino]-pyrimido[5,4-d]pyrimidine
Melting point: 99°–101° C. Calculated: C 59.98 H 5.92 N 24.68 Found: 59.75 6.01 24.56

(179) 4-[(3-Methylphenyl)amino]-6-(2,3-dihydroxypropylamino)-pyrimido[5,4-d]pyrimidine
Melting point: 187°–189° C.
$R_f$ value: 0.39 (silica gel; petroleum ether/ethyl acetate/methanol=10:10:2) Calculated: C 58.88 5.56 N 25.75 Found: 58.85 5.60 25.50

(180) 4-[(3-Methylphenyl)amino]-6-[4-(2-oxo-1-pyrrolidinyl)-phenylamino]-pyrimido[5,4-d]pyrimidine
Melting point: 212°–214° C.
$R_f$ value: 0.42 (silica gel; petroleum ether/ethyl acetate/methanol=10:10:2)
Mass spectrum: M⁺=303

(181) 4-(Phenylamino)-6-(phenylamino)-pyrimido[5,4-d]pyrimidine (182) 4-[N-Methyl-N-phenyl-amino]-6-[N-methyl-N-phenylamino]-pyrimido[5,4-d]pyrimidine (183) 4-[(4-Chloro-3-fluoro-phenyl)amino]-6-(1,3-dihydroxy-2-methyl-2-propylamino)-pyrimido[5,4-d]pyrimidine
Melting point: >230° C.
$R_f$ value: 0.30 (silica gel; petroleum ether/ethyl acetate/methanol=10:10:3)
Mass spectrum: M⁺=378/380

(184) 4-[(3-Methylphenyl)amino]-6-[4-(morpholino)carbonyl-1-piperidinyl]-pyrimido[5,4-d]pyrimidine
Prepared from compound 46 of Example 1 by reaction with N,N'-carbonyldiimidazole and morpholine.
Melting point: 208°–212° C.
$R_f$ value: 0.58 (silica gel; petroleum ether/ethyl acetate/methanol=10:8:4)
Mass spectrum: M⁺=433

(185) 4-[(3-Methylphenyl)amino]-6-(tris-hydroxymethyl-methylamino)-pyrimido[5,4-d]pyrimidine
Melting point: 222°–224° C.

R_f value: 0.45 (silica gel; petroleum ether/ethyl acetate/methanol=10:5:2) Calculated: C 57.29 H 5.65 N 23.58 Found: 57.12 5.69 23.70

(186) 4-[(3-Methylphenyl)amino]-6-(4-acetylamino-1-piperidinyl)-pyrimido[5,4-d]pyrimidine
Prepared from compound 61 of Example 1 by reaction with triethylamine and acetic anhydride.
Melting point: 225°–230° C.
R_f value: 0.50 (silica gel; methylene chloride/methanol=10:1) Calculated: C 63.64 H 6.14 N 26.00 Found: 63.52 6.18 25.62

(187) 4-[(3-Methylphenyl)amino]-6-(4-methylsulphonylamino-1-piperidinyl)-pyrimido[5,4-d]pyrimidine
Prepared from compound 61 of Example 1 by reaction with triethylamine and methanesulphonyl chloride.
Melting point: 182°–187° C.
R_f value: 0.60 (silica gel; methylene chloride/methanol 10:1)

(188) 4-[(3-Methylphenyl)amino]-6-(4-methoxycarbonylamino-1-piperidinyl)-pyrimido[5,4-d]pyrimidine
Prepared from compound 61 of Example 1 by reaction with triethylamine and methyl chloroformate.
Melting point: 178°–180° C.
R_f value: 0.40 (silica gel; methylene chloride/methanol=10:0.75)

(189) 4-[(3-Methylphenyl)amino]-6-[4-(N,N-dimethylaminocarbonyl)amino-1-piperidinyl)-pyrimido[5,4-d]pyrimidine
Prepared from compound 61 of Example 1 by reaction with triethylamine and N,N-dimethylcarbamoyl chloride.
Melting point: 220°–227° C.
R_f value: 0.53 (silica gel; methylene chloride/methanol=10:1)

(190) 4-[(3-Methylphenyl)amino]-6-(4-cyanoamino-1-piperidinyl)-pyrimido[5,4-d]pyrimidine
Prepared from compound 61 of Example 1 by reaction with cyanogen bromide.
Melting point: 220°–224° C.
R_f value: 0.45 (silica gel; petroleum ether/ethyl acetate/methanol=10:8:3)
Mass spectrum: M$^+$=360

(191) 4-[(3-Methylphenyl)amino]-6-(4-formylamino-1-piperidinyl)-pyrimido[5,4-d]pyrimidine
Prepared from compound 61 of Example 1 by reaction with methyl formate.
Melting point: 196°–198° C.
R_f value: 0.58 (silica gel; methylene chloride/methanol 10:1.5)

(192) 4-[(3-Methylphenyl)amino]-6-(4-isopropylaminocarbonylmethyl-1-piperazinyl)-pyrimido[5,4-d]pyrimidine
Melting point: 146°–151° C.
R_f value: 0.42 (silica gel; petroleum ether/ethyl acetate/methanol=10:8:2)
Mass spectrum: M$^+$=420

(193) 4-[(3-Methylphenyl)amino]-6-[4-(2-hydroxymethyl-1-pyrrolidinyl)phenylamino]-pyrimido[5,4-d]pyrimidine
Prepared from the compounds of Examples 2 and XX.
Melting point: 208°–210° C.
R_f value: 0.50 (silica gel; petroleum ether/ethyl acetate/methanol=10:8:2)

(194) 4-[(3-Methylphenyl)amino]-6-[(1-benzyl-4-piperidinyl)amino]-pyrimido[5,4-d]pyrimidine
Melting point: 143°–145° C.
R_f value: 0.48 (silica gel; petroleum ether/ethyl acetate/methanol=10:8:2)
Mass spectrum: M$^+$=425

(195) 4-[(3-Methylphenyl)amino]-6-[(1-ethoxycarbonyl-4-piperidinyl)amino]-pyrimido[5,4-d]pyrimidine
Melting point: 160°–163° C.
R_f value: 0.46 (silica gel; petroleum ether/ethyl acetate/methanol=10:9:2) Calculated: C 61.90 H 6.18 N 24.06 Found: 61.73 6.23 24.08

(196) 4-[(3-Methylphenyl)amino]-6-[3-(2-oxo-1-pyrrolidinyl)-propylamino]-pyrimido[5,4-d]pyrimidine
Melting point: 118°–120° C.
R_f value: 0.25 (aluminium oxide; petroleum ether/ethyl acetate/methanol=10:10:2)

(197) 4-[(3-Methylphenyl)amino]-6-[2-(1,4,7,10,13-pentaoxacyclopentadecyl)-ethylamino]-pyrimido[5,4-]pyrimidine
Melting point: 145°–147° C.
R_f value: 0.37 (aluminium oxide; petroleum ether/ethyl acetate/methanol=10:10:1) Calculated: C 59.48 H 6.65 N 17.34 Found: 59.56 6.69 17.28

(198) 4-[(3-Methylphenyl)amino]-6-[2-(1,4,7,10,13,16-hexaoxacyclooctadecyl)-ethylamino]-pyrimido[5,4-d]pyrimidine
Melting point: 72°–74° C.
R_f value: 0.29 (aluminium oxide; petroleum ether/ethyl acetate/methanol=10:10:1)

(199) 4-[(2-Cyclopropylphenyl)amino]-6-morpholino-pyrimido[5,4-d]pyrimidine
Melting point: 171°–173° C. Calculated: C 65.49 H 5.78 N 24.12 Found: 65.24 5.84 24.06

(200) 4-[(3-Methylphenyl)amino]-6-[4-(2-hydroxyethyl)-1-piperazinyl]-pyrimido[5,4-d]pyrimidine
Melting point: 140°–142° C.
R_f value: 0.45 (aluminium oxide; petroleum ether/ethyl acetate/methanol=10:10:1)

(201) 4-[(4-Amino-3-cyano-phenyl)amino]-6-[(trans-4-hydroxycyclohexyl)-amino]-pyrimido[5,4-d]pyrimidine
Melting point: 200° C.
R_f value: 0.44 (silica gel; petroleum ether/ethyl acetate/methanol=10:10:3)

(202) 4-[(3,4-Dichlorophenyl)amino]-6-[(trans-4-hydroxycyclohexyl)-amino]-pyrimido[5,4-d]pyrimidine
Melting point: 220°–222° C.
R_f value: 0.57 (aluminium oxide; petroleum ether/ethyl acetate/methanol=10:10:1)

(203) 4-[(3-Chloro-4-methoxy-phenyl)amino]-6-[(trans-4-hydroxycyclohexyl)-amino]-pyrimido[5,4-d]pyrimidine
Melting point: 197°–199° C.
R_f value: 0.40 (aluminium oxide; petroleum ether/ethyl acetate/methanol=10:10:2) Calculated: C 56.92 H 5.28 N 20.96 Found: 56.71 5.29 20.54

(204) 4-[(3-Chloro-4-fluoro-phenyl)amino]-6-[(trans-4-hydroxycyclohexyl)-amino]-pyrimido[5,4-d]pyrimidine
Melting point: 222°–224° C. Calculated: C 55.60 H 4.66 N 21.61 Found: 55.40 4.75 21.35

(205) 4-[(4-Amino-3-nitro-phenyl)amino]-6-[(trans-4-hydroxycyclohexyl)-amino]-pyrimido[5,4-d]pyrimidine
Melting point: 250°–252° C.
R_f value: 0.32 (silica gel; petroleum ether/ethyl acetate/methanol=10:10:2)

(206) 4-[(4-Chloro-3-nitro-phenyl)amino]-6-[(trans-4-hydroxycyclohexyl)-amino]-pyrimido[5,4-d]pyrimidine
Melting point: 235°–237° C.
R_f value: 0.28 (silica gel; petroleum ether/ethyl acetate/methanol=10:10:3) Calculated: C 51.99 H 4.36 N 23.57 Found: 51.70 4.45 23.78

(207) 4-[(4-Amino-3,5-dichloro-phenyl)amino]-6-[(trans-4-hydroxycyclohexyl)-amino]-pyrimido[5,4-d]pyrimidine Melting point: 250°–252° C.

$R_f$ value: 0.23 (silica gel; petroleum ether/ethyl acetate/methanol=10:10:3) Calculated: C 51.43 H 4.55 N 23.32 Found: 51.55 4.70 23.35

(208) 4-[(3-Methylphenyl)amino]-6-butyloxy-pyrimido[5,4-d]pyrimidine

Melting point: 54°–56° C.

$R_f$ value: 0.67 (silica gel; petroleum ether/ethyl acetate 10:7)

Mass spectrum: M⁺=309

(209) 4-[(3-Methylphenyl)amino]-6-(1,3-dihydroxy-2-propylamino)-pyrimido[5,4-d]pyrimidine Melting point: 170°–172° C.

$R_f$ value: 0.27 (silica gel; petroleum ether/ethyl acetate/methanol=10:10:3) Calculated: C 58.88 5.55 N 25.75 Found: 58.65 5.57 25.80

(210) 4-[(3-Chloro-4-fluoro-phenyl)amino]-6-[(2-hydroxy-1-phenyl)-1-ethylamino]-pyrimido[5,4-d]pyrimidine (211) 4-[(3-Chloro-4-fluoro-phenyl)amino]-6-[(2-hydroxy-2-phenyl)-1-ethylamino]-pyrimido[5,4-d]pyrimidine (212) 4-[(3-Chloro-4-fluoro-phenyl)amino]-6-[(1-hydroxy-3-phenyl)-2-propylamino]-pyrimido[5,4-d]pyrimidine (213) 4-[(3-Chloro-4-fluoro-phenyl)amino]-6-[(1-hydroxy-1-phenyl)-2-propylamino]-pyrimido[5,4-d]pyrimidine Melting point: 234°–236° C.

$R_f$ value: 0.42 (silica gel; petroleum ether/ethyl acetate/methanol=10:10:1)

Mass spectrum: M⁺=424

(214) 4-[(3-Chloro-4-fluoro-phenyl)amino]-6-[(1,3-dihydroxy-1-phenyl)-2-propylamino]-pyrimido[5,4-d]pyrimidine Melting point: 176°–178° C.

$R_f$ value: 0.48 (silica gel; petroleum ether/ethyl acetate/methanol=10:10:2)

(215) 4-[(3-Chloro-4-fluoro-phenyl)amino]-6-[(1,3-dihydroxy-1-(4-nitrophenyl))-2-propylamino]-pyrimido[5,4-d]pyrimidine (216) 4-[(3-Chloro-4-fluoro-phenyl)amino]-6-[(1-hydroxy-3-methoxy-1-phenyl)-2-propylamino]-pyrimido[5,4-d]pyrimidine (217) 4-[(3-Chloro-4-fluoro-phenyl)amino]-6-[(1-hydroxy-3-methyl)-2-butylamino]-pyrimido[5,4-d]pyrimidine (218) 4-[(3-Chloro-4-fluoro-phenyl)amino]-6-[1-(hydroxymethyl)-cyclopentylamino]-pyrimido[5,4-d]pyrimidine (219) 4-[(3-Chloro-4-fluoro-phenyl)amino]-6-[(2-hydroxy-2-(3-hydroxyphenyl))-1-ethylamino]-pyrimido[5,4-d]pyrimidine (220) 4-[(3-Chloro-4-fluoro-phenyl)amino]-6-[(2-hydroxy-2-(4-hydroxyphenyl))-1-ethylamino]-pyrimido[5,4-d]pyrimidine (221) 4-[(3-Chloro-4-fluoro-phenyl)amino]-6-[(1-hydroxy-1-(4-hydroxyphenyl))-2-propylamino]-pyrimido[5,4-d]pyrimidine (222) 4-[(3-Chloro-4-fluoro-phenyl)amino]-6-[tris-(3-hydroxypropyl)-methylamino]-pyrimido[5,4-d]pyrimidine (223) 4-[(3-Chloro-4-fluoro-phenyl)amino]-6-[N-methyl-N-(2-hydroxyethyl)amino]-pyrimido[5,4-d]pyrimidine (224) 4-[(3-Chloro-4-fluoro-phenyl)amino]-6-[3-carboxy-1-propylamino]-pyrimido[5,4-d]pyrimidine (225) 4-[(3-Chloro-4-fluoro-phenyl)amino]-6-[3-aminocarbonyl-1-propylamino]-pyrimido[5,4-d]pyrimidine (226) 4-[(3-Chloro-4-fluoro-phenyl)amino]-6-[3-(N-methylaminocarbonyl)-1-propylamino]-pyrimido[5,4-d]pyrimidine (227) 4-[(3-Chloro-4-fluoro-phenyl)amino]-6-[3-(N,N-dimethylaminocarbonyl)-1-propylamino]-pyrimido[5,4-d]pyrimidine (228) 4-[(3-Chloro-4-fluoro-phenyl)amino]-6-[3-(N-formylamino)-1-propylamino]-pyrimido[5,4-d]pyrimidine (229) 4-[(3-Chloro-4-fluoro-phenyl)amino]-6-[3-(methoxycarbonylamino)-1-propylamino]-pyrimido[5,4-d]pyrimidine (230) 4-[(3-Chloro-4-fluoro-phenyl)amino]-6-[2-(N-acetylamino)-1-ethylamino]-pyrimido[5,4-d]pyrimidine (231) 4-[(3-Chloro-4-fluoro-phenyl)amino]-6-[3-amino-2-hydroxy-1-propylamino]-pyrimido[5,4-d]pyrimidine (232) 4-[(3-Chloro-4-fluoro-phenyl)amino]-6-[3-(morpholino)-1-propylamino]-pyrimido[5,4-d]pyrimidine (233) 4-[(3-Chloro-4-fluoro-phenyl)amino]-6-[2-(1-piperazinyl)-1-ethylamino]-pyrimido[5,4-d]pyrimidine (234) 4-[(3-Chloro-4-fluoro-phenyl)amino]-6-[2-(1-pyrrolidinyl)-1-ethylamino]-pyrimido[5,4-d]pyrimidine (235) 4-[(3-Chloro-4-fluoro-phenyl)amino]-6-[3-hydroxymethyl-1-piperidinyl]-pyrimido[5,4-d]pyrimidine (236) 4-[(3-Chloro-4-fluoro-phenyl)amino]-6-[(trans-4-(methoxycarbonyl-methyloxy)cyclohexyl)-amino-pyrimido[5,4-d]pyrimidine Prepared from the compounds of Examples 2 and XXVI.

$R_f$ value: 0.32 (silica gel; petroleum ether/ethyl acetate/methanol=10:10:1)

Mass spectrum: M⁺=460

(237) 4-[(3-Chloro-4-fluoro-phenyl)amino]-6-[(trans-4-(carboxy-methyloxy)cyclohexyl)-amino]-pyrimido[5,4-d]pyrimidine Prepared from compound 236 of Example 1 by reaction with sodium hydroxide in a methanol/tetrahydrofuran mixture.

Melting point: 263°–265° C.

$R_f$ value: 0.42 (silica gel; petroleum ether/ethyl acetate/methanol=10:10:3)

Mass spectrum: M⁺=446

(238) 4-[(3-Chloro-4-fluorophenyl)amino]-6-[(trans-4-(N,N-dimethylaminocarbonyl-methyloxy)cyclohexyl)-amino]-pyrimido[5,4-d]pyrimidine (239) 4-[(3-Chloro-4-fluoro-phenyl)amino]-6-[(trans-4-(morpholinocarbonyl-methyloxy)cyclohexyl)-amino]-pyrimido[5,4-d]pyrimidine (240) 4-[(3-Chloro-4-fluoro-phenyl)amino]-6-[(trans-4-(2-methoxycarbonyl-ethyl)cyclohexyl)-amino]-pyrimido[5,4-d]pyrimidine Prepared from the compounds of Examples 2 and XXIII.

Melting point: 144°–146° C.

$R_f$ value: 0.62 (silica gel; petroleum ether/ethyl acetate/methanol=10:10:1)

(241) 4-[(3-Chloro-4-fluoro-phenyl)amino]-6-[(trans-4-(2-carboxy-ethyl)cyclohexyl)-amino]-pyrimido[5,4-d]pyrimidine Prepared from compound 240 of Example 1 by reaction with sodium hydroxide in a methanol/tetrahydrofuran mixture.

Melting point: 298°–300° C.

$R_f$ value: 0.25 (silica gel; petroleum ether/ethyl acetate/methanol=10:10:2)

(242) 4-[(3-Chloro-4-fluoro-phenyl)amino]-6-[(trans-4-(2-N,N-dimethylaminocarbonyl-ethyl)cyclohexyl)-amino]-pyrimido[5,4-d]pyrimidine (243) 4-[(3-Chloro-4-fluoro-phenyl)amino]-6-[(trans-4-(2-morpholinocarbonyl-ethyl)cyclohexyl)-amino]-pyrimido[5,4-d]pyrimidine (244) 4-[(3-Chloro-4-fluoro-phenyl)amino]-6-[(trans-4-(methoxycarbonyl)cyclohexyl-methyl)-amino]-pyrimido[5,4-d]pyrimidine
Prepared from the compounds of Examples 2 and XXVII.
Melting point: 200°–202° C.
$R_f$ value: 0.63 (silica gel; petroleum ether/ethyl acetate/methanol=10:10:1)
Mass spectrum: $M^+$=444

(245) 4-[(3-Chloro-4-fluoro-phenyl)amino]-6-[(trans-4-carboxy-cyclohexyl-methyl)-amino]-pyrimido[5,4-d]pyrimidine
Prepared from compound 244 of Example 1 by reaction with sodium hydroxide in a methanol/tetrahydrofuran mixture.
Melting point: 269°–271° C.
$R_f$ value: 0.58 (silica gel; petroleum ether/ethyl acetate/methanol=10:10:3)
Mass spectrum: $M^+$=430

(246) 4-[(3-Chloro-4-fluoro-phenyl)amino]-6-[(trans-4-(N,N-di-methylamino-carbonyl)cyclohexyl-methyl)-amino]-pyrimido[5,4-d]pyrimidine (247) 4-[(3-Chloro-4-fluoro-phenyl)amino]-6-[(trans-4-(morpholinocarbonyl)cyclohexyl-methyl)-amino]-pyrimido[5,4-d]pyrimidine (248) 4-[(3-Chloro-4-fluoro-phenyl)amino]-6-isopropoxypyrimido[5,4-d]pyrimidine
Melting point: 125°–127° C.
$R_f$ value: 0.42 (silica gel; petroleum ether/ethyl acetate=10:5)
Mass spectrum: $M^+$=333

(249) 4-[(3-Chloro-4-fluoro-phenyl)amino]-6-(4-tetrahydropyranyloxy)-pyrimido[5,4-d]pyrimidine (250) 4-[(3-Chloro-4-fluoro-phenyl)amino]-6-(3-tetrahydrofuranyloxy)-pyrimido[5,4-d]pyrimidine (251) 4-[(3-Chloro-4-fluoro-phenyl)amino]-6-[trans-4-hydroxycyclohexyloxy]-pyrimido[5,4-d]pyrimidine
Melting point: 200°–202° C.
$R_f$ value: 0.35 (silica gel; petroleum ether/ethyl acetate/methanol=10:10:1)
Mass spectrum: $M^+$=362

(252) 4-[(3-Chloro-4-fluoro-phenyl)amino]-6-(2-tetrahydropyranyl-methyloxy)-pyrimido[5,4-d]pyrimidine (253) 4-[(3-Chloro-4-fluoro-phenyl)amino]-6-[trans-4-(methoxycarbonyl)-cyclohexyloxy]-pyrimido[5,4-d]pyrimidine (254) 4-[(3-Chloro-4-fluoro-phenyl)amino]-6-[trans-4-carboxy-cyclohexyloxy]-pyrimido[5,4-d]pyrimidine (255) 4-[(3-Chloro-4-fluoro-phenyl)amino]-6-[trans-4-(N,N-di-methylaminocarbonyl)-cyclohexyloxy]-pyrimido[5,4-d]pyrimidine (256) 4-[(3-Chloro-4-fluoro-phenyl)amino]-6-[trans-4-(N-methylaminocarbonyl)-cyclohexyloxy]-pyrimido[5,4-d]pyrimidine (257) 4-[(3-Chloro-4-fluoro-phenyl)amino]-6-[trans-4-(aminocarbonyl)-cyclohexyloxy]-pyrimido[5,4-d]pyrimidine (258) 4-[(3-Chloro-4-fluoro-phenyl)amino]-6-[trans-4-(N,N-di-methylamino)-cyclohexyloxy]-pyrimido[5,4-d]pyrimidine (259) 4-[(3-Chloro-4-fluoro-phenyl)amino]-6-[trans-4-(N-acetylamino)-cyclohexyloxy]-pyrimido[5,4-d]pyrimidine (260) 4-[(3-Chloro-4-fluoro-phenyl)amino] methylsulphonylamino)-cyclohexyloxy]-pyrimido[5,4-d]pyrimidine (261) 4-[(3-Chloro-4-fluoro-phenyl)amino]-6-[trans-4-(N-methoxycarbonylamino)-cyclohexyloxy]-pyrimido[5,4-d]pyrimidine (262) 4-[(3-Chloro-4-fluoro-phenyl)amino]-6-[trans-4-(N-tert-butyloxycarbonylamino)-cyclohexyloxy]-pyrimido[5,4-d]pyrimidine (263) 4-[(3-Chloro-4-fluoro-phenyl)amino]-6-[1-methyl-4-piperidinyloxy]-pyrimido[5,4-d]pyrimidine
Melting point: 129°–131° C.
$R_f$ value: 0.48 (aluminium oxide; petroleum ether/ethyl acetate=1:1)
Mass spectrum: $M^+$=389

(264) 4-[(3-Chloro-4-fluoro-phenyl)amino]-6-[1-acetyl-4-piperidinyloxy]-pyrimido[5,4-d]pyrimidine (265) 4-[(3-Chloro-4-fluoro-phenyl)amino]-6-[1-methylsulfonyl-4-piperidinyloxy]-pyrimido[5,4-d]pyrimidine (266) 4-[(3-Chloro-4-fluoro-phenyl)amino]-6-[1-tert-butyloxycarbonyl-4-piperidinyloxy]-pyrimido[5,4-d]pyrimidine (267) 4-[(3-Chloro-4-fluoro-phenyl)amino]-6-[1-methoxycarbonyl-4-piperidinyloxy]-pyrimido[5,4-d]pyrimidine (268) 4-[(3-Chloro-4-fluoro-phenyl)amino]-6-[2-methoxyethyloxy]-pyrimido[5,4-d]pyrimidine (269) 4-[(3-Chloro-4-fluoro-phenyl)amino]-6-[2-hydroxyethyloxy]-pyrimido[5,4-d]pyrimidine (270) 4-[(3-Chloro-4-fluoro-phenyl)amino]-6-[1-methoxy-2-propyloxy]-pyrimido[5,4-d]pyrimidine (271) 4-[(3-Chloro-4-fluoro-phenyl)amino]-6-allyloxy-pyrimido[5,4-d]pyrimidine (272) 4-[(3-Chloro-4-fluoro-phenyl)amino]-6-[cyclobutyloxy]-pyrimido[5,4-d]pyrimidine (273) 4-[(3-Chloro-4-fluoro-phenyl)amino]-6-[3-(3-methyloxetanyl)-methyloxy]-pyrimido[5,4-d]pyrimidine (274) 4-[(3-Chloro-4-fluoro-phenyl)amino]-6-[2-tetrahydropyranyl-methyloxy]-pyrimido[5,4-d]pyrimidine (275) 4-[(3-Chloro-4-fluoro-phenyl)amino]-6-[3-hydroxycyclopentyloxy]-pyrimido[5,4-d]pyrimidine (276) 4-[(3-Chloro-4-fluoro-phenyl)amino]-6-[2-hydroxycyclohexyloxy]-pyrimido[5,4-d]pyrimidine (277) 4-[(3-Chloro-4-fluoro-phenyl)amino]-6-[3-hydroxycyclohexyloxy]-pyrimido[5,4-d]pyrimidine (278) 4-[(3-Chloro-4-fluoro-phenyl)amino]-6-[1-N,N-dimethylamino-2-propyloxy]-pyrimido[5,4-d]pyrimidine (279) 4-[(3-Chloro-4-fluoro-phenyl)amino]-6-[2-(morpholino)-ethyloxy]-pyrimido[5,4-d]pyrimidine (280) 4-[(3-Chloro-4-fluoro-phenyl)amino]-6-[1-methyl-3-pyrroidinyloxy]-pyrimido[5,4-d]pyrimidine (281) 4-[(3-Chloro-4-fluoro-phenyl)amino]-6-[1-methyl-3-piperidinyloxy]-pyrimido[5,4-d]pyrimidine (282) 4-[(3-Chloro-4-fluoro-phenyl)amino]-6-[1-methoxy-2-methyl-2-propylamino]-pyrimido[5,4-d]pyrimidine (283) 4-[(3-Chloro-4-fluoro-phenyl)amino]-6-[3-amino-1-pyrrolidinyl]-pyrimido[5,4-d]pyrimidine (284) 4-[(3-Chloro-4-fluoro-phenyl)amino]-6-[3-N,N-dimethylamino-1-pyrrolidinyl]-pyrimido[5,4-d]pyrimidine (285) 4-[(3-Chloro-4-fluoro-phenyl)amino]-6-[3-acetylamino-1-pyrrolidinyl]-pyrimido[5,4-d]pyrimidine (286) 4-[(3-Chloro-4-fluoro-phenyl)amino]-6-[3-cyanoamino-1-pyrrolidinyl]-pyrimido[5,4-d]pyrimidine (287) 4-[(3-Chloro-4-fluoro-phenyl)amino]-6-[3-methylsulphonylamino-1-pyrrolidinyl]-pyrimido[5,4-d]pyrimidine (288) 4-[(3-Chloro-4-fluoro-phenyl)amino]-6-[3-methoxycarbonylamino-1-pyrrolidinyl]-pyrimido[5,4-d]pyrimidine (289) 4-[(3-Chloro-4-fluoro-phenyl)amino]-6-[3-formylamino-1-pyrrolidinyl]-pyrimido[5,4-d]pyrimidine (290) 4-[(3-Chloro-4-fluoro-phenyl)amino]-6-[3-N,N-dimethylaminocarbonylamino-1-pyrrolidinyl]-pyrimido[5,4-d]pyrimidine
(291) 4-[(3-Chloro-4-fluoro-phenyl)amino]-6-[3-amino-1-piperidinyl]-pyrimido[5,4-d]pyrimidine
(292) 4-[(3-Chloro-4-fluoro-phenyl)amino]-6-[3-N,N-dimethylamino-1-piperidinyl]-pyrimido[5,4-d]pyrimidine
(293) 4-[(3-Chloro-4-fluoro-phenyl)amino]-6-[3-acetylamino-1-piperidinyl]-pyrimido[5,4-d]pyrimidine
(294) 4-[(3-Chloro-4-fluoro-phenyl)amino]-6-[3-methoxycarbonylamino-1-piperidinyl]-pyrimido[5,4-d]pyrimidine
(295) 4-[(3-Chloro-4-fluoro-phenyl)amino]-6-[3-methylsulphonylamino-1-piperidinyl]-pyrimido[5,4-d]pyrimidine
(296) 4-[(3-Chloro-4-fluoro-phenyl)amino]-6-[3-pyrrolidinylamino]-pyrimido[5,4-d]pyrimidine
(297) 4-[(3-Chloro-4-fluoro-phenyl)amino]-6-[1-methyl-3-pyrroidinylamino]-pyrimido[5,4-d]pyrimidine
(298) 4-[(3-Chloro-4-fluoro-phenyl)amino]-6-[1-acetyl-3-pyrrolidinylamino]-pyrimido[5,4-d]pyrimidine
(299) 4-[(3-Chloro-4-fluoro-phenyl)amino]-6-[1-cyano-3-pyrrolidinylamino]-pyrimido[5,4-d]pyrimidine
(300) 4-[(3-Chloro-4-fluoro-phenyl)amino]-6-[1-methylsulphonyl-3-pyrrolidinylamino]-pyrimido[5,4-d]pyrimidine
(301) 4-[(3-Chloro-4-fluoro-phenyl)amino]-6-[1-methoxycarbonyl-3-pyrrolidinylamino]-pyrimido[5,4-d]pyrimidine
(302) 4-[(3-Chloro-4-fluoro-phenyl)amino]-6-[1-formyl-3-pyrrolidinylamino]-pyrimido[5,4-d]pyrimidine
(303) 4-[(3-Chloro-4-fluoro-phenyl)amino]-6-[1-(N,N-dimethylaminocarbonyl)-3-pyrrolidinylamino]-pyrimido[5,4-d]pyrimidine
(304) 4-[(3-Chloro-4-fluoro-phenyl)amino]-6-[3-piperidinylamino]-pyrimido[5,4-d]pyrimidine
(305) 4-[(3-Chloro-4-fluoro-phenyl)amino]-6-[1-methyl-3-piperidinylamino]-pyrimido[5,4-d]pyrimidine
(306) 4-[(3-Chloro-4-fluoro-phenyl)amino]-6-[1-acetyl-3-piperidinylamino]-pyrimido[5,4-d]pyrimidine
(307) 4-[(3-Chloro-4-fluoro-phenyl)amino]-6-[1-methoxycarbonyl-3-piperidinylamino]-pyrimido[5,4-d]pyrimidine
(308) 4-[(3-Chloro-4-fluoro-phenyl)amino]-6-[1-methylsulfonyl-3-piperidinylamino]-pyrimido[5,4-d]pyrimidine
(309) 4-[(3-Chloro-4-fluoro-phenyl)amino]-6-[2,5-dimethyl-1-piperazinyl]-pyrimido[5,4-d]pyrimidine
(310) 4-[(3-Chloro-4-fluoro-phenyl)amino]-6-[3-methyl-1-piperazinyl]-pyrimido[5,4-d]pyrimidine
(311) 4-[(3-Chloro-4-fluoro-phenyl)amino]-6-[4-(2-aminoethyl)-1-piperazinyl]-pyrimido[5,4-d]pyrimidine
(312) 4-[(3-Chloro-4-fluoro-phenyl)amino]-6-[4-(2-(2-hydroxyethyloxy)ethyl)-1-piperazinyl]-pyrimido[5,4-d]pyrimidine
(313) 4-[(3-Chloro-4-fluoro-phenyl)amino]-6-[2-butyloxy]-pyrimido[5,4-d]pyrimidine
(314) 4-[(3-Chloro-4-fluoro-phenyl)amino]-6-[trans-4-methoxy-cyclohexyloxy]-pyrimido[5,4-d]pyrimidine
(315) 4-[(3-Chloro-4-fluoro-phenyl)amino]-6-(1,3-dihydroxy-2-propylamino)-pyrimido[5,4-d]pyrimidine
Melting point: 213°–218° C.
$R_f$ value: 0.37 (silica gel; petroleum ether/ethyl acetate=10:8)
(316) 4-[(3,4-Dichloro-phenyl)amino]-6-(1,3-dihydroxy-2-propylamino)-pyrimido[5,4-d]pyrimidine
(317) 4-[(3-Chloro-phenyl)amino]-6-(1,3-dihydroxy-2-propylamino)-pyrimido[5,4-d]pyrimidine
(318) 4-[(3-Bromo-phenyl)amino]-6-(1,3-dihydroxy-2-propylamino)-pyrimido[5,4-d]pyrimidine
(319) 4-[(3-Nitro-phenyl)amino]-6-(1,3-dihydroxy-2-propylamino)-pyrimido[5,4-d]pyrimidine
(320) 4-[(3-Ethynyl-phenyl)amino]-6-(1,3-dihydroxy-2-propylamino)-pyrimido[5,4-d]pyrimidine
(321) 4-[(3,4-Dichloro-phenyl)amino]-6-(1,3-dihydroxy-2-methyl-2-propylamino)-pyrimido[5,4-d]pyrimidine
(322) 4-[(3-Chloro-phenyl)amino]-6-(1,3-dihydroxy-2-methyl-2-propylamino)-pyrimido[5,4-d]pyrimidine
(323)-[(3-Bromo-phenyl)amino]-6-(1,3-dihydroxy-2-methyl-2-propylamino)-pyrimido[5,4-d]pyrimidine
(324) 4-[(3-Nitro-phenyl)amino]-6-(1,3-dihydroxy-2-methyl-2-propylamino)-pyrimido[5,4-d]pyrimidine
(325) 4-[(3-Ethynyl-phenyl)amino]-6-(1,3-dihydroxy-2-methyl-2-propylamino)-pyrimido[5,4-d]pyrimidine
(326) 4-[(3-Methyl-phenyl)amino]-6-(1,3-dihydroxy-2-methyl-2-propylamino)-pyrimido[5,4-d]pyrimidine
(327) 4-[(3-Chloro-4-fluoro-phenyl)amino]-6-(1-hydroxy-2-methyl-2-propylamino)-pyrimido[5,4-d]pyrimidine
Melting point: 255°–259° C.
$R_f$ value: 0.54 (silica gel; ethyl acetate/methanol=20:1)
(328) 4-[(3,4-Dichloro-phenyl)amino]-6-(1-hydroxy-2-methyl-2-propylamino)-pyrimido[5,4-d]pyrimidine
(329) 4-[(3-Chloro-phenyl)amino]-6-(1-hydroxy-2-methyl-2-propylamino)-pyrimido[5,4-d]pyrimidine
(330) 4-[(3-Bromo-phenyl)amino]-6-(1-hydroxy-2-methyl-2-propylamino)-pyrimido[5,4-d]pyrimidine
(331) 4-[(3-Nitro-phenyl)amino]-6-(1-hydroxy-2-methyl-2-propylamino)-pyrimido[5,4-d]pyrimidine
(332) 4-[(3-Ethynyl-phenyl)amino]-6-(1-hydroxy-2-methyl-2-propylamino)-pyrimido[5,4-d]pyrimidine
(333) 4-[(3-Nitro-phenyl)amino]-6-[(trans-4-hydroxycyclohexyl)-amino]-pyrimido[5,4-d]pyrimidine
(334) 4-[(3-Ethynyl-phenyl)amino]-6-[(trans-4-hydroxycyclohexyl)-amino]-pyrimido[5,4-d]pyrimidine
(335) 4-[(3-Chloro-4-fluoro-phenyl)amino]-6-[(4-aminocyclohexyl)amino]-pyrimido[5,4-d]pyrimidine
(336) 4-[(3,4-Dichloro-phenyl)amino]-6-[(trans-4-aminocyclohexyl)amino]-pyrimido[5,4-d]pyrimidine
(337) 4-[(3-Chloro-phenyl)amino]-6-[(trans-4-aminocyclohexyl)amino]-pyrimido[5,4-d]pyrimidine
(338) 4-[(3-Bromo-phenyl)amino]-6-[(trans-4-aminocyclohexyl)amino]-pyrimido[5,4-d]pyrimidine
(339) 4-[(3-Nitro-phenyl)amino]-6-[(trans-4-aminocyclohexyl)amino]-pyrimido[5,4-d]pyrimidine
(340) 4-[(3-Ethynyl-phenyl)amino]-6-[(trans-4-aminocyclohexyl)amino]-pyrimido[5,4-d]pyrimidine
(341) 4-[(3-Chloro-4-fluoro-phenyl)amino]-6-[(trans-4-dimethylaminocyclohexyl)amino]-pyrimido[5,4-d]pyrimidine
(342) 4-[(3,4-Dichloro-phenyl)amino]-6-[(trans-4-dimethylaminocyclohexyl)amino]-pyrimido[5,4-d]pyrimidine
(343) 4-[(3-Chloro-phenyl)amino]-6-[(trans-4-dimethylaminocyclohexyl)amino]-pyrimido[5,4-d]pyrimidine
(344) 4-[(3-Bromo-phenyl)amino]-6-[(trans-4-dimethylaminocyclohexyl)amino]-pyrimido[5,4-d]pyrimidine
(345) 4-[(3-Nitro-phenyl)amino]-6-[(trans-4-dimethylaminocyclohexyl)amino]-pyrimido[5,4-d]pyrimidine
(346) 4-[(3-Ethynyl-phenyl)amino]-6-[(trans-4-dimethylaminocyclohexyl)amino]-pyrimido[5,4-d]pyrimidine (347) 4-[(3-Chloro-4-fluoro-phenyl)amino]-6-[(trans-4-acetylaminocyclohexyl)amino]-pyrimido[5,4-d]pyrimidine
(348) 4-[(3,4-Dichloro-phenyl)amino]-6-[(trans-4-acetylaminocyclohexyl)amino]-pyrimido[5,4-d]pyrimidine
(349) 4-[(3-Chloro-phenyl)amino]-6-[(trans-4-acetylaminocyclohexyl)amino]-pyrimido[5,4-d]pyrimidine
(350) 4-[(3-Bromo-phenyl)amino]-6-[(trans-4-acetylaminocyclohexyl)amino]-pyrimido[5,4-d]pyrimidine
(351) 4-[(3(351) 4-[(3-Nitro-phenyl)amino]-6-acetylaminocyclohexyl)amino]-pyrimido[5,4-d]pyrimidine
(352) 4-[(3-Ethynyl-phenyl)amino]-6-[(trans-4-acetylaminocyclohexyl)amino]-pyrimido[5,4-d]pyrimidine
(353) 4-[(3-Chloro-4-fluoro-phenyl)amino]-6-[(trans-4-methylsulphonylaminocyclohexyl)amino]-pyrimido[5,4-d]pyrimidine
(354) 4-[(3,4-Dichloro-phenyl)amino]-6-[(trans-4-methylsulphonylaminocyclohexyl)amino]-pyrimido[5,4-d]pyrimidine
(355) 4-[(3-Chloro-phenyl)amino]-6-[(trans-4-methylsulphonylaminocyclohexyl)amino]-pyrimido[5,4-d]pyrimidine
(356) 4-[(3-Bromo-phenyl)amino]-6-[(trans-4-methylsulphonylaminocyclohexyl)amino]-pyrimido[5,4-d]pyrimidine
(357) 4-[(3-Nitro-phenyl)amino]-6-[(trans-4-methylsulphonylaminocyclohexyl)amino]-pyrimido[5,4-d]pyrimidine
(358) 4-[(3-Ethynyl-phenyl)amino]-6-[(trans-4-methylsulphonylaminocyclohexyl)amino]-pyrimido[5,4-d]pyrimidine
(359) 4-[(3-Chloro-4-fluoro-phenyl)amino]-6-[(trans-4-methoxycyclohexyl)amino]-pyrimido[5,4-d]pyrimidine
(360) 4-[(3,4-Dichloro-phenyl)amino]-6-[(trans-4-methoxycyclohexyl)amino]-pyrimido[5,4-d]pyrimidine
(361) 4-[(3-Chloro-phenyl)amino]-6-[(trans-4-methoxycyclohexyl)amino]-pyrimido[5,4-d]pyrimidine
(362) 4-[(3-Bromo-phenyl)amino]-6-[(trans-4-methoxycyclohexyl)amino]-pyrimido[5,4-d]pyrimidine
(363) 4-[(3-Nitro-phenyl)amino]-6-[(trans-4-methoxycyclohexyl)amino]-pyrimido[5,4-d]pyrimidine
(364) 4-[(3-Ethynyl-phenyl)amino]-6-[(trans-4-methoxycyclohexyl)amino]-pyrimido[5,4-d]pyrimidine
(365) 4-[(3-Chloro-4-fluoro-phenyl)amino]-6-[trans-4-carboxy-cyclohexylamino]-pyrimido[5,4-d]pyrimidine
(366) 4-[(3,4-Dichloro-phenyl)amino]-6-[trans-4-carboxy-cyclohexylamino]-pyrimido[5,4-d]pyrimidine
(367) 4-[(3-Chloro-phenyl)amino]-6-[trans-4-carboxycyclohexylamino]-pyrimido[5,4-d]pyrimidine
(368) 4-[(3-Bromo-phenyl)amino]-6-[trans-4-carboxycyclohexylamino]-pyrimido[5,4-d]pyrimidine
(369) 4-[(3-Nitro-phenyl)amino]-6-[trans-4-carboxycyclohexylamino]-pyrimido[5,4-d]pyrimidine
(370) 4-[(3-Ethynyl-phenyl)amino]-6-[trans-4-carboxycyclohexylamino]-pyrimido[5,4-d]pyrimidine
(371) 4-[(3-Chloro-4-fluoro-phenyl)amino]-6-[trans-4-(N,N-di-methylamino-carbonyl)cyclohexylamino]-pyrimido[5,4-d]pyrimidine
(372) 4-[(3,4-Dichloro-phenyl)amino]-6-[trans-4-(N,N-dimethylamino-carbonyl)cyclohexylamino]-pyrimido[5,4-d]pyrimidine
(373) 4-[(3-Chloro-phenyl)amino]-6-[trans-4-(N,N-dimethylamino-carbonyl)cyclohexylamino]-pyrimido[5,4-d]pyrimidine
(374) 4-[(3-Bromo-phenyl)amino]-6-[trans-4-(N,N-dimethylamino-carbonyl)cyclohexylamino]-pyrimido[5,4-d]pyrimidine
(375) 4-[(3-Nitro-phenyl)amino]-6-[trans-4-(N,N-dimethylamino-carbonyl)cyclohexylamino]-pyrimido[5,4-d]pyrimidine
(376) 4-[(3-Ethynyl-phenyl)amino]-6-[trans-4-(N,N-dimethylamino-carbonyl)cyclohexylamino]-pyrimido[5,4-d]pyrimidine
(377) 4-[(3-Chloro-4-fluoro-phenyl)amino]-6-[trans-4-(morpholinocarbonyl)cyclohexylamino]-pyrimido[5,4-d]pyrimidine
(378) 4-[(3,4-Dichloro-phenyl)amino]-6-[trans-4-(morpholinocarbonyl)cyclohexylamino]-pyrimido[5,4-d]pyrimidine
(379) 4-[(3-Chloro-phenyl)amino]-6-[trans-4-(morpholinocarbonyl)cyclohexylamino]-pyrimido[5,4-d]pyrimidine
(380) 4-[(3-Bromo-phenyl)amino]-6-[trans-4-(morpholinocarbonyl)-cyclohexylamino]-pyrimido[5,4-d]pyrimidine
(381) 4-[(3-Nitro-phenyl)amino]-6-[trans-4-(morpholinocarbonyl)cyclohexylamino]-pyrimido[5,4-d]pyrimidine
(382) 4-[(3-Ethynyl-phenyl)amino]-6-[trans-4-(morpholinocarbonyl)cyclohexylamino]-pyrimido[5,4-d]pyrimidine
(383) 4-[(3-Chloro-4-fluoro-phenyl)amino]-6-[trans-4-(pyrrolidinocarbonyl)cyclohexyl amino]-pyrimido[5,4-d]pyrimidine
(384) 4-[(3,4-Dichloro-phenyl)amino]-6-[trans-4-(pyrrolidinocarbonyl)cyclohexylamino]-pyrimido[5,4-d]pyrimidine
(385) 4-[(3-Chloro-phenyl)amino]-6-[trans-4-(pyrrolidinocarbonyl)cyclohexylamino]-pyrimido[5,4-d]pyrimidine
(386) 4-[(3-Bromo-phenyl)amino]-6-[trans-4-(pyrrolidinocarbonyl)cyclohexylamino]-pyrimido[5,4-d]pyrimidine
(387) 4-[(3-Nitro-phenyl)amino]-6-[trans-4-(pyrrolidinocarbonyl)cyclohexylamino]-pyrimido[5,4-d]pyrimidine
(388) 4-[(3-Ethynyl-phenyl)amino]-6-[trans-4-(pyrrolidinocarbonyl)cyclohexylamino]-pyrimido[5,4-d]pyrimidine
(389) 4-[(3-Chloro-4-fluoro-phenyl)amino]-6-[(cis-4-hydroxy-cyclohexyl)amino]-pyrimido[5,4-d]pyrimidine
(390) 4-[(3,4-Dichloro-phenyl)amino]-6-[(cis-4-hydroxycyclohexyl)amino]-pyrimido[5,4-d]pyrimidine
(391) 4-[(3-Chloro-phenyl)amino]-6-[(cis-4-hydroxycyclohexyl)amino]-pyrimido[5,4-d]pyrimidine
(392) 4-[(3-Bromo-phenyl)amino]-6-[(cis-4-hydroxycyclohexyl)amino]-pyrimido[5,4-d]pyrimidine
(393) 4-[(3-Nitro-phenyl)amino]-6-[(cis-4-hydroxycyclohexyl)amino]-pyrimido[5,4-d]pyrimidine
(394) 4-[(3-Ethynyl-phenyl)amino]-6-[(cis-4-hydroxy-cyclohexyl)amino]-pyrimido[5,4-d]pyrimidine
(395) 4-[(3-Chloro-4-fluoro-phenyl)amino]-6-[N-(trans-4-hydroxy-cyclohexyl)-N-methyl-amino]-pyrimido[5,4-d]pyrimidine Melting point: 243°–246° C.

$R_f$ value: 0.51 (silica gel; petroleum ether/ethyl acetate/methanol=10:8:2)

(396) 4-[(3,4-Dichloro-phenyl)amino]-6-[N-(trans-4-hydroxy-cyclohexyl)-N-methyl-amino]-pyrimido[5,4-d]pyrimidine
(397) 4-[(3-Chloro-phenyl)amino]-6-[N-(trans-4-hydroxycyclohexyl)-N-methyl-amino]-pyrimido[5,4-d]pyrimidine (398) 4-[(3-Bromo-phenyl)amino]-6-[N-(trans-4-hydroxycyclohexyl)-N-methyl-amino]-pyrimido[5,4-d]pyrimidine (399) 4-[(3-Nitro-phenyl)amino]-6-[N-(trans-4-hydroxycyclohexyl)-N-methyl-amino]-pyrimido[5,4-d]pyrimidine (400) 4-[(3-Ethynyl-phenyl)amino]-6-[N-(trans-4-hydroxycyclohexyl)-N-methyl-amino]-pyrimido[5,4-d]pyrimidine (401) 4-[(3-Chloro-4-fluoro-phenyl)amino]-6-[(trans-4-hydroxy-4-methylcyclohexyl)amino]-pyrimido[5,4-d]pyrimidine (402) 4-[(3,4-Dichloro-phenyl)amino]-6-[(trans-4-hydroxy-4-methylcyclohexyl)amino]-pyrimido[5,4-d]pyrimidine (403) 4-[(3-Chloro-phenyl)amino]-6-[(trans-4-hydroxy-4-methylcyclohexyl)amino]-pyrimido[5,4-d]pyrimidine (404) 4-[(3-Bromo-phenyl)amino]-6-[(trans-4-hydroxy-4-methylcyclohexyl)amino]-pyrimido[5,4-d]pyrimidine (405) 4-[(3-Nitro-phenyl)amino]-6-[(trans-4-hydroxy-4-methylcyclohexyl)amino]-pyrimido[5,4-d]pyrimidine (406) 4-[(3-Ethynyl-phenyl)amino]-6-[(trans-4-hydroxy-4-methylcyclohexyl)amino]-pyrimido[5,4-d]pyrimidine (407) 4-[(3-Chloro-4-fluoro-phenyl)amino]-6-[(cis-4-hydroxy-4-methylcyclohexyl)amino]-pyrimido[5,4-d]pyrimidine (408) 4-[(3,4-Dichloro-phenyl)amino]-6-[(cis-4-hydroxy-4-methylcyclohexyl)amino]-pyrimido[5,4-d]pyrimidine (409) 4-[(3-Chloro-phenyl)amino]-6-[(cis-4-hydroxy-4-methylcyclohexyl)amino]-pyrimido[5,4-d]pyrimidine (410) 4-[(3-Bromo-phenyl)amino]-6-[(cis-4-hydroxy-4-methylcyclohexyl)amino]-pyrimido[5,4-d]pyrimidine (411) 4-[(3-Nitro-phenyl)amino]-6-[(cis-4-hydroxy-4-methylcyclohexyl)amino]-pyrimido[5,4-d]pyrimidine (412) 4-[(3-Ethynyl-phenyl)amino]-6-[(cis-4-hydroxy-4-methylcyclohexyl)amino]-pyrimido[5,4-d]pyrimidine (413) 4-[(3-Chloro-4-fluoro-phenyl)amino]-6-[4-tetrahydropyranylamino]-pyrimido[5,4-d]pyrimidine (414) 4-[(3,4-Dichloro-phenyl)amino]-6-[4-tetrahydropyranylamino]-pyrimido[5,4-d]pyrimidine (415) 4-[(3-Chloro-phenyl)amino]-6-[4-tetrahydropyranylamino]-pyrimido[5,4-d]pyrimidine (416) 4-[(3-Bromo-phenyl)amino]-6-[4-tetrahydropyranylamino]-pyrimido[5,4-d]pyrimidine (417) 4-[(3-Nitro-phenyl)amino]-6-[4-tetrahydropyranylamino]-pyrimido[5,4-d]pyrimidine (418) 4-[(3-Ethynyl-phenyl)amino]-6-[4-tetrahydropyranylamino]-pyrimido[5,4-d]pyrimidine (419) 4-[(3-Chloro-4-fluoro-phenyl)amino]-6-[(4-oxocyclohexyl)amino]-pyrimido[5,4-d]pyrimidine (420) 4-[(3,4-Dichloro-phenyl)amino]-6-[(4-oxocyclohexyl)amino]-pyrimido[5,4-d]pyrimidine (421) 4-[(3-Chloro-phenyl)amino]-6-[(4-oxocyclohexyl)amino]-pyrimido[5,4-d]pyrimidine (422) 4-[(3-Bromo-phenyl)amino]-6-[(4-oxocyclohexyl)amino]-pyrimido[5,4-d]pyrimidine (423) 4-[(3-Nitro-phenyl)amino]-6-[(4-oxocyclohexyl)amino]-pyrimido[5,4-d]pyrimidine (424) 4-[(3-Ethynyl-phenyl)amino]-6-[(4-oxocyclohexyl)amino]-pyrimido[5,4-d]pyrimidine (425) 4-[(3-Chloro-4-fluoro-phenyl)amino]-6-(4-oxo-1-piperidinyl)-pyrimido[5,4-d]pyrimidine (426) 4-[(3,4-Dichloro-phenyl)amino]-6-(4-oxo-1-piperidinyl)-pyrimido[5,4-d]pyrimidine (427) 4-[(3-Chloro-phenyl)amino]-6-(4-oxo-1-piperidinyl)-pyrimido[5,4-d]pyrimidine (428) 4-[(3-Bromo-phenyl)amino]-6-(4-oxo-1-piperidinyl)-pyrimido[5,4-d]pyrimidine (429) 4-[(3-Nitro-phenyl)amino]-6-(4-oxo-1-piperidinyl)-pyrimido[5,4-d]pyrimidine (430) 4-[(3-Ethynyl-phenyl)amino]-6-(4-oxo-1-piperidinyl)-pyrimido[5,4-d]pyrimidine (431) 4-[(3-Chloro-4-fluoro-phenyl)amino]-6-morpholino-pyrimido[5,4-d]pyrimidine
Melting point: 218°–221° C.
$R_f$ value: 0.47 (silica gel; petroleum ether/ethyl acetate/methanol=10:5:1)

(432) 4-[(3,4-Dichloro-phenyl)amino]-6-morpholino-pyrimido-[5,4-d]pyrimidine (433) 4-[(3-Nitro-phenyl)amino]-6-morpholino-pyrimido[5,4-d]pyrimidine (434) 4-[(3-Ethynyl-phenyl)amino]-6-morpholino-pyrimido[5,4-d]pyrimidine (435) 4-[(3-Chloro-4-fluoro-phenyl)amino]-6-(4-piperidinyl-amino)-pyrimido[5,4-d]pyrimidine (436) 4-[(3,4-Dichloro-phenyl)amino]-6-(4-piperidinyl-amino)-pyrimido[5,4-d]pyrimidine (437) 4-[(3-Chloro-phenyl)amino]-6-(4-piperidinyl-amino)-pyrimido[5,4-d]pyrimidine (438) 4-[(3-Bromo-phenyl)amino]-6-(4-piperidinyl-amino)-pyrimido[5,4-d]pyrimidine (439) 4-[(3-Nitro-phenyl)amino]-6-(4-piperidinyl-amino)-pyrimido[5,4-d]pyrimidine (440) 4-[(3-Ethynyl-phenyl)amino]-6-(4-piperidinyl-amino)-pyrimido[5,4-d]pyrimidine (441) 4-[(3,4-Dichloro-phenyl)amino]-6-[2-(morpholino)-ethylamino]-pyrimido[5,4-d]pyrimidin (442) 4-[(3-Chloro-phenyl)amino]-6-[2-(morpholino)-ethylamino]-pyrimido[5,4-d]pyrimidine (443) 4-[(3-Bromo-phenyl)amino]-6-[2-(morpholino)-ethylamino]-pyrimido[5,4-d]pyrimidine (444) 4-[(3-Nitro-phenyl)amino]-6-[2-(morpholino)-ethylamino]-pyrimido[5,4-d]pyrimidine (445) 4-[(3-Ethynyl-phenyl)amino]-6-[2-(morpholino)-ethylamino]-pyrimido[5,4-d]pyrimidin (446) 4-[(3-Methyl-phenyl)amino]-6-[2-(morpholino)-ethylamino]-pyrimido[5,4-d]pyrimidine (447) 4-[(3-Chloro-4-fluoro-phenyl)amino]-6-isopropylamino-pyrimido[5,4-d]pyrimidine (448) 4-[(3,4-Dichloro-phenyl)amino]-6-isopropylamino-pyrimido[5,4-d]pyrimidine (449) 4-[(3-Nitro-phenyl)amino]-6-isopropylamino-pyrimido[5,4-d]pyrimidine (450) 4-[(3-Ethynyl-phenyl)amino]-6-isopropylamino-pyrimido[5,4-d]pyrimidine (451) 4-[(3-Chloro-4-fluoro-phenyl)amino]-6-(tert-butylamino)-pyrimido[5,4-d]pyrimidine (452) 4-[(3,4-Dichloro-phenyl)amino]-6-(tert-butylamino)-pyrimido[5,4-d]pyrimidine (453) 4-[(3-Chloro-phenyl)amino]-6-(tert-butylamino)-pyrimido[5,4-d]pyrimidine (454) 4-[(3-Bromo-phenyl)amino]-6-(tert-butylamino)-pyrimido[5,4-d]pyrimidine (455) 4-[(3-Nitro-phenyl)amino]-6-(tert-butylamino)-pyrimido[5,4-d]pyrimidine (456) 4-[(3-Ethynyl-phenyl)amino]-6-(tert-butylamino)-pyrimido[5,4-d]pyrimidine (457) 4-[(3-Chloro-4-fluoro-phenyl)amino]-6-(1-hydroxy-2-propylamino)-pyrimido[5,4-d]pyrimidine
Melting point: 227°–231° C.
$R_f$ value: 0.44 (silica gel; petroleum ether/ethyl acetate/methanol=10:10:2)

(458) 4-[(3,4-Dichloro-phenyl)amino]-6-(1-hydroxy-2-propylamino)-pyrimido[5,4-d]pyrimidine (459) 4-[(3-Chloro-phenyl)amino]-6-(1-hydroxy-2-propylamino)-pyrimido[5,4-d]pyrimidine (460) 4-[(3-Bromo-phenyl)amino]-6-(1-hydroxy-2-propylamino)-pyrimido[5,4-d]pyrimidine
(461) 4-[(3-Nitro-phenyl)amino]-6-(1-hydroxy-2-propylamino)-pyrimido[5,4-d]pyrimidine
(462) 4-[(3-Ethynyl-phenyl)amino]-6-(1-hydroxy-2-propylamino)-pyrimido[5,4-d]pyrimidine
(463) 4-[(3-Chloro-4-fluoro-phenyl)amino]-6-(1-methyl-4-piperidinyl-amino)-pyrimido[5,4-d]pyrimidine
(464) 4-[(3,4-Dichloro-phenyl)amino]-6-(1-methyl-4-piperidinyl-amino)-pyrimido[5,4-d]pyrimidine
(465) 4-[(3-Chloro-phenyl)amino]-6-(1-methyl-4-piperidinyl-amino)-pyrimido[5,4-d]pyrimidine
(466) 4-[(3-Bromo-phenyl)amino]-6-(1-methyl-4-piperidinyl-amino)-pyrimido[5,4-d]pyrimidine
(467) 4-[(3-Nitro-phenyl)amino]-6-(1-methyl-4-piperidinyl-amino)-pyrimido[5,4-d]pyrimidine
(468) 4-[(3-Ethynyl-phenyl)amino]-6-(1-methyl-4-piperidinyl-amino)-pyrimido[5,4-d]pyrimidine
(469) 4-[(3-Chloro-4-fluoro-phenyl)amino]-6-(propargylamino)-pyrimido[5,4-d]pyrimidine
(470) 4-[(3,4-Dichloro-phenyl)amino]-6-(propargylamino)-pyrimido[5,4-d]pyrimidine
(471) 4-[(3-Chloro-phenyl)amino]-6-(propargylamino)-pyrimido[5,4-d]pyrimidine
(472) 4-[(3-Bromo-phenyl)amino]-6-(propargylamino)-pyrimido[5,4-d]pyrimidine
(473) 4-[(3-Nitro-phenyl)amino]-6-(propargylamino)-pyrimido[5,4-d]pyrimidine
(474) 4-[(3-Ethynyl-phenyl)amino]-6-(propargylamino)-pyrimido[5,4-d]pyrimidine
(475) 4-[(3-Chloro-4-fluoro-phenyl)amino]-6-(1-pyrrolidinyl)-pyrimido[5,4-d]pyrimidine
(476) 4-[(3,4-Dichloro-phenyl)amino]-6-(1-pyrrolidinyl)-pyrimido[5,4-d]pyrimidine
(477) 4-[(3-Nitro-phenyl)amino]-6-(1-pyrrolidinyl)-pyrimido[5,4-d]pyrimidine
(478) 4-[(3-Ethynyl-phenyl)amino]-6-(1-pyrrolidinyl)-pyrimido[5,4-d]pyrimidine
(479) 4-[(3-Chloro-4-fluoro-phenyl)amino]-6-(tetrahydrofurfurylamino)-pyrimido[5,4-d]pyrimidine
Melting point: 158°–160° C.
$R_f$ value: 0.40 (silica gel; petroleum ether/ethyl acetate =1:1)
(480) 4-[(3,4-Dichloro-phenyl)amino]-6-(tetrahydrofurfurylamino)-pyrimido[5,4-d]pyrimidine
(481) 4-[(3-Chloro-phenyl)amino]-6-(tetrahydrofurfurylamino)-pyrimido[5,4-d]pyrimidine
(482) 4-[(3-Bromo-phenyl)amino]-6-(tetrahydrofurfurylamino)-pyrimido[5,4-d]pyrimidine
(483) 4-[(3-Nitro-phenyl)amino]-6-(tetrahydrofurfurylamino)-pyrimido[5,4-d]pyrimidine
(484) 4-[(3-Ethynyl-phenyl)amino]-6-(tetrahydrofurfurylamino)-pyrimido[5,4-d]pyrimidine
(485) 4-[(3-Chloro-4-fluoro-phenyl)amino]-6-(3-tetrahydrofuranylamino)-pyrimido[5,4-d]pyrimidine
Prepared from the compounds of Examples 2 and XIX.
Melting point: 239°–241° C.
$R_f$ value: 0.51 (silica gel; petroleum ether/ethyl acetate/methanol=10:10:1)
(486) 4-[(3,4-Dichloro-phenyl)amino]-6-(3-tetrahydrofuranylamino)-pyrimido[5,4-d]pyrimidine
(487) 4-[(3-Chloro-phenyl)amino]-6-(3-tetrahydrofuranylamino)-pyrimido[5,4-d]pyrimidine
(488) 4-[(3-Bromo-phenyl)amino]-6-(3-tetrahydrofuranylamino)-pyrimido[5,4-d]pyrimidine
(489) 4-[(3-Nitro-phenyl)amino]-6-(3-tetrahydrofuranylamino)-pyrimido[5,4-d]pyrimidine
(490) 4-[(3-Ethynyl-phenyl)amino]-6-(3-tetrahydrofuranylamino)-pyrimido[5,4-d]pyrimidine
(491) 4-[(3-Chloro-4-fluoro-phenyl)amino]-6-[2-(1-methyl-4-piperazinyl)ethylamino]-pyrimido[5,4-d]pyrimidine
(492) 4-[(3-Chloro-4-fluoro-phenyl)amino]-6-[2-(1-acetyl-4-piperazinyl)ethylamino]-pyrimido[5,4-d]pyrimidine
(493) 4-[(3-Chloro-4-fluoro-phenyl)amino]-6-[2-(1-methylsulphonyl-4-piperazinyl)ethylamino]-pyrimido[5,4-d]pyrimidine
(494) 4-[(3-Chloro-4-fluoro-phenyl)amino]-6-[2-(1-methoxycarbonyl-4-piperazinyl)ethylamino]-pyrimido[5,4-d]pyrimidine
(495) 4-[(3-Chloro-4-fluoro-phenyl)amino]-6-[2-(1-cyan-4-piperazinyl)ethylamino]-pyrimido[5,4-d]pyrimidine
(496) 4-[(3-Chloro-4-fluoro-phenyl)amino]-6-[2-(1-dimethylaminocarbonyl-4-piperazinyl)ethylamino]-pyrimido[5,4-d]pyrimidine
(497) 4-[(4-Amino-3,5-dibromo-phenyl)amino]-6-[(trans-4-hydroxy-cyclohexyl)amino]-pyrimido[5,4-d]pyrimidine
Melting point: 228°–230° C.
$R_f$ value: 0.40 (silica gel; petroleum ether/ethyl acetate/methanol=10:10:3) Calculated: C 42.45 H 3.76 N 19.25 Found: 42.59 4.10 19.06
Mass spectrum: $M^+$=507
(498) 4-[(4-Amino-5-bromo-3-chloro-phenyl)amino]-6-[(trans-4-hydroxy-cyclohexyl)amino]-pyrimido[5,4-d]pyrimidine
(499) 4-[(3,5-Dichloro-4-dimethylamino-phenyl)amino]-6-[(trans-4-hydroxy-cyclohexyl)amino]-pyrimido[5,4-d]pyrimidine
(500) 4-[(4-Acetylamino-3,5-dichloro-phenyl)amino]-6-[(trans-4-hydroxy-cyclohexyl)amino]-pyrimido[5,4-d]pyrimidine
(501) 4-[(4-Methylsulphonylamino-3,5-dichloro-phenyl)amino]-6-[(trans-4-hydroxy-cyclohexyl)amino]-pyrimido[5,4-d]pyrimidine
(502) 4-[(4-Trifluoromethylsulphonylamino-3,5-dichloro-phenyl)amino]-6-[(trans-4-hydroxy-cyclohexyl)amino]-pyrimido[5,4-d]pyrimidine
(503) 4-[(3,5-Dibromo-4-hydroxy-phenyl)amino]-6-[(trans-4-hydroxy-cyclohexyl)amino]-pyrimido[5,4-d]pyrimidine
(504) 4-[(3,5-Dichloro-4-hydroxy-phenyl)amino]-6-[(trans-4-hydroxy-cyclohexyl)amino]-pyrimido[5,4-d]pyrimidine
(505) 4-[(3,5-Dichloro-4-methoxy-phenyl)amino]-6-[(trans-4-hydroxy-cyclohexyl)amino]-pyrimido[5,4-d]pyrimidine
(506) 4-[(3-Chloro-4-fluoro-phenyl)amino]-6-[3-hydroxycyclopentylamino]-pyrimido[5,4-d]pyrimidine
(507) 4-[(3-Chloro-4-fluoro-phenyl)amino]-6-[1-hydroxy-3-methyl-3-butylamino]-pyrimido[5,4-d]pyrimidine
(508) 4-[(3-Chloro-4-fluoro-phenyl)amino]-6-[1-hydroxy-4-methyl-4-pentylamino]-pyrimido[5,4-d]pyrimidine
(509) 4-[(3-Chloro-4-fluoro-phenyl)amino]-6-methyl-pyrimido[5,4-d]pyrimidine
(510) 4-[(3-Chloro-4-fluoro-phenyl)amino]-6-phenyl-pyrimido[5,4-d]pyrimidine
(511) 4-[(3-Chloro-4-fluoro-phenyl)amino]-6-(4-methoxyphenyl)-pyrimido[5,4-d]pyrimidine
(512) 4-[(3-Chloro-4-fluoro-phenyl)amino]-6-[4-(2-hydroxymethyl-1-pyrrolidinyl)cyclohexylamino]-pyrimido[5,4-d]pyrimidine
(513) 4-[(3-Chloro-4-fluoro-phenyl)amino]-6-[4-(2-oxo-1-pyrrolidinyl)cyclohexylamino]-pyrimido[5,4-d]pyrimidine
(514) 4-[(3-Chloro-4-fluoro-phenyl)amino]-6-[4-(N-acetyl-N-methylamino)cyclohexylamino]-pyrimido[5,4-d]pyrimidine (515) 4-[(3-Chloro-4-fluoro-phenyl)amino]-6-[4-(N,N-bis-(2-hydroxyethyl)amino)cyclohexylamino]-pyrimido[5,4-d]pyrimidine (516) 4-[(3-Chloro-4-fluoro-phenyl)amino]-6-[4-(N-ethyl-N-(2-hydroxyethyl)amino)cyclohexylamino]-pyrimido[5,4-d]pyrimidine (517) 4-[(3-Chloro-4-fluoro-phenyl)amino]-6-[4-(1-pyrrolidinyl)cyclohexylamino]-pyrimido[5,4-d]pyrimidine (518) 4-[(3-Chloro-4-fluoro-phenyl)amino]-6-[4-(2-oxo-1-imidazolidinyl)cyclohexylamino]-pyrimido[5,4-d]pyrimidine (519) 4-[(3-Chloro-4-fluoro-phenyl)amino]-6-[4-(3-methyl-2-oxo-1-imidazolidinyl)cyclohexylamino]-pyrimido[5,4-d]pyrimidine (520) 4-[(3-Chloro-4-fluoro-phenyl)amino]-6-[4-(N-acetyl-N-methylamino)phenylamino]-pyrimido[5,4-d]pyrimidine (521) 4-[(3-Chloro-4-fluoro-phenyl)amino]-6-[4-(N,N-bis-(2-hydroxyethyl)amino)phenylamino]-pyrimido[5,4-d]pyrimidine (522) 4-[(3-Chloro-4-fluoro-phenyl)amino]-6-[4-(N-ethyl-N-(2-hydroxyethyl)amino)phenylamino]-pyrimido[5,4-d]pyrimidine (523) 4-[(3-Chloro-4-fluoro-phenyl)amino]-6-[4-(1-pyrrolidinyl)phenylamino]-pyrimido[5,4-d]pyrimidine (524) 4-[(3-Chloro-4-fluoro-phenyl)amino]-6-[4-(2-oxo-1-imidazolidinyl)phenylamino]-pyrimido[5,4-d]pyrimidine (525) 4-[(3-Chloro-4-fluoro-phenyl)amino]-6-[4-(3-methyl-2-oxo-1-imidazolidinyl)phenylamino]-pyrimido[5,4-d]pyrimidine (526) 4-[(3-Difluoromethoxy-phenyl)amino]-6-[(trans-4-hydroxy-cyclohexyl)amino]-pyrimido[5,4-d]pyrimidine (527) 4-[(3-Chloro-4-fluoro-phenyl)amino]-6-[4-morpholinocyclohexylamino]-pyrimido[5,4-d]pyrimidine (528) 4-[(3-Chloro-4-fluoro-phenyl)amino]-6-[4-morpholinophenylamino]-pyrimido[5,4-d]pyrimidine
Melting point: 250°–254° C.
$R_f$ value: 0.49 (silica gel=petroleum ether/ethyl acetate/methanol=10:10:2)

(529) 4-[(3-Chloro-4-fluoro-phenyl)amino]-6-dimethylamino-pyrimido[5,4-d]pyrimidine
Melting point: 203°–205° C.
$R_f$ value: 0.85 (silica gel=petroleum ether/ethyl acetate/methanol=10:10:2)
Mass spectrum: $M^+=318$ (530) 4-[(3-Chloro-4-fluoro-phenyl)amino]-6-[4-amino-1-piperidinyl]-pyrimido[5,4-d]pyrimidine
Melting point: 169°–174° C.
$R_f$ value: 0.50 (silica gel=methylene chloride/methanol/conc. ammonia;=100:30:1)

(531) 4-[(3-Chloro-4-fluoro-phenyl)amino]-6-[4-dimethylamino-1-piperidinyl]-pyrimido[5,4-d]pyrimidine
Melting point: 162°–165° C.
$R_f$ value: 0.48 (silica gel; methylene chloride/methanol=10.3)

(532) 4-[(3-Chloro-4-fluoro-phenyl)amino]-6-[2-dimethylamino-1-ethoxy]-pyrimido[5,4-d]pyrimidine
Melting point: 98°–100° C.
$R_f$ value: 0.38 (silica gel=petroleum ether/ethyl acetate/methanol=10:10:4)

EXAMPLE 2

4-[(3-Methylphenyl)amino]-6-methylsulphinyl-pyrimido[5,4-d]pyrimidine and 4-[(3-methylphenyl)amino]-6-methylsulphonyl-pyrimido[5,4-d]pyrimidine 3.9 g of 4-[(3-methylphenyl)amino]-6-methylthio-pyrimido[5,4-d]pyrimidine and 6.28 g of 3-chloroperoxybenzoic acid (50% strength) in 100 ml of methylene chloride are heated under reflux for 75 minutes. After cooling, water is added and the or organic phase is separated off, washed with sodium bicarbonate solution and water, dried and evaporated on a rotary evaporator. The residue is stirred with diethyl ether and the solid is filtered off with suction and dried.

Yield: 4.2 g,
$R_f$ value: 0.38 and 0.54 (silica gel; petroleum ether/ethyl acetate=10:10:1)

The compounds were separated by chromatography and characterized:

a) 4-[(3-Methylphenyl)amino]-6-methylsulphinyl-pyrimido[5,4-d]pyrimidine
Melting point: 118° C.
$R_f$ value: 0.73 (silica gel; ethyl acetate/methanol=10:1)
Mass spectrum: $M^+=299$ b) 4-[(3-Methylphenyl)amino]-6-methylsulphonyl-pyrimido[5,4-d]pyrimidine
Melting point: 220° C.
$R_f$ value: 0.60 (silica gel; ethyl acetate)
Mass spectrum: $M^+=315$ The following compounds are obtained analogously to Example 2:

(1) 4-(phenylamino)-6-methylsulphonyl-pyrimido[5,4-d]-pyrimidine
An excess of 3-chloroperoxybenzoic acid is used.
$R_f$ value: 0.36 (silica gel; petroleum ether/ethyl acetate/methanol=10:10:1)

(2) 4-(N-Methyl-N-phenyl-amino)-6-methylsulphonyl-pyrimido[5,4-d]pyrimidine
An excess of 3-chloroperoxybenzoic acid is used.
$R_f$ value: 0.32 (silica gel; petroleum ether/ethyl acetate/methanol=10:10:1)

(3) 4-[(3-Fluorophenyl)amino]-6-methylsulphonyl-pyrimido[5,4-d]pyrimidine
$R_f$ value: 0.64 (silica gel; petroleum ether/ethyl acetate/methanol=10:10:1)

(4) 4-[(3-Chlorophenyl)amino]-6-methylsulphonyl-pyrimido[5,4-d]pyrimidine
$R_f$ value: 0.50 (silica gel; petroleum ether/ethyl acetate/methanol=10:10:1)

(5) 4-[(3-Bromophenyl)amino]-6-methylsulphonyl-pyrimido[5,4-d]pyrimidine
$R_f$ value: 0.38 (silica gel; petroleum ether/ethyl acetate/methanol=10:10:1)

(6) 4-[(3-Trifluoromethylphenyl)amino]-6-methylsulphonyl-pyrimido[5,4-d]pyrimidine
$R_f$ value: 0.54 (silica gel; petroleum ether/ethyl acetate/methanol=10:10:1)

(7) 4-[(3-Methoxyphenyl)amino]-6-methylsulphonyl-pyrimido[5,4-d]pyrimidine
$R_f$ value: 0.49 (silica gel; petroleum ether/ethyl acetate/methanol=10:10:1)

(8) 4-[(3-Ethylphenyl)amino]-6-methylsulphonyl-pyrimido[5,4-d]pyrimidine
$R_f$ value: 0.37 (silica gel; petroleum ether/ethyl acetate=1:1)

(9) 4-[(3,4-Dichlorophenyl)amino]-6-methylsulphonyl-pyrimido[5,4-d]pyrimidine
$R_f$ value: 0.45 (silica gel; petroleum ether/ethyl acetate=1:1)

(10) 4-[(3-Chloro-4-fluoro-phenyl)amino]-6-methylsulphonylpyrimido[5,4-d]pyrimidine
$R_f$ value: 0.45 (silica gel; petroleum ether/ethyl acetate/methanol=10:8:2)

(11) 4-[(3-Chloro-4-methoxy-phenyl)amino]-6-methylsulphonyl-pyrimido[5,4-d]pyrimidine

(12) 4-[(4-Amino-3-nitro-phenyl)amino]-6-methylsulphonyl-pyrimido[5,4-d]pyrimidine $R_f$ value: 0.19 (silica gel; methylene chloride/ethyl acetate/methanol=10:4:2)

(13) 4-[(4-Chloro-3-nitro-phenyl)amino]-6-methylsulphonyl-pyrimido[5,4-d]pyrimidine $R_f$ value: 0.38 (silica gel; petroleum ether/ethyl acetate/methanol=10:10:3)

(14) 4-[(4-Amino-3-cyano-phenyl)amino]-6-methylsulphonyl-pyrimido[5,4-d]pyrimidine $R_f$ value: 0.25 (silica gel; petroleum ether/ethyl acetate/methanol=10:10:2)

(15) 4-[(4-Amino-3,5-dichloro-phenyl)amino]-6-methylsulphonyl-pyrimido[5,4-d]pyrimidine $R_f$ value: 0.40 (silica gel; petroleum ether/ethyl acetate/methanol=10:10:2)

(16) 4-[(4-Amino-3,5-dibromo-phenyl)amino]-6-methylsulphonyl-pyrimido[5,4-d]pyrimidine $R_f$ value: 0.53 (silica gel; petroleum ether/ethyl acetate/methanol=10:10:2)

EXAMPLE 3

4-[(3-Methylphenyl)amino]-6-methylthio-pyrimido[5,4-d]-pyrimidine 4.9 g of 4-chloro-6-methylthio-pyrimido[5,4-d]pyrimidine, 2.0 g of 3-methylaniline, 2.4 ml of triethylamine and 100 ml of dioxane are heated at 100° C. for 3 hours. After cooling, the reaction mixture is concentrated and partitioned between water and methylene chloride. The organic phase is separated off, dried and concentrated and the residue is purified by chromatography over a silica gel column (petroleum ether/ethyl acetate=2:1). The solid is triturated with diethyl ether, filtered off with suction and dried.

Yield: 2.8 g (43% of theory),

Melting point: 118°–120° C.

$R_f$ value: 0.55 (silica gel; petroleum ether/ethyl acetate=2:1)

The following compounds are obtained analogously to Example 3:

(1) 4-(Phenylamino)-6-methylthio-pyrimido[5,4-d]pyrimidine $R_f$ value: 0.63 (silica gel; petroleum ether/ethyl acetate=2:1)

(2) 4-[(4-Fluorophenyl)amino]-6-(cyclopropylamino)-pyrimido[5,4-d]pyrimidine

Starting material: compound of Example IV, heating for 2½ days.

Melting point: 200°–202° C.

$R_f$ value: 0.44 (silica gel; petroleum ether/ethyl acetate=1:1) Calculated: C 60.80 H 4.42 N 28.36 Found: 60.77 4.52 28.60

(3) 4-(N-Methyl-N-phenyl-amino)-6-methylthio-pyrimido[5,4-d]pyrimidine $R_f$ value: 0.45 (silica gel; petroleum ether/ethyl acetate=2:1)

(4) 4-[(3,4-Difluorophenyl)amino]-6-(cyclopropylamino)-pyrimido[5,4-d]pyrimidine Melting point: 212°–214° C.

$R_f$ value: 0.51 (silica gel; petroleum ether/ethyl acetate 1:1)

(5) 4-[(3,5-Difluorophenyl)amino]-6-(cyclopropylamino)-pyrimido[5,4-d]pyrimidine Carried out in butanol at the reflux temperature in the presence of N-ethyl-diisopropylamine.

Melting point: 199°–201° C.

$R_f$ value: 0.62 (silica gel; petroleum ether/ethyl acetate=1:1)

(6) 4-[(3-Chloro-4-fluoro-phenyl)amino]-6-(cyclopropylamino)-pyrimido[5,4-d]pyrimidine Melting point: 197°–199° C.

(7) 4-[(3,5-Bis-(trifluoromethyl)-phenyl)amino]-6-(cyclopropylamino)-pyrimido[5,4-d]pyrimidine Melting point: 228°–230° C.

$R_f$ value: 0.68 (silica gel; petroleum ether/ethyl acetate=1:1)

(8) 4-[(4-Fluoro-3-trifluoromethylphenyl)amino]-6-(cyclopropylamino)-pyrimido[5,4-d]pyrimidine Melting point: 174°–176° C.

$R_f$ value: 0.50 (silica gel; petroleum ether/ethyl acetate=1:1) Calculated: C 52.75 H 3.23 N 23.06 Found: 52.52 3.52 22.66

(9) 4-[(4-Fluoro-3-methylphenyl)amino]-6-(cyclopropylamino)-pyrimido[5,4-d]pyrimidine Melting point: 180°–182° C.

$R_f$ value: 0.40 (silica gel; petroleum ether/ethyl acetate=1:1) Calculated: C 61.92 H 4.87 N 27.08 Found: 61.71 4.96 26.82

(10) 4-[(4-Trifluoromethylphenyl)amino]-6-(cyclopropylamino)-pyrimido[5,4-d]pyrimidine Melting point: 229°–231° C.

$R_f$ value: 0.23 (silica gel; petroleum ether/ethyl acetate=2:1)

(11) 4-[(3-Fluorophenyl)amino]-6-methylthio-pyrimido[5,4-d]pyrimidine $R_f$ value: 0.52 (silica gel; petroleum ether/ethyl acetate=2:1)

(12) 4-[(3-Chlorophenyl)amino]-6-methylthio-pyrimido[5,4-d]pyrimidine $R_f$ value: 0.54 (silica gel; petroleum ether/ethyl acetate=2:1)

(13) 4-[(3-Bromophenyl)amino]-6-methylthio-pyrimido[5,4-d]pyrimidine $R_f$ value: 0.60 (silica gel; petroleum ether/ethyl acetate=2:1)

(14) 4-[(3-Trifluoromethylphenyl)amino]-6-methylthio-pyrimido[5,4-d]pyrimidine $R_f$ value: 0.62 (silica gel; petroleum ether/ethyl acetate=2:1)

(15) 4-[(3-Methoxyphenyl)amino]-6-methylthio-pyrimido[5,4-d]pyrimidine

Melting point: 168°–170° C.

$R_f$ value: 0.49 (silica gel; petroleum ether/ethyl acetate=2:1)

(16) 4-[(3-Ethylphenyl)amino]-6-methylthio-pyrimido[5,4-d]pyrimidine $R_f$ value: 0.53 (silica gel; petroleum ether/ethyl acetate=2:1)

(17) 4-[(3-Iodophenyl)amino]-6-(cyclopropylamino)-pyrimido[5,4-d]pyrimidine

Melting point: 240°–242° C.

$R_f$ value: 0.47 (silica gel; petroleum ether/ethyl acetate=1:1) Calculated: C 44.57 H 3.42 N 20.79 Found: 44.50 3.46 20.86

(18) 4-[(3-Trifluoromethoxyphenyl)amino]-6-(cyclopropylamino)-pyrimido[5,4-d]pyrimidine Melting point: 168°–170° C.

$R_f$ value: 0.55 (silica gel; petroleum ether/ethyl acetate=1:1)

(19) 4-[(3-Cyanophenyl)amino]-6-(cyclopropylamino)-pyrimido[5,4-d]pyrimidine

Melting point: 240° C.

$R_f$ value: 0.41 (silica gel; petroleum ether/ethyl acetate=1:1)

(20) 4-[(3-Ethoxycarbonylphenyl)amino]-6-(cyclopropylamino)-pyrimido[5,4-d]pyrimidine

(21) 4-[(3-Isopropylphenyl)amino]-6-(cyclopropylamino)-pyrimido[5,4-d]pyrimidine

(22) 4-[(3-Cyclopropylphenyl)amino]-6-(cyclopropylamino)-pyrimido[5,4-d]pyrimidine

(23) 4-[(4-Chlorophenyl)amino]-6-(cyclopropylamino)-pyrimido[5,4-d]pyrimidine

Melting point: 218°–220° C.

$R_f$ value: 0.45 (silica gel; petroleum ether/ethyl acetate=1:1) Calculated: C 57.60 H 4.18 N 26.87 Found: 57.71 4.32 26.57

(24) 4-[(4-Methylphenyl)amino]-6-(cyclopropylamino)-pyrimido[5,4-d]pyrimidine

Melting point: 192°–194° C.

$R_f$ value: 0.47 (silica gel; petroleum ether/ethyl acetate=1:1) Calculated: C 65.73 H 5.51 N 28.74 Found: 65.67 5.65 28.51

(25) 4-[(4-Methoxyphenyl)amino]-6-(cyclopropylamino)-pyrimido[5,4-d]3 pyrimidine Melting point: 187°–189° C.

$R_f$ value: 0.45 (silica gel; petroleum ether/ethyl acetate=1:1) Calculated: C 62.32 H 5.23 N 27.25 Found: 62.14 5.29 26.95

(26) 4-[(4-tert-Butylphenyl)amino]-6-(cyclopropylamino)-pyrimido[5,4-d]pyrimidine Melting point: 142°–144° C.

$R_f$ value: 0.55 (silica gel; petroleum ether/ethyl acetate=1:1) Calculated: C 68.23 H 6.63 N 25.13 Found: 68.16 6.77 24.72

(27) 4-[3-(Cyclopentyloxy)phenyl]amino]-6-(cyclopropylamino)-pyrimido[5,4-d]pyrimidine

(28) 4-[(4-Bromophenyl)amino]-6-(cyclopropylamino)-pyrimido[5,4-d]pyrimidine

Melting point: 229°–231° C.

$R_f$ value: 0.42 (silica gel; petroleum ether/ethyl acetate=1:1) Calculated: C 50.42 H 3.66 N 23.52 Found: 50.41 3.79 23.50

(29) 4-[(2-Methylphenyl)amino]-6-(cyclopropylamino)-pyrimido[5,4-d]pyrimidine

Melting point: 218°–220° C.

$R_f$ value: 0.40 (silica gel; petroleum ether/ethyl acetate=1:1) Calculated: C 65.73 H 5.51 N 28.74 Found: 65.72 5.55 28.22

(30) 4-[(3,4-Dimethylphenyl)amino]-6-(cyclopropylamino)-pyrimido[5,4-d]pyrimidine Melting point: 180°–182° C.

$R_f$ value: 0.40 (silica gel; petroleum ether/ethyl acetate=1:1) Calculated: C 66.64 H 5.92 N 27.43 Found: 66.56 5.99 27.51

(31) 4-[(5-Indanyl)amino]-6-(cyclopropylamino)-pyrimido[5,4-d]pyrimidine

Melting point: 199°–201° C.

$R_f$ value: 0.42 (silica gel; petroleum ether/ethyl acetate=1:1)

(32) 4-[(2-Naphthyl)amino]-6-(cyclopropylamino)-pyrimido[5,4-d]pyrimidine

Melting point: 187°–189° C.

$R_f$ value: 0.38 (silica gel; petroleum ether/ethyl acetate=1:1) Calculated: C 69.49 H 4.91 N 25.59 Found: 69.22 4.96 25.87

(33) 4-[(1,2,3,4-Tetrahydro-6-naphthyl)amino]-6-(cyclopropylamino)-pyrimido[5,4-d]pyrimidine

(34) 4-[(3,5-Dimethylphenyl)amino]-6-(cyclopropylamino)-pyrimido[5,4-d]pyrimidine Melting point: 210°–212° C.

$R_f$ value: 0.48 (silica gel; petroleum ether/ethyl acetate=1:1) Calculated: C 66.64 H 5.92 N 27.43 Found: 66.71 6.07 27.60

(35) 4-[(2,5-Dimethylphenyl)amino]-6-(cyclopropylamino)-pyrimido[5,4-d]pyrimidine Melting point: 210°–212° C.

$R_f$ value: 0.38 (silica gel; petroleum ether/ethyl acetate=1:1) Calculated: C 66.64 H 5.92 N 27.43 Found: 66.65 5.93 27.56

(36) 4-[(3,4-Dichlorophenyl)amino]-6-(cyclopropylamino)-pyrimido[5,4-d]pyrimidine Melting point: 228°–230° C.

$R_f$ value: 0.40 (silica gel; petroleum ether/ethyl acetate=1:1) Calculated: C 51.88 H 3.48 N 24.20 Found: 51.70 3.52 23.77

(37) 4-[(2-Fluorophenyl)amino]-6-(cyclopropylamino)-pyrimido[5,4-d]pyrimidine

Melting point: 198°–200° C.

$R_f$ value: 0.41 (silica gel; petroleum ether/ethyl acetate=1:1) Calculated: C 60.80 H 4.42 N 28.36 Found: 60.60 4.61 28.16

(38) 4-[(2,5-Difluorophenyl)amino]-6-(cyclopropylamino)-pyrimido[5,4-d]pyrimidine Melting point: 238°–240° C.

$R_f$ value: 0.43 (silica gel; petroleum ether/ethyl acetate=1:1) Calculated: C 57.32 H 3.84 N 26.73 Found: 57.57 4.05 26.23

(39) 4-[(2-Fluoro-5-methylphenyl)amino]-6-(cyclopropylamino)-pyrimido[5,4-d]pyrimidine Melting point: 200°–202° C. Calculated: C 61.92 H 4.87 N 27.08 Found: 61.99 4.99 27.00

(40) 4-[(2-Fluoro-3-trifluoromethyl-phenyl)amino]-6-(cyclopropylamino)-pyrimido[5,4-d]pyrimidine Melting point: 204°–206° C. Calculated: C 52.75 H 3.23 N 23.06 Found: 53.50 3.39 22.59

(41) 4-[(2-Fluoro-3-methyl-phenyl)amino]-6-(cyclopropylamino)-pyrimido[5,4-d]pyrimidine

(42) 4-[(2-Fluoro-5-trifluoro-phenyl)amino]-6-(cyclopropylamino)-pyrimido[5,4-d]pyrimidine Melting point: 210°–212° C.

$R_f$ value: 0.28 (silica gel; petroleum ether/ethyl acetate=2:1) Calculated: C 52.75 H 3.23 N 23.06 Found: 52.37 3.51 23.27

(43) 4-[(2,5-Difluoro-4-methyl-phenyl)amino]-6-(cyclopropylamino)-pyrimido[5,4-d]pyrimidine

(44) 4-[(2,4-Difluoro-3-methyl-phenyl)amino]-6-(cyclopropylamino)-pyrimido[5,4-d]pyrimidine

(45) 4-[(3-Nitrophenyl)amino]-6-(cyclopropylamino)-pyrimido[5,4-d]pyrimidine

Melting point: 208°–210° C.

$R_f$ value: 0.32 (silica gel; petroleum ether/ethyl acetate=1:1) Calculated: C 55.72 H 4.05 N 30.32 Found: 55.58 4.12 30.42

(46) 4-[(3-Ethynylphenyl)amino]-6-(cyclopropylamino)-pyrimido[5,4-d]pyrimidine

Melting point: 279°–281° C.

$R_f$ value: 0.43 (silica gel; petroleum ether/ethyl acetate=2:1) Calculated: C 67.53 H 4.66 N 27.79 Found: 67.48 4.76 28.14

(47) 4-(Phenylamino)-6-(morpholino)-pyrimido[5,4-d]pyrimidine

Melting point: 170°–172° C.

$R_f$ value: 0.47 (silica gel; petroleum ether/ethyl acetate 1:2) Calculated: C 62.32 H 5.23 N 27.25 Found: 62.31 5.38 27.17

(48) 4-[N-Methyl-N-(3-methylphenyl)amino]-6-(morpholino)-pyrimido[5,4-d]pyrimidine Melting point: 71°–73° C.

$R_f$ value: 0.60 (silica gel; petroleum ether/ethyl acetate 1:2) Calculated: C 64.26 H 5.99 N 24.98 Found: 64.36 6.08 24.75

(49) 4-[N-Methyl-N-phenyl-amino]-6-(morpholino)-pyrimido[5,4-d]pyrimidine

Melting point: 132°–134° C.

$R_f$ value: 0.38 (silica gel; petroleum ether/ethyl acetate= 1:2) Calculated: C 63.33 H 5.62 N 26.06 Found: 63.59 5.79 25.82

(50) 4-[(3-Cyclopropylphenyl)amino]-6-(morpholino)-pyrimido[5,4-d]pyrimidine

(51) 4-[(3-Cyano-4-hydroxyphenyl)amino]-6-(morpholino)-pyrimido[5,4-d]pyrimidine

(52) 4-[(3-Cyano-4-aminophenyl)amino]-6-(morpholino)-pyrimido[5,4-d]pyrimidine

(53) 4-[(4-Hydroxy-3-nitrophenyl)amino]-6-(morpholino)-pyrimido[5,4-d]pyrimidine

(54) 4-[(4-Amino-3-nitrophenyl)amino]-6-(morpholino)-pyrimido[5,4-d]pyrimidine

(55) 4-[(3,4-Dichlorophenyl)amino]-6-methylthio-pyrimido[5,4-d]pyrimidine

Melting point: 158°–160° C.

$R_f$ value: 0.48 (silica gel; petroleum ether/ethyl acetate= 2:1)

(56) 4-[(3-Chloro-4-fluoro-phenyl)amino]-6-methylthio-pyrimido[5,4-d]pyrimidine

Melting point: 140°–145° C. (decomposition)

$R_f$ value: 0.54 (silica gel; petroleum ether/ethyl acetate= 10:7)

This compound may be obtained in the following way: a mixture of 10 g 4-hydroxy-6-methylthio-pyrimido[5,4-d]pyrimidine, 16 ml hexamethyldisilazane, 32.5 g 3-chloro-4-fluoro-aniline and 1 g p-toluenesulphonic acid hydrate are heated at boiling point for 12 hours. Then 500 ml methanol is added and the mixture heated at boiling point for a further hour. The solvents are distilled off in a rotary evaporator, the residue is dissolved in methylene chloride, the solution is extracted with 100 ml 2N sodium hydroxide and dried over magnesium sulfate. After distilling off the solvent in a rotary evaporator the residue is triturated with 200 ml ether, filtered off and washed several times with ether.

After drying there is obtained 11.5 g (69% of theory) of the title compound with the abovementioned physical data.

(57) 4-[(3-Chloro-4-methoxy-phenyl)amino]-6-methylthio-pyrimido[5,4-d]pyrimidine Melting point: 154°–156° C.

$R_f$ value: 0.40 (silica gel; petroleum ether/ethyl acetate= 1:1)

(58) 4-[(4-Amino-3-nitro-phenyl)amino]-6-methylthio-pyrimido[5,4-d]pyrimidine

Melting point: 248°–250° C.

$R_f$ value: 0.48 (silica gel; petroleum ether/ethyl acetate/methanol=10:10:1)

(59) 4-[(4-Chloro-3-nitro-phenyl)amino]-6-methylthio-pyrimido[5,4-d]pyrimidine

Melting point: 173°–175° C.

$R_f$ value: 0.58 (silica gel; petroleum ether/ethyl acetate 1:1)

(60) 4-[(4-Amino-3-cyano-phenyl)amino]-6-methylthio-pyrimido[5,4-d]pyrimidine

Prepared from the compound of Example XVI.

Melting point: 225°–227° C.

(61) 4-[(4-Amino-3,5-dichloro-phenyl)amino]-6-methylthiopyrimido[5,4-d]pyrimidine Melting point: 195°–197° C.

$R_f$ value: 0.50 (silica gel; petroleum ether/ethyl acetate= 1:1)

(62) 4-[(4-Amino-3,5-dibromo-phenyl)amino]-6-methylthiopyrimido[5,4-d]pyrimidine Prepared from the compound of Example XVII.

Melting point: 245°–247° C.

(63) 4-[(2-Cyclopropylphenyl)amino]-6-(morpholino)-pyrimido[5,4-d]pyrimidine

Prepared from the compound of Example XV.

Melting point: 171°–173° C. Calculated: C 65.49 H 5.78 N 24.12 Found: 65.24 5.84 24.06

EXAMPLE 4

4-(Phenylamino)-pyrimido[5,4-d]pyrimidine 0.6 g of 4-(phenylamino)-2,8-dichloro-pyrimido[5,4-d] pyrimidine is added in portions to a mixture of 10 ml of hydriodic acid (67% strength) and 2.4 g of diphosphorus tetraiodide at 50° C., while stirring. Stirring is continued for 20 minutes then the mixture is poured onto ice and water and rendered alkaline with sodium hydroxide solution. The mixture is extracted three times with methylene chloride and the combined extracts are dried and concentrated. The residue is dissolved in dioxane, 0.5 g of palladium-on-charcoal (10% of palladium) is added and the mixture is heated under reflux overnight. The catalyst is filtered off, the filtrate is concentrated and the residue is purified by chromatography over an aluminium oxide column with petroleum ether/ethyl acetate (10:3).

Yield: 0.07 g (16% of theory),

Melting point: 110°–112° C.

$R_f$ value: (aluminium oxide; petroleum ether/ethyl acetate=2:1)

The following compounds are obtained analogously to Example 4:

(1) 4-[(3-Bromophenyl)amino]-pyrimido[5,4-d]pyrimidine

Melting point: 208°–210° C.

$R_f$ value: 0.30 (aluminium oxide; petroleum ether/ethyl acetate=2:1)

(2) 4-[(3-Chlorophenyl)amino]-pyrimido[5,4-d]pyrimidine

Melting point: 187°–189° C.

$R_f$ value: 0.35 (aluminium oxide; petroleum ether/ethyl acetate=10:4)

(3) 4-[(3-Trifluoromethylphenyl)amino]-pyrimido[5,4-d] pyrimidine $R_f$ value: 0.41 (aluminium oxide; petroleum ether/ethyl acetate=2:1)

Mass spectrum: $M^+=291$ (4) 4-[(3-Methylphenyl)amino]-pyrimido[5,4-d]pyrimidine Melting point: 159°–160° C.

$R_f$ value: 0.25 (silica gel; petroleum ether/ethyl acetate= 2:1)

EXAMPLE 5

| Coated tablets with 75 mg of active substance | |
|---|---|
| 1 coated tablet comprises: | |
| Active substance | 75.0 mg |
| Calcium phosphate | 93.0 mg |
| Maize starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Production:

The active substance is mixed with calcium phosphate, maize starch, polyvinylpyrrolidone, hydroxypropylmethylcellulose and half the stated amount of magnesium stearate. Pellets having a diameter of about 13 mm are produced on a tablet-making machine, and these are rubbed through a sieve of 1.5 mm mesh width on a suitable machine and mixed with the remaining amount of magnesium stearate. These granules are pressed to tablets of the desired shape on a tablet-making machine.

Core weight: 230 mg
Die: 9 mm, convex

The coated tablet cores thus produced are coated with a film which essentially comprises hydroxypropylmethylcellulose. The finished film-coated tablets are polished with beeswax. Coated tablet weight: 245 mg.

EXAMPLE 6

Tablets with 100 mg of active substance

Composition:

1 tablet comprises:

| | |
|---|---|
| Active substance | 100.0 mg |
| Lactose | 80.0 mg |
| Maize starch | 34.0 mg |
| Polyvinylpyrrolidone | 4.0 mg |
| Magnesium stearate | 2.0 mg |
| | 220.0 mg |

Production process:

The active compound, lactose and starch are mixed and the mixture is moistened uniformly with an aqueous solution of the polyvinylpyrrolidone. After the moist mass has been sieved (2.0 mm mesh width) and dried in a tray drying cabinet at 50° C., it is sieved again (1.5 mm mesh width) and the lubricant is admixed. The ready-to-press mixture is processed to tablets.

| | | |
|---|---|---|
| Tablet weight: | 220 mg | |
| Diameter: | 10 mm, | biplanar with a bevelled edge on both sides and a dividing groove on one side. |

EXAMPLE 7

Tablets with 150 mg of active substance

Composition:

1 tablet comprises:

| | |
|---|---|
| Active substance | 150.0 mg |
| Powdered lactose | 89.0 mg |
| Maize starch | 40.0 mg |
| Colloidal silica gel acid | 10.0 mg |
| Polyvinylpyrrolidone | 10.0 mg |
| Magnesium stearate | 1.0 mg |
| | 300.0 mg |

Production:

The active substance is mixed with lactose, maize starch and silicic acid and the mixture is moistened with a 20% strength aqueous polyvinylpyrrolidone solution and passed through a sieve of 1.5 mm mesh width. The granules are dried at 45° C., rubbed again through the same sieve and mixed with the stated amount of magnesium stearate. Tablets are pressed from the mixture.

| | |
|---|---|
| Tablet weight: | 300 mg |
| Die: | 10 mm, flat |

EXAMPLE 8

Hard gelatin capsules with 150 mg of active substance 1 capsule comprises:

| | | |
|---|---|---|
| Active compound | | 150.0 mg |
| Dried maize starch | about | 180.0 mg |
| Powdered lactose | about | 87.0 mg |
| Magnesium stearate | | 3.0 mg |
| | about | 420.0 mg |

Production:

The active compound is mixed with the auxiliaries and the mixture is passed through a sieve of 0.75 mm mesh width and mixed homogeneously in a suitable apparatus. The final mixture is introduced into size 1 hard gelatin capsules.

| | |
|---|---|
| Capsule filling: | about 320 mg |
| Capsule shell: | hard gelatin capsule, size 1. |

EXAMPLE 9

Suppositories with 150 mg of active substance 1 suppository comprises:

| | |
|---|---|
| Active compound | 150.0 mg |
| Polyethylene glycol 1500 | 550.0 mg |
| Polyethylene glycol 6000 | 460.0 mg |
| Polyoxyethylenesorbitan monostearate | 840.0 mg |
| | 2000.0 mg |

Production:

After the suppository mass has been melted, the active compound is distributed homogeneously therein and the melt is poured into precooled moulds.

EXAMPLE 10

Suspension with 50 mg of active substance 100 ml of suspension comprise:

| | |
|---|---|
| Active compound | 1.00 g |
| Carboxymethylcellulose Na salt | 0.10 g |
| Methyl p-hydroxybenzoate | 0.05 g |
| Propyl p-hydroxybenzoate | 0.01 g |
| Cane sugar | 10.00 g |
| Glycerol | 5.00 g |
| Sorbitol solution, 70% strength | 20.00 g |
| Aroma | 0.30 g |
| Distilled water to | 100 ml |

Production:

The distilled water is heated to 70° C. Methyl and propyl p-hydroxybenzoate and glycerol and carboxymethylcellulose sodium salt are dissolved therein, while stirring. The mixture is cooled to room temperature, and the active compound is added and dispersed homogeneously, while stirring. After addition and dissolving of the sugar, the sorbitol solution and the aroma, the suspension is evacuated while stirring to remove the air. 5 ml of suspension comprise 50 mg of active compound.

EXAMPLE 11

Ampoules with 10 mg of active substance

Composition:

| Active compound | 10.0 mg |
|---|---|
| 0.01 N hydrochloric acid s.q. | |
| Doubly distilled water to | 2.0 ml |

Production:

The active substance is dissolved in the required amount of 0.01 N HCl and the solution is rendered isotonic with sodium chloride, subjected to sterile filtration and introduced into 2 ml ampoules.

EXAMPLE 12

Ampoules with 50 mg of active substance

Composition:

| Active compound | 50.0 mg |
|---|---|
| 0.01 N hydrochloric acid s.q. | |
| Doubly distilled water to | 10.0 ml |

Production:

The active substance is dissolved in the required amount of 0.01 N HCl and the solution is rendered isotonic with sodium chloride, subjected to sterile filtration and introduced into 10 ml ampoules.

What is claimed is:

1. A pyrimido[5,4-d]pyrimidines of the general formula (I)

in which $R_a$ is a hydrogen atom or an alkyl group, $R_b$ is a phenyl group which is substituted by the radicals $R_1$ to $R_3$, wherein $R_1$ and $R_2$, which can be identical or different, are each a hydrogen, fluorine, chlorine, bromine or iodine atom, a $C_{1-6}$-alkyl, hydroxyl or $C_{1-6}$alkoxy group, a $C_{3-7}$-cycloalkyl or $C_{4-7}$-cycloalkoxy group, each of which can be substituted by one or two alkyl groups or by an aryl group, a $C_{2-5}$-alkenyl or $C_{3-5}$-alkenyloxy group which is optionally substituted by an aryl group, wherein the vinyl part cannot be linked to the oxygen atom, a $C_{2-5}$-alkynyl or $C_{3-5}$-alkynyloxy group which is optionally substituted by an aryl group, wherein the ethynyl part cannot be linked to the oxygen atom, an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphinyl, trifluoromethylsulphonyl, arylsulphenyl, arylsulphinyl, arylsulphonyl, aralkylsulphenyl, aralkylsulphinyl or aralkylsulphonyl group, a methyl or methoxy group which is substituted by 1 to 3 fluorine atoms, a $C_{2-4}$-alkyl or $C_{2-4}$-alkoxy group which is substituted by 1 to 5 fluorine atoms, a nitro, amino, alkylamino, dialkylamino, $C_{3-7}$-cycloalkylamino, N-alkyl-$C_{3-7}$-cycloalkylamino, arylamino, N-alkylarylamino, aralkylamino or N-alkyl-aralkylamino group, a 4- to 7-membered alkylenimino group which is optionally substituted by 1 to 4 alkyl groups, wherein, in the abovementioned 5- to 7-membered alkylenimino groups, in each case one or two methylene groups adjacent to the nitrogen atom can in each case be replaced by a carbonyl group, or in the abovementioned 6- to 7-membered alkylenimino groups, a methylene group in the 4-position can be replaced by an oxygen or sulphur atom or by a sulphinyl, sulphonyl, imino, N-alkyl-imino, N-alkyl-carbonyl-imino, N-alkylsulphonyl-imino, N-aryl-imino or N-aralkyl-imino group, an (alkylenimino)carbonyl or (alkylenimino)sulphonyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino, N-alkyl-imino, N-alkylcarbonyl-imino, N-alkylsulphonyl-imino, N-aryl-imino or N-aralkyl-imino group, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-aryl-sulphonylamino, aralkylcarbonylamino, N-alkylaralkylcarbonylamino, aralkylsulphonylamino, N-alkylaralkylsulphonylamino, perfluoroalkylsulphonylamino, N-alkylperfluoroalkylsulphonylamino, alkylcarbonyl, arylcarbonyl, aralkylcarbonyl, aryl-hydroxymethyl, aralkyl-hydroxymethyl, carboxyl, alkoxycarbonyl, aralkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkylaralkylaminocarbonyl, N-hydroxy-aminocarbonyl, N-hydroxyalkylaminocarbonyl, N-alkoxy-aminocarbonyl, N-alkoxyalkylaminocarbonyl, cyano, azido, N-cyano-amino or N-cyanoalkylamino group, a sulpho, alkoxysulphonyl, aminosulphonyl, alkylaminosulphonyl, dialkylaminosulphonyl, arylaminosulphonyl, N-alkylarylaminosulphonyl, aralkylaminosulphonyl or N-alkylaralkylaminosulphonyl group, a phosphono, O-alkyl-phosphono, O,O'-dialkyl-phosphono, O-aralkyl-phosphono or O,O'-diaralkyl-phosphono group, an alkyl or alkoxy group which is substituted by $R_4$, wherein $R_4$ is a hydroxyl, alkoxy, aryloxy, aralkoxy, amino, alkylamino, dialkylamino, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, carboxyl, alkoxycarbonyl, aminocarbonyl, alkylaminocarbonyl, dialkylaminocarbonyl or cyano group, a 4- to 7-membered alkylenimino group which is optionally substituted by 1 to 4 alkyl groups, wherein, in the abovementioned 5- to 7-membered alkylenimino groups, in each case one or two methylene groups adjacent to the nitrogen atom can be replaced by a carbonyl group, or in the abovementioned 6- to 7-membered alkylenimino groups, a methylene group in the 4-position can be replaced by an oxygen or sulphur atom or by a sulphinyl, sulphonyl, imino, N-alkyl-imino, N-alkylcarbonyl-imino, N-alkylsulphonylimino, N-aryl-imino or N-aralkyl-imino group, or an (alkylenimino)carbonyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino, N-alkyl-imino, N-alkylcarbonyl-imino, N-alkylsulphonyl-imino, N-aryl-imino or N-aralkyl-imino group, $R_3$ is a hydrogen, fluorine, chlorine or bromine atom, an alkyl, alkoxy or trifluoromethyl group or $R_2$ together with $R_3$, if these are bonded to adjacent carbon atoms, is a methylenedioxy group which is optionally substituted by one or two alkyl groups, an n-$C_{3-6}$-alkylene group which is optionally substituted by one or two alkyl groups, or a 1,3-butadiene-1,4-diylene group which is optionally substituted by one or two fluorine, chlorine, bromine or iodine atoms or by one or two hydroxyl, alkyl, alkoxy, trifluoromethyl or cyano groups, wherein the substituents can be identical or different, or $R_a$ together with $R_1$, if $R_1$ is in the o-position relative to the nitrogen atom which is substituted by $R_a$, is an n-$C_{2-4}$-alkylene group which is optionally substituted by one or two alkyl groups, and $R_c$ is $C_{3-7}$-cycloalkyl, $C_{3-7}$-cycloalkyl-$C_{1-3}$-alkyl, aralkyl, hydroxyl, aryloxy, aralkoxy, mercapto, $C_{1-8}$-alklsulphenyl, $C_{1-8}$-alkylsulphinyl, $C_{1-8}$-alkylsulphonyl, $C_{4-7}$cycloalkylsulphenyl, $C_{4-7}$-cycloalkylsulphinyl, $C_{4-7}$-cycloalkylsulphonyl, $C_{3-7}$-cycloalkyl-$C_{1-3}$-alkylsulphenyl, $C_{3-7}$-cycloalkyl-$C_{1-3}$-alkylsulphinyl, $C_{3-7}$-cycloalkyl-$C_{1-3}$-alkylsulphonyl, arylsulphenyl, arylsulphinyl, arylsulphonyl, aralkylsulphenyl, aralkylsulphinyl or aralkylsulphonyl group, a $C_{1-8}$-alkoxy group substituted by an alkoxycarbonyl, cyano, carboxyl, aminocarbonyl, alkylaminocarbonyl or dialkylaminocarbonyl group, a $C_{2-8}$-alkoxy group substituted by a hydroxyl, alkoxy, hydroxy-$C_{2-4}$-alkylamino, amino, alkylamino, dialkylamino, alkylcarbonylamino, N-alkyl-N-(alkylcarbonyl)amino, alkylsulphonylamino, N-alkyl-N-(alkylsulphonyl)amino, alkoxycarbonylamino or N-alkyl-N-(alkoxycarbonyl)amino group, by a 5- to 7-membered alkylenimino group which is optionally substituted by 1 to 4 alkyl groups, wherein, in the abovementioned 5- to 7-membered alkylenimino groups, in each case one or two methylene groups adjacent to the nitrogen atom can be replaced by a carbonyl group, and additionally in the abovementioned 6- to 7-membered alkylenimino groups, a methylene group in the 4-position can be replaced by an oxygen or sulphur atom or by a carbonyl, sulphinyl, sulphonyl, imino, N-alkyl-imino, N-alkylcarbonyl-imino, N-formyl-imino, N-dialkylaminocarbonyl-imino, N-alkoxy-carbonyl-imino, N-alkylsulphonyl-imino, N-aryl-imino or N-aralkyl-imino group, a $C_{3-8}$-alkoxy group substituted by two hydroxyl or alkoxy groups, a $C_{1-8}$-alkoxy group substituted by a $C_{3-7}$-cycloalkyl group wherein in each case the cycloalkyl residue can be substituted by 1 to 4 alkyl groups, and wherein, in the abovementioned $C_{4-7}$-cycloalkyl residues, in each case a methylene group can be replaced by an oxygen or sulphur atom or by a carbonyl, sulphinyl, sulphonyl, imino, N-alkyl-imino, N-alkylcarbonylimino, N-alkoxycarbonyl-imino, N-alkylsulphonyl-imino, N-arylimino or N-aralkyl-imino group, a $C_{4-7}$-cycloalkoxy group which is optionally substituted by one or two hydroxyl groups or by an alkoxy, alkoxycarbonyl, cyano, carboxyl, amino-carbonyl, alkylaminocarbonyl, dialkylaminocarbonyl, hydroxy-$C_{2-4}$-alkylamino, amino, alkylamino, dialkylamino, alkylcarbonyl-amino, N-alkyl-N-(alkylcarbonyl)amino, alkylsulphonylamino, N-alkyl-N-(alkylsulphonyl)amino, alkoxycarbonylamino or N-alkyl-N-(alkoxycarbonyl)amino group, wherein, in the abovementioned $C_{5-7}$-cycloalkoxy groups, in each case a methylene group can be replaced by an oxygen or sulphur atom or by a sulphinyl, sulphonyl, imino, N-alkyl-imino, N-alkylcarbonyl-imino, N-alkoxycarbonyl-imino, N-alkylsulphonyl-imino, N-aryl-imino or N-aralkyl-imino group, a $C_{3-8}$-alkenyloxy group which is optionally substituted by an aryl group or $C_{3-7}$-cycloalkyl group, wherein the vinyl part cannot be linked to the oxygen atom, a $C_{3-8}$-alkynyloxy group which is optionally substituted by an aryl group or $C_{3-7}$-cycloalkyl group, wherein the ethynyl part cannot be linked to the oxygen atom, a 4- to 8-membered alkylenimino group which is optionally substituted by 1 to 4 alkyl groups or 1 to 2 aryl groups, and which can additionally be substituted by the radical $R_5$, wherein $R_5$ is an aryl, aralkyl, carboxyl, alkoxycacarbonyl, aminocarbonyl, alkylaminocarbonyl, dialkylaminocarbonyl, cyano, hydroxyl, alkoxy, aryloxy, aralkoxy, alkylcarbonyloxy, arylcarbonyloxy, amino, alkylamino, hydroxy-$C_{2-4}$-alkylamino, dialkylamino, cyano-amino, formylamino, N-(alkyl)-N-(hydroxy-$C_{2-4}$-alkyl)amino or bis-(hydroxy-$C_{2-4}$-alkyl)amino group, an (alkylenimino)carbonyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino, N-alkyl-imino, N-alkylcarbonyl-imino, N-alkylsulphonyl-imino, N-aryl-imino or N-aralkyl-imino group, a 4- to 7-membered alkylenimino group which is optionally substituted by 1 to 4 alkyl groups or a hydroxyalkyl group, wherein, in the abovementioned 5- to 7-membered alkylenimino groups, in each case one or two methylene groups adjacent to the nitrogen atom can be replaced by a carbonyl group, a 6- or 7-membered alkyleneimino group which is optionally substituted by 1 to 4 alkyl groups or a hydroxyalkyl group, whereby in each case a methylene group in the 4-position of the alkyleneimino residue is replaced by an oxygen or sulphur atom or by a carbonyl, sulphinyl, sulphonyl, imino, N-alkyl-imino, N-alkylcarbonylimino, N-alkyl-sulphonylimino, N-aryl-imino or N-aralkyl-imino group, and additionally in the alkyleneimino residue of the abovementioned groups in each case one or two of the methylene groups adjacent to the nitrogen atoms can be replaced by a carbonyl group, a 4- to 7-membered alkylenimino group which is substituted by a hydroxyl, alkoxy, amino, alkylamino, dialkylamino, alkylcarbonylamino, N-alkyl-alkylcarbonylamino, alkylsulphonylamino, N-alkyl-alkylsulphonyl-amino or hydroxyalkyl group, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group, a $(NR_7R_8)CONR_6$— or $(NR_7R_8)SO_2NR_6$— group, in which $R_6$, $R_7$ and $R_8$, which can be identical or different, are each a hydrogen atom or an alkyl group or $R_6$ and $R_7$ together are an n-$C_{2-4}$-alkylene group and $R_8$ is a hydrogen atom or an alkyl group, a carboxyalkyl, alkoxycarbonylalkyl, aminocarbonylalkyl, alkylaminocarbonylalkyl or dialkylaminocarbonylalkyl group, an (alkylenimino)carbonylalkyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino or N-alkyl-imino group, a (carboxyalkyl)oxy, (alkoxycarbonylalkyl)oxy, (aminocarbonylalkyl)oxy, (alkylaminocarbonylalkyl)oxy or (dialkylaminocarbonylalkyl)oxy group, an [(alkylenimino)carbonylalkyl]oxy group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino or N-alkyl-imino group, a cyanoalkyl, hydroxyalkyl, alkoxyalkyl, aryloxyalkyl, aminoalkyl, alkylaminoalkyl or dialkylaminoalkyl group, an (alkylenimino)alkyl group which has in each case 4 to 7 ring atoms in the alkylenimino part and is optionally substituted by 1 to 4 alkyl groups, wherein, in the abovementioned 6- to 7-membered alkylenimino parts, in each case a methylene group in the 4-position can be replaced by an oxygen or sulphur atom or by a sulphinyl, sulphonyl, imino or N-alkyl-imino group, an alkylcarbonylaminoalkyl, N-alkyl-alkylcarbonylaminoalkyl, alkylsulphonylaminoalkyl, N-alkyl-alkylsulphonylaminoalkyl, arylcarbonylaminoalkyl, N-alkyl-arylcarbonylaminoalkyl, arylsulphonylaminoalkyl, N-alkyl-arylsulphonylaminoalkyl, alkylsulphenyl, alkylsulphinyl, alkylsulphonyl, arylsulphenyl, arylsulphinyl, arylsulphonyl, aralkylsulphenyl, aralkylsulphinyl, aralkylsulphonyl, alkylsulphenylalkyl, alkylsulphinylalkyl, alkylsulphonylalkyl, arylsulphenylalkyl, arylsulphinylalkyl or arylsulphonylalkyl group or a $C_{3-7}$-cycloalkyl group, wherein, in a $C_{5-7}$-cycloalkyl group, a methylene group can be replaced by an oxygen or sulphur atom or by a sulphinyl, sulphonyl, imino or N-alkylimino group, or $R_c$ is a 6- to 8-membered alkylenimino group which is optionally substituted by 1 to 4 alkyl groups or an aryl group and can additionally be substituted by the radical $R_5$, wherein, in the abovementioned alkylenimino groups, in each case a methylene group in the 4-position is replaced by an oxygen or sulphur atom or by a carbonyl, sulphinyl, sulphonyl, N-oxido-N-alkylimino or $R_9N$ group, wherein $R_9$ is a hydrogen atom, an alkyl, hydroxy-$C_{2-4}$-alkyl, alkoxy-$C_{2-4}$-alkyl, amino-$C_{2-4}$-alkyl, alkylamino-$C_{2-4}$-alkyl, dialkylamino-$C_{2-4}$-alkyl, (hydroxy-$C_{2-4}$-alkoxy)-$C_{2-4}$-alkyl, aminocarbonylalkyl, alkylaminocarbonylalkyl, dialkylaminocarbonylalkyl, aryl, aralkyl, formyl, alkylcarbonyl, alkylsulphonyl, arylcarbonyl, arylsulphonyl, aralkylcarbonyl, aralkylsulphonyl, alkoxycarbonyl, cyano, aminocarbonyl, alkylaminocarbonyl or dialkylaminocarbonyl group or an (alkylenimino)carbonyl group which has in each case 4 to 7 ring atoms in the alkylenimino part, wherein, in a 6- to 7-membered alkylenimino part, a methylene group in the 4-position can be replaced by an oxygen or sulphur atom or by a sulphinyl, sulphonyl, imino or N-alkyl-imino group, or $R_c$ is a 1-pyrrolidinyl group which is optionally substituted by 1 to 4 alkyl groups and in which two hydrogen atoms on the carbon skeleton are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 2 to 4 carbon atoms if the two hydrogen atoms are on carbon atoms which are separated by an atom, wherein the abovementioned 1-pyrrolidinyl groups can additionally be substituted by the radical $R_5$, which is defined as mentioned above, a 1-piperidinyl or 1-azacyclohept-1-yl group which is optionally substituted by 1 to 4 alkyl groups and in which two hydrogen atoms on the carbon skeleton are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 1 to 4 carbon atoms if the two hydrogen atoms are on carbon atoms which are separated by an atom, or contains 1 to 3 carbon atoms if the two hydrogen atoms are on carbon atoms which are separated by two atoms, wherein the abovementioned 1-piperidinyl and 1-azacyclohept-1-yl groups can additionally be substituted by the radical $R_5$, which is defined as mentioned above, a 1-pyrrolidinyl group which is optionally substituted by 1 to 4 alkyl groups and in which two hydrogen atoms in the 3-position are substituted by a —O—$CH_2CH_2$—O— or —O—$CH_2CH_2CH_2$—O— group, a 1-piperidinyl or 1-azacyclohept-1-yl group which is optionally substituted by 1 to 4 alkyl groups and in which, in the 3-position or in the 4-position, in each case two hydrogen atoms are replaced by a —O—CH$_2$CH$_2$—O— or —O—CH$_2$CH$_2$CH$_2$—O— group, a group of the formula

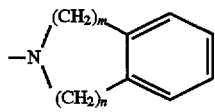

in which m and n, which can be identical or different, are the numbers 1 to 3 or m is the number 0 and n is the number 2, 3 or 4, wherein, additionally, the above benzo part can be mono- or disubstituted by fluorine, chlorine, bromine or iodine atoms or by alkyl, trifluoromethyl, hydroxyl, alkoxy or cyano groups and the above saturated cyclic imino part can be mono- or disubstituted by 1 or 2 alkyl groups, wherein the substituents can in each case be identical or different, or an ($R_{10}NR_{11}$) group, in which $R_{10}$ and $R_{11}$, which can be identical or different, are each a hydrogen atom, a $C_{1-16}$-alkyl group, which can be substituted by 1 or 2 aryl or $C_{3-7}$-cycloalkyl groups, by a carboxyl, alkoxycarbonyl, aminocarbonyl, alkylaminocarbonyl, dialkylaminocarbonyl, hydroxy-$C_{2-4}$-alkylaminocarbonyl, cyano, hydroxyl, alkoxy, aryloxy, aralkoxy, $C_{2-4}$-alkylenedioxy, alkylcarbonyloxy, arylcarbonyloxy, formylamino, amino, alkylamino or dialkylamino group, by an (alkylenimino)carbonyl group which has in each case 4 to 7 ring atoms in the alkylenimino part and is optionally substituted by 1 to 4 alkyl groups, wherein, in a 6- or 7-membered alkylenimino residue, in each case a methylene group in the 4-position can be replaced by an oxygen or sulphur atom or by a sulphinyl, sulphonyl, imino, N-alkylimino, N-alkylcarbonyl-imino, N-alkylsulphonyl-imino, N-arylimino or N-aralkyl-imino group, by a 4- to 7-membered alkylenimino group which is optionally substituted by 1 to 4 alkyl groups, wherein, in the abovementioned 6- or 7-membered alkylenimino groups, in each case a methylene group in the 4-position can be replaced by an oxygen or sulphur atom or by a sulphinyl, sulphonyl or $R_9N$ group, wherein $R_9$ is as defined above, and additionally in the abovementioned 5- to 7-membered alkylenimino groups, in each case one or two methylene groups adjacent to the nitrogen atoms can be replaced by a carbonyl group, by an alkylsulphonylamino, N-alkyl-alkylsulphonylamino, arylcarbonylamino, N-alkyl-arylcarbonyl-amino, alkylcarbonylamino, N-alkyl-alkylcarbonylamino, arylsulphonylamino, N-alkyl-arylsulphonylamino, aralkylcarbonylamino, N-alkylaralkylcarbonylamino, aralkylsulphonylamino, N-alkyl-aralkylsulphonylamino, alkoxycarbonylamino, N-alkyl-alkoxycarbonylamino, aralkoxycarbonylamino or N-alkyl-aralkoxycarbonylamino group, by an ($R_8NR_7$)—CO—$NR_6$— or ($R_8NR_7$)—$SO_2$—$NR_6$— group, wherein $R_6$, $R_7$ and $R_8$ are as defined above, by an alkylsulphenyl, alkylsulphinyl, alkylsulphonyl, arylsulphenyl, arylsulphinyl, arylsulphonyl, aralkylsulphenyl, aralkylsulphi-nyl or aralkylsulphonyl group, by a $C_{4-7}$-cycloalkyl group which is substituted by $R_5$ and optionally additionally by 1 to 4 alkyl groups, wherein $R_5$ is as defined above, by a $C_{5-7}$-cycloalkyl group which is optionally substituted by 1 to 4 alkyl groups and in which a methylene group is replaced by an oxygen or sulphur atom or by a sulphinyl, sulphonyl, or $NR_9$ group, or by a fluorine, chlorine, bromine or iodine atom, a $C_{2-10}$-alkyl group substituted by 2 or 3 fluorine atoms, a $C_{3-10}$-alkyl group substituted by 4 or 5 fluorine atoms, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a $C_{3-10}$-alkyl group which is substituted by 2 to 5 hydroxyl or alkoxy groups, a $C_{2-6}$-alkyl group which is substituted by an aryl group and a hydroxyl group and can additionally be substituted by an amino, alkylamino, dialkylamino, hydroxyl or alkoxy group, a $C_{3-6}$-alkyl group which is substituted by an amino, alkylamino, dialkylamino, alkylcarbonylamino or alkoxycarbonylamino group and additionally by a hydroxyl or alkoxy group, an alkenyl or alkynyl group which has in each case 3 to 6 carbon atoms and is optionally substituted by an aryl group or $C_{3-7}$-cycloalkyl group, wherein the vinyl or ethynyl part cannot be linked to the nitrogen atom, a $C_{2-4}$-alkyl group which is substituted by a $C_{2-4}$-alkoxy group which is substituted in the ω-position by a hydroxyl or alkoxy group, an aryl group, a cyclopropyl group which can be substituted by 1 or 2 alkyl groups, by an aryl, carboxyl, alkoxycarbonyl, aminocarbonyl, alkylaminocarbonyl or dialkylaminocarbonyl group or by an (alkylenimino)carbonyl group which has in each case 4 to 7 ring atoms in the alkylenimino part and is optionally substituted by 1 to 4 alkyl groups, wherein, in the abovementioned 6- or 7-membered alkylenimino parts, in each case a methylene group in the 4-position can be replaced by an oxygen or sulphur atom or by a sulphinyl, sulphonyl, imino, N-alkylimino, N-alkylcarbonyl-imino, N-alkylsulphonyl-imino, N-aryl-imino or N-aralkyl-imino group, a $C_{4-7}$-cycloalkyl group which is optionally substituted by 1 to 4 alkyl groups and can additionally be substituted by $R_5$, which is as defined above, a $C_{5-7}$-cycloalkyl group which is optionally substituted by 1 to 2 alkyl groups and is additionally substituted by an N,N-dialkyl-N-oxido-amino group, a $C_{5-7}$-cycloalkenyl group which is optionally substituted by 1 to 4 alkyl groups, wherein the vinyl part cannot be linked to the nitrogen atom of the ($R_{11}NR_{10}$)— group, a $C_{4-7}$-cycloalkyl group which is optionally substituted by 1 to 4 alkyl groups and can additionally be substituted by $R_5$, wherein, in the cycloalkyl part, a methylene group is replaced by an oxygen or sulphur atom or by a sulphinyl, sulphonyl, N-alkyl-N-oxido-imino or $R_9N$ group, wherein $R_5$ and $R_9$ are as defined above, a $C_{5-7}$-cycloalkyl or $C_5$–$C_7$-cycloalkylalkyl group which is optionally substituted by 1 to 4 alkyl groups and in which in each case a methylene group in the cycloalkyl part is replaced by a carbonyl group, a cyclopentyl or cyclopentylalkyl group which is optionally substituted by 1 to 4 alkyl groups and in which in each case two hydrogen atoms in the cyclopentyl part are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 2 to 4 carbon atoms if the two hydrogen atoms are on carbon atoms which are separated by a carbon atom, wherein the abovementioned rings can additionally be substituted by the radical $R_5$, which is as defined above, a cyclohexyl, cyclohexylalkyl, cycloheptyl or cycloheptylalkyl group which is optionally substituted by 1 to 4 alkyl groups and in which in each case two hydrogen atoms in the cycloalkyl part are replaced by a straight-chain alkylene bridge, wherein this bridge contains 2 to 6 carbon atoms if the two hydrogen atoms are on the same carbon atom, or contains 1 to 5 carbon atoms if the two hydrogen atoms are on adjacent carbon atoms, or contains 1 to 4 carbon atoms if the two hydrogen atoms are on carbon atoms which are separated by a carbon atom, or contains 1 to 3 carbon atoms if the two hydrogen atoms are on carbon atoms which are separated by two carbon atoms, wherein the abovementioned rings can additionally be substituted by the radical $R_5$, which is as defined above, a 3-cyclohexen-1-yl or 3-cyclohexen-1-yl-alkyl group which is optionally substituted by 1 to 4 alkyl groups and in which two hydrogen atoms in the 2,5-position in the cyclohexenyl part are replaced by an n-$C_{1-3}$-alkylene bridge, a 3-quinuclidinyl, 4-quinuclidinyl, 2-quinuclidinyl-alkyl, 3-quinuclidinyl-alkyl, 4-quinuclidinyl-alkyl, azabicyclo[2.2.1]hept-4-yl, azabicyclo[2.2.1]hept-4-yl-alkyl or adamantyl group, or $R_{10}$ is a hydrogen atom or an alkyl group and $R_{11}$ is a hydroxyl, alkoxy or cyano group, their tautomers, their stereoisomers and their salts, wherein, unless mentioned otherwise, the aryl parts mentioned in the definition of the abovementioned radicals is to be understood as meaning a phenyl group which can be in each case be monosubstituted by $R_{12}$, mono-, di- or trisubstituted by $R_{13}$ or monosubstituted by $R_{12}$ and additionally mono- or disubstituted by $R_{13}$, wherein the substituents can be identical or different, and $R_{12}$ is a cyano, carboxyl, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylcarbonylamino, N-alkyl-alkylcarbonylamino, alkylamino, dialkylamino, hydroxy-$C_{2-4}$-alkylamino, N-alkyl-(hydroxy-$C_{2-4}$-alkyl)amino, bis-(hydroxy-$C_{2-4}$-alkyl)amino, phenylalkylcarbonylamino, phenylcarbonylamino, alkylsulphonylamino, phenylalkylsulphonylamino, phenylsulphonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl, dialkylaminosulphonyl, ($R_8NR_7$)—CO—$NR_6$— or ($R_8NR_7$)—$SO_2$—$NR_6$— group, wherein $R_6$, $R_7$ and $R_8$ are as defined above, a 5- to 7-membered alkylenimino group which is optionally substituted by 1 to 4 alkyl groups or a hydroxyalkyl group, wherein, in the abovementioned 6- to 7-membered alkylenimino groups, in each case a methylene group in the 4-position can be replaced by an oxygen atom or an $R_9N$ group, wherein $R_9$ is as defined above, a 5- to 7-membered alkylenimino group which is optionally substituted by 1 to 4 alkyl groups or a hydroxyalkyl group, wherein in each case one or two methylene groups adjacent to the nitrogen atom are in each case replaced by a carbonyl group, and $R_{13}$ is an alkyl, hydroxyl or alkoxy group or a fluorine, chlorine, bromine or iodine atom, wherein two radicals $R_{13}$, if these are bonded to adjacent carbon atoms, can also be an alkylene group having 3 to 6 carbon atoms, a 1,3-butadiene-1,4-diylene group or a methylenedioxy group, and, unless mentioned otherwise, the abovementioned alkyl, alkylene and alkoxy parts in each case contain 1 to 4 carbon atoms.

2. Pyrimido[5,4-d]pyrimidines of the general formula I according to claim 1, with the proviso that, unless mentioned otherwise, each carbon atom in the alkylene or cycloalkylene parts mentioned in claim 1 which is bonded to a nitrogen, oxygen or sulphur atom cannot be bonded to a further halogen, nitrogen, oxygen or sulphur atom, their tautomers, their stereoisomers and their salts.

3. Pyrimido[5,4-d]pyrimidines according to claim 1 or 2, in which $R_a$ is a hydrogen atom or an alkyl group, $R_b$ is a phenyl group which is substituted by the radicals $R_1$ to $R_3$, wherein $R_1$ is a hydrogen, fluorine, chlorine, bromine or iodine atom, a $C_{1-6}$-alkyl, hydroxyl or $C_{1-6}$-alkoxy group, a $C_{3-6}$-cycloalkyl or $C_{5-6}$-cycloalkoxy group, a $C_{2-5}$-alkenyl or $C_{3-5}$-alkenyloxy group, wherein the vinyl part cannot be linked to the oxygen atom, a $C_{2-5}$-alkynyl or $C_{3-5}$-alkynyloxy group, wherein the ethynyl part cannot be linked to the oxygen atom, an aryl, aryloxy, aralkyl, aralkoxy, alkylsulphenyl, alkylsulphinyl, alkylsulphonyl, alkylsulphonyloxy, trifluoromethylsulphenyl, trifluoromethylsulphonyl, arylsulphenyl, arylsulphinyl, arylsulphonyl, aralkylsulphenyl, aralkylsulphinyl or aralkylsulphonyl group, a methyl or methoxy group which is substituted by 1 to 3 fluorine atoms, a $C_{2-4}$-alkyl or $C_{2-4}$-alkoxy group which is substituted by 1 to 5 fluorine atoms, a nitro, amino, alkylamino, dialkylamino, $C_{3-6}$-cycloalkylamino, N-alkyl-$C_{3-6}$-cycloalkylamino, arylamino, N-alkylarylamino, aralkylamino or N-alkyl-aralkylamino group, a 5- to 7-membered alkylenimino group, wherein in each case one or two methylene groups adjacent to the nitrogen atom can in each case be replaced by a carbonyl group or, in the abovementioned 6- to 7-membered alkylenimino groups, a methylene group in the 4-position can be replaced by an oxygen atom or by an imino or N-alkyl-imino group, an (alkylenimino) carbonyl or (alkylenimino) sulphonyl group having in each case 5 to 7 ring atoms in the alkylenimino part, wherein, in the abovementioned 6- to 7-membered alkylenimino parts, in each case a methylene group in the 4-position can be replaced by an oxygen atom or by an imino or N-alkyl-imino group, an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, trifluoromethylsulphonylamino, N-alkyl-trifluoromethylsulphonylamino, alkylcarbonyl, arylcarbonyl, aralkylcarbonyl, carboxyl, alkoxycarbonyl, aminocarbonyl, alkylaminocarbonyl, dialkylaminocarbonyl, arylaminocarbonyl, N-alkyl-arylaminocarbonyl, aralkylaminocarbonyl, N-alkyl-aralkyl-aminocarbonyl, N-hydroxy-aminocarbonyl, N-hydroxy-alkyl-aminocarbonyl, N-alkoxy-aminocarbonyl, N-alkoxy-alkyl-aminocarbonyl, cyano, azido, N-cyano-amino or N-cyano-alkylamino group, a sulpho, aminosulphonyl, alkylaminosulphonyl, dialkylaminosulphonyl, arylaminosulphonyl, N-alkyl-arylaminosulphonyl, aralkylaminosulphonyl or N-alkyl-aralkylaminosulphonyl group, a phosphono, O-alkyl-phosphono, O,O'-dialkyl-phosphono or O,O'-diaralkyl-phosphono group, an alkyl or alkoxy group which is substituted by $R_4$, wherein $R_4$ is a hydroxyl, alkoxy, aryloxy, amino, alkylamino, dialkylamino, alkylsulphenyl, alkylsulphinyl, alkylsulphonyl, arylsulphenyl, arylsulphinyl, arylsulphonyl, carboxyl, alkoxycarbonyl, aminocarbonyl, alkylaminocarbonyl, dialkylaminocarbonyl or cyano group or an (alkylenimino)carbonyl group having in each case 5 to 7 ring atoms in the alkylenimino part, wherein, in the abovementioned 6- to 7-membered alkylenimino parts, in each case a methylene group in the 4-position can be replaced by an oxygen atom or by an imino or N-alkyl-imino group, $R_2$ is a hydrogen, fluorine, chlorine or bromine atom or an alkyl, trifluoromethyl, hydroxyl, alkoxy, amino, alkylamino, dialkylamino, alkylcarbonylamino, N-alkyl-alkylcarbonylamino, alkylsulphonylamino N-alkyl-alkylsulphonylamino, trifluoromethylsulphonylamino, N-alkyl-trifluoromethylsulphonylamino or cyano group and $R_3$ is a hydrogen, fluorine, chlorine or bromine atom or an alkyl, trifluoromethyl or alkoxy group, or $R_2$ together with $R_3$, if these are bonded to adjacent carbon atoms, is a methylenedioxy group which is optionally substituted by one or two alkyl groups, an n-$C_{3-6}$-alkylene group which is optionally substituted by one or two alkyl groups, or a 1,3-butadiene-1,4-diylene group which is optionally substituted by a fluorine, chlorine or bromine atom or by a hydroxyl, alkyl, alkoxy, trifluoromethyl or cyano group, or $R_a$ together with $R_1$, if $R_1$ is in the o-position relative to the nitrogen atom substituted by $R_a$, is an n-$C_{2-3}$-alkylene group, and $R_c$ is an aralkyl, mercapto, alkylsulphenyl, alkylsulphinyl or alkylsulphonyl group, a hydroxyl, aryloxy or aralkoxy group, a $C_{1-6}$-alkoxy group, which is substituted by an alkoxycarbonyl, cyano, carboxyl, aminocarbonyl, alkylaminocarbonyl or dialkylaminocarbonyl group, a $C_{2-6}$-alkoxy group substituted by a hydroxyl, alkoxy, hydroxy-$C_{2-4}$-alkylamino, amino, alkylamino, dialkylamino, alkylcarbonylamino, alkylsulphonylamino or alkoxycarbonylamino group, or by a 5- to 7-membered alkylenimino group which is optionally substituted by 1 to 2 alkyl groups, wherein, in the abovementioned 5- to 7-membered alkylenimino groups, in each case one or two methylene groups adjacent to the nitrogen atom can in each case be replaced by a carbonyl group, or in the abovementioned 6- to 7-membered alkylenimino groups, a methylene group in the 4-position can be replaced by an oxygen atom or by a carbonyl, imino, alkyl-imino, alkylcarbonyl-imino, alkoxycarbonyl-imino, alkylsulphonyl-imino, formyl-imino, dialkylaminocarbonyl-imino, aryl-imino or aralkyl-imino group, a $C_{3-6}$-alkoxy group substituted by two hydroxyl or alkoxy groups, an alkoxy group which is substituted by a $C_{3-7}$-cycloalkyl group wherein the cycloalkyl residue in each case can be substituted by one or two alkyl groups and wherein, in the abovementioned $C_{4-7}$-cycloalkyl residues, in each case a methylene group can be replaced by an oxygen atom, or by an imino, N-alkyl-imino, N-alkylcarbonyl-imino, N-alkoxycarbonyl-imino or N-aryl-imino group, a $C_{4-7}$-cycloalkoxy group which is optionally substituted by a hydroxyl, alkoxy, alkoxycarbonyl, cyano, carboxyl, aminocarbonyl, alkylaminocarbonyl, dialkylaminocarbonyl, hydroxy-$C_{2-4}$-alkylamino, amino, alkylamino, dialkylamino, alkylcarbonyl-amino, alkylsulphonylamino or alkoxycarbonylamino group, a $C_{5-7}$-cycloalkoxy group, wherein, in the abovementioned cyclopentyloxy group, in each case a methylene group in the 3-position, and in the abovementioned $C_{6-7}$-cycloalkoxy groups, in each case a methylene group in the 3- or 4-position is replaced by an oxygen atom or by an imino, alkyl-imino, alkylcarbonyl-imino, alkoxycarbonyl-imino, alkylsulphonyl-imino, aryl-imino or aralkyl-imino group, a $C_{3-6}$-alkenyloxy group, wherein the vinyl part cannot be linked to the oxygen atom, a $C_{3-6}$-alkynyloxy group, wherein the ethynyl part cannot be linked to the oxygen atom, a 4- to 8-membered alkylenimino group which is optionally substituted by 1 to 4 alkyl groups or an aryl group and can additionally be substituted by the radical $R_5$, wherein $R_5$ is an aryl, aralkyl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl, 4-alkyl-piperazinocarbonyl, cyano, hydroxyl, alkoxy, aryloxy, amino, alkylamino, dialkylamino, hydroxy-$C_{2-4}$-alkylamino, N-alkyl-hydroxy-$C_{2-4}$-alkylamino, di-(hydroxy-$C_{2-4}$-alkyl) amino, formylamino, cyanoamino, alkylcarbonylamino, N-alkyl-alkylcarbonylamino, alkoxycarbonylamino, N-alkyl-alkoxycarbonyl-amino, alkylsulphonylamino, N-alkyl-alkyl-sulphonylamino, arylcarbonylamino, N-alkyl-arylcarbonylamino, arylsulphonyl-amino, N-alkyl-arylsulphonylamino, carboxyalkyl, alkoxycarbonylalkyl, aminocarbonylalkyl, alkylaminocarbonylalkyl, dialkylaminocarbonylalkyl, pyrrolidinocarbonylalkyl, piperidinocarbonylalkyl, morpholinocarbonylalkyl, piperazinocarbonylalkyl, 4-alkyl-piperazinocarbonylalkyl, cyanoalkyl, hydroxyalkyl, alkoxyalkyl, aryloxyalkyl, aminoalkyl, alkylaminoalkyl, dialkylaminoalkyl, alkylcarbonylaminoalkyl, N-alkyl-alkylcarbonylaminoalkyl, alkylsulphonylaminoalkyl, N-alkyl-alkylsulphonylaminoalkyl, arylcarbonylaminoalkyl, N-alkyl-arylcarbonylaminoalkyl, arylsulphonylaminoalkyl, N-alkyl-arylsulphonylaminoalkyl, alkylsulphenyl, alkylsulphinyl, alkylsulphonyl, arylsulphenyl, arylsulphinyl, arylsulphonyl, alkylsulphenylalkyl, alkylsulphinylalkyl, alkylsulphonylalkyl, arylsulphenylalkyl, arylsulphinylalkyl, arylsulphonylalkyl, carboxyalkoxy, alkoxycarbonylalkoxy, aminocarbonylalkoxy, alkylaminocarbonylalkoxy, dialkylaminocarbonylalkoxy, pyrrolidinocarbonylalkoxy, piperidinocarbonylalkoxy, morpholinocarbonylalkoxy or an $(R_8NR_7)$—CO—$NR_6$— group, wherein, $R_6$, $R_7$ and $R_8$, which can be identical or different, are each a hydrogen atom or an alkyl group, or $R_6$ and $R_7$ together are an n-$C_{2-3}$-alkylene group and $R_8$ is a hydrogen atom or an alkyl group, a pyrrolidino, piperidino, morpholino, piperazino, 4-alkylpiperazino or 4-alkoxycarbonylpiperazino group, optionally substituted by one or two alkyl groups or a hydroxymethyl group, wherein, in the heterocyclic residue of the abovementioned groups, in each case one or two of the methylene groups adjacent to the nitrogen atoms can be replaced by a carbonyl group, or $R_c$ is a 6- to 8-membered alkylenimino group which is optionally substituted by 1 to 4 alkyl groups or by an aryl group and can additionally be substituted by the radical $R_5$, wherein, in the abovementioned alkylenimino groups, in each case a methylene group in the 4-position is replaced by an oxygen or sulphur atom or by a carbonyl, sulphinyl, sulphonyl, N-oxido-N-alkylimino or $R_9N$ group, wherein $R_9$ is a hydrogen atom or an alkyl, hydroxy-$C_{2-4}$-alkyl, alkoxy-$C_{2-4}$-alkyl, hydroxy-$C_{2-4}$-alkoxy-$C_{2-4}$-alkyl, aminocarbonylalkyl, alkylaminocarbonylalkyl, dialkylaminocarbonylalkyl, amino-$C_{2-4}$-alkyl, alkylamino-$C_{2-4}$-alkyl, dialkylamino-$C_{2-4}$-alkyl, aryl, aralkyl, formyl, alkylcarbonyl, alkylsulphonyl, arylcarbonyl, arylsulphonyl, aralkylcarbonyl, aralkylsulphonyl, alkoxycarbonyl, cyano, aminocarbonyl, alkylaminocarbonyl or dialkylaminocarbonyl group, or $R_c$ is a 1-pyrrolidinyl group which is optionally substituted by 1 or 2 alkyl groups and in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, a 1-piperidinyl or 1-azacyclohept-1-yl group which is optionally substituted by 1 or 2 alkyl groups and in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, or contains 1 or 2 carbon atoms if the two hydrogen atoms are on carbon atoms which are separated by two atoms, a 1-pyrrolidinyl group in which two hydrogen atoms in the 3-position are replaced by a —O—$CH_2CH_2$—O— or —O—$CH_2CH_2CH_2$—O— group, a 1-piperidinyl or 1-azacyclohept-1-yl group in which two hydrogen atoms in the 3-position or in the 4-position are replaced by a —O—$CH_2CH_2$—O— or —O—$CH_2CH_2CH_2$—O— group, a 2-isoindolinyl, 1,2,3,4-tetrahydro-isoquinolin-2-yl or 2,3,4,5-tetrahydro-1H-3-benzazepin-3-yl group, wherein the benzo part of the abovementioned groups can in each case be substituted by a fluorine, chlorine, bromine or iodine atom, by a trifluoromethyl group or by one or two alkyl or alkoxy groups, or a $(R_{10}NR_{11})$— group, in which $R_{10}$ is a hydrogen atom or a $C_{1-8}$-alkyl group, which can be substituted from position 2 by a hydroxyl or alkoxy group, $R_{11}$ is a hydrogen atom, a $C_{1-10}$-alkyl group, which can be substituted by an aryl, $C_{3-7}$-cycloalkyl, hydroxyl, alkoxy, aryloxy, carboxyl, alkoxycarbonyl, aminocarbonyl, alkylaminocarbonyl, dialkylaminocarbonyl, hydroxy-$C_{2-4}$-alkylaminocarbonyl, cyano, formylamino, amino, alkylamino or dialkylamino group, by a pyrrolidinocarbonyl, piperidinocarbonyl, morpholinocarbonyl, piperazinocarbonyl or 4-alkyl-piperazinocarbonyl group, by a 5- to 7-membered alkylenimino group which is optionally substituted by 1 or 2 alkyl groups, wherein, in the abovementioned 6- or 7-membered alkylenimino residues, in each case a methylene group in the 4-position can be replaced by an oxygen or sulphur atom or by a sulphinyl, sulphonyl or $R_9N$ group, wherein $R_9$ is as defined above, by a pyrrolidino, piperidino, piperazino or 4-alkylpiperazino group, wherein in each case one or two of the methylene groups adjacent to the nitrogen atoms are replaced by a carbonyl group, by an alkylcarbonylamino, N-alkyl-alkylcarbonylamino, alkylsulphonylamino, N-alkyl-alkylsulphonylamino, arylcarbonylamino, N-alkyl-arylcarbonylamino, arylsulphonylamino, N-alkyl-arylsulphonylamino, aralkylcarbonylamino, N-alkyl-aralkylcarbonylamino, aralkylsulphonylamino, N-alkyl-aralkylsulphonylamino, alkoxycarbonylamino or N-alkyl-alkoxycarbonylamino group, by an $(R_8NR_7)$—CO—$NR_6$— group, wherein $R_6$ to $R_8$ are as defined above, by an alkylsulphenyl, alkylsulphinyl, alkylsulphonyl, arylsulphenyl, arylsulphinyl, arylsulphonyl, aralkylsulphenyl, aralkylsulphinyl or aralkylsulphonyl group or by a $C_{5-7}$-cycloalkyl group in which a methylene group is replaced by an oxygen atom or by an imino or alkylimino group, a $C_{2-4}$-alkyl group substituted by a chlorine atom or by one to three fluorine atoms, a methyl group which is substituted by a 1,4,7,10-tetraoxacyclododecyl, 1,4,7,10,13- pentaoxacyclopentadecyl or a 1,4,7,10,13,16-hexaoxacyclooctadecyl group, a $C_{3-10}$-alkyl group which is substituted by 2 to 5 hydroxyl groups, a $C_{2-6}$-alkyl group which is substituted by a hydroxyl and additionally by an aryl group and which can optionally additionally be substituted by a hydroxyl or alkoxy group, a $C_{3-6}$-alkyl group which is substituted by a hydroxyl and additionally by an amino, alkylamino or dialkylamino group, an alkenyl or alkynyl group which has in each case 3 to 6 carbon atoms and is optionally substituted by an aryl group, wherein the vinyl or ethynyl part cannot be linked to the nitrogen atom, a $C_{2-4}$-alkyl group, which is substituted by a $C_{2-4}$-alkoxy group, which is substituted in the e-position by a hydroxyl or alkoxy group, an aryl group, a cyclopropyl group, which can be substituted by 1 or 2 alkyl groups or by an aryl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group, a $C_{4-7}$-cycloalkyl group which is optionally substituted by 1 or 2 alkyl groups and can additionally be substituted by $R_5$, wherein $R_5$ is as defined above, a $C_{5-7}$-cycloalkyl group which is optionally substituted by 1 or 2 alkyl groups and is additionally substituted by an N,N-dialkyl-N-oxido-amino group, a $C_{5-7}$-cycloalkenyl group which is optionally substituted by 1 or 2 alkyl groups, wherein the vinyl part cannot be linked to the nitrogen atom of the $(R_{11}NR_{10})$— group, a $C_{5-7}$-cycloalkyl group which is optionally substituted by 1 or 2 alkyl groups, wherein, in the cycloalkyl part, in each case a methylene group is replaced by an oxygen or sulphur atom or by a sulphinyl, sulphonyl, N-alkyl-N-oxido-imino or $R_9N$ group, wherein $R_9$ is as defined above, a $C_{5-7}$-cycloalkyl group which is optionally substituted by 1 to 4 alkyl groups and in which in each case a methylene group is replaced by a carbonyl group, a $C_{4-7}$-cycloalkylmethyl group which is optionally substituted by 1 or 2 alkyl groups and is additionally substituted in the cycloalkyl part by $R_5$, wherein $R_5$ is defined as mentioned above, a cyclopentyl or cyclopentylalkyl group which is optionally substituted by 1 to 4 alkyl groups and in which in each case two hydrogen atoms in the cyclopentyl part are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by a carbon atom, a cyclohexyl, cyclohexylalkyl, cycloheptyl or cycloheptylalkyl group which is optionally substituted by 1 to 4 alkyl groups and in which in each case two hydrogen atoms in the cycloalkyl part are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by a carbon atom, or contains 1 or 2 carbon atoms if the two hydrogen atoms are on carbon atoms which are separated by two carbon atoms, a 5-norbornen-2-yl or 5-norbornen-2-yl-alkyl group which is optionally substituted by 1 to 4 alkyl groups, a 3-quinuclidinyl, 4-quinuclidinyl, 3-quinuclidinyl-alkyl, 4-quinuclidinyl-alkyl, azabicyclo[2.2.1]hept-4-yl, azabicyclo[2.2.1]hept-4-yl-alkyl or adamantyl group, or $R_{10}$ is a hydrogen atom or an alkyl group and $R_{11}$ is a hydroxyl or alkoxy group, their tautomers, their stereoisomers and their salts, wherein, unless mentioned otherwise, the aryl parts mentioned in the definition of the abovementioned radicals are to be understood as meaning a phenyl group, which can in each case be monosubstituted by $R_{12}$, mono-, di- or trisubstituted by $R_{13}$ or monosubstituted by $R_{12}$ and additionally mono- or disubstituted by $R_{13}$, wherein the substituents can be identical or different, and $R_{12}$ is a cyano, carboxyl, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylamino, hydroxy-$C_{2-4}$-alkylamino, N-alkyl-hydroxy-$C_{2-4}$-alkylamino, di(hydroxy-$C_{2-4}$-alkyl) amino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl or dialkylaminosulphonyl group, a 5- to 7-membered alkylenimino group which is optionally substituted by 1 to 2 alkyl groups or a hydroxyalkyl group, wherein, in the abovementioned 6- to 7-membered alkylenimino groups, in each case a methylene group in the 4-position can be replaced by an oxygen atom or an $R_9N$ group, wherein a 5- to 7-membered alkylenimino group which is optionally substituted by i to 2 alkyl groups or a hydroxyalkyl group, wherein in each case one or two methylene groups adjacent to the nitrogen atom are replaced by in each case a carbonyl group, an $(R_8NR_7)$—CO—$NR_6$— group, wherein $R_6$ to $R_8$ are defined as mentioned above, $R_{13}$ is an alkyl, hydroxyl or alkoxy group or a fluorine, chlorine, bromine or iodine atom, wherein two radicals $R_{13}$, if these are bonded to adjacent carbon atoms, can also be an alkylene group having 3 to 6 carbon atoms, a 1,3-butadiene-1,4-diylene group or a methylenedioxy group, and, unless mentioned otherwise, the abovementioned alkyl, alkylene and alkoxy parts in each case contain 1 to 4 carbon atoms and, unless mentioned otherwise, each carbon atom in the abovementioned alkylene or cycloalkylene parts which is bonded to a nitrogen, oxygen or sulphur atom cannot be bonded to a further halogen, nitrogen, oxygen or sulphur atom.

4. The pyrimido[5,4-d]pyrimidine according to claim 1 or claim 2, in which $R_a$ is a hydrogen atom or an alkyl group, $R_b$ is a phenyl group which is substituted by the radicals $R_1$ to $R_3$, wherein $R_1$ is a hydrogen, fluorine, chlorine, bromine or iodine atom, an alkyl, hydroxyl, alkoxy, $C_{3-6}$-cycloalkyl or $C_{5-6}$-cycloalkoxy group, an ethoxy group which is substituted in the 2-position by a hydroxyl, alkoxy or phenoxy group, a $C_{2-5}$-alkenyl or $C_{3-5}$-alkenyloxy group, wherein the vinyl part cannot be linked to the oxygen atom, a $C_{2-5}$-alkynyl or $C_{3-5}$-alkynyloxy group, wherein the ethynyl part cannot be linked to the oxygen atom, a phenyl, phenoxy, phenylalkyl, phenylalkoxy, alkoxyalkyl, phenoxyalkyl, carboxyalkyl, alkoxycarbonylalkyl, aminocarbonylalkyl, alkylaminocarbonylalkyl, dialkylaminocarbonylalkyl, cyanoalkyl, alkylsulphenyl, alkylsulphinyl, alkylsulphonyl, alkylsulphonyloxy, trifluoromethylsulphenyl, trifluoromethylsulphonyl, nitro, amino, alkylamino, dialkylamino, pyrrolidino, piperidino, morpholino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino, alkylcarbonyl, carboxyl, alkoxycarbonyl, aminocarbonyl, alkylaminocarbonyl, dialkylaminocarbonyl, pyrrolidinocarbonyl, piperidinocarbonyl, morpholinocarbonyl or cyano group, a methyl or methoxy group which is substituted by 1 to 3 fluorine atoms, an ethyl or ethoxy group which is substituted by 1 to 5 fluorine atoms, $R_2$ is a hydrogen, fluorine, chlorine or bromine atom or an alkyl, trifluoromethyl, amino, alkylamino, dialkylamino, alkylcarbonylamino, alkylsulphonylamino, trifluoromethylsulphonylamino, hydroxyl or alkoxy group, $R_3$ is a hydrogen, fluorine, chlorine or bromine atom or an alkyl group, or $R_2$ together with $R_3$, if these are bonded to adjacent carbon atoms, is a methylenedioxy or n-$C_{3-6}$-alkylene group or a 1,3-butadiene-1,4-diylene group which is optionally substituted by a fluorine, chlorine or bromine atom or by an alkyl, alkoxy or trifluoromethyl group and $R_c$ is a mercapto, alkylsulphenyl, alkylsulphinyl or alkyl-sulphonyl group, a hydroxyl, phenoxy or phenyl-$C_{1-2}$-alkoxy group, a $C_{2-4}$-alkoxy group, which is substituted by a hydroxyl, alkoxy, (2-hydroxyethyl)amino, dialkylamino, morpholino, 1-pyrrolidinyl, 1-piperidinyl, 4-methyl-1-piperazinyl, 4-acetyl-1-piperazinyl, 4-methylsulphonyl-1-piperazinyl, 4-methoxycarbonyl-1-piperazinyl, 4-formyl-1-piperazinyl or 4-dimethylaminocarbonyl-1-piperazinyl group, a $C_{3-4}$-alkoxy group, which is substituted by two hydroxyl groups, a $C_{1-2}$-alkoxy group, which is substituted by a $C_{3-7}$-cycloalkyl group which is optionally substituted by one or two methyl groups, wherein, in the abovementioned $C_{4-6}$-cycloalkyl groups, in each case a methylene group can be replaced by an oxygen atom, a $C_{4-6}$-cycloalkoxy group which is optionally substituted by a hydroxyl, dialkylamino, alkoxy, carboxyl, alkoxycarbonyl, aminocarbonyl, alkylaminocarbonyl, dialkylaminocarbonyl, alkylcarbonylamino, alkylsulphonylamino or alkoxycarbonylamino group, a cyclopentyloxy group in which the methylene group in the 3-position is replaced by an oxygen atom or by an alkylimino group, a cyclohexyloxy group in which the methylene group in the 3- or or 4-position is replaced by an oxygen atom or by an alkylimino, alkylcarbonyl-imino, alkoxycarbonyl-imino or alkylsulphonyl-imino group, an allyloxy or propargyloxy group which is optionally substituted by one or two methyl groups, a 1-azetidinyl group, a 1-pyrrolidinyl group, which can be substituted by 1 to 2 alkyl groups, by a phenyl, carboxyl, hydroxyalkyl, aminoalkyl, alkylaminoalkyl, dialkylaminoalkyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group or in the 3-position also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino, N-alkyl-dialkylaminocarbonylamino or cyano group, a 1-pyrrolidinyl group in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, a 1-piperidinyl group, which can be substituted by 1 to 4 alkyl groups, by a phenyl, hydroxyalkyl, aminoalkyl, alkylaminoalkyl, dialkylaminoalkyl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group or in the 3- or 4-position also by a hydroxyl, alkoxy, amino, alkylamino, dialkylamino, alkylcarbonylamino, alkoxycarbonylamino, formylamino, cyanoamino, alkyl sulphonylamino, dialkylaminocarbonylamino, N-alkyl-dialkylaminocarbonylamino or cyano group, a 1-piperidinyl group, which is substituted by 1 to 2 alkyl groups or a phenyl group and additionally by a hydroxyl group, a 1-piperidinyl group in which two hydrogen atoms in the 3-position or in the 4-position are replaced by a —O—$CH_2CH_2$—O— or —O—$CH_2CH_2CH_2$—O— group, a 1-piperidinyl group in which two hydrogen atoms on the carbon skeleton are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by an atom, or contains 1 or 2 carbon atoms if the two hydrogen atoms are on carbon atoms which are separated by two atoms, a 1-piperidinyl group which is optionally substituted by 1 or 2 alkyl groups and in which the methylene group in the 4-position is replaced by an oxygen or sulphur atom or by a carbonyl, sulphinyl, sulphonyl, imino, alkylimino, hydroxy-$C_{2-4}$-alkyl-imino, alkoxy-$C_{2-4}$-alkyl-imino, aminocarbonylalkylimino, alkylaminocarbonylalkyl-imino, dialkylaminocarbonylalkyl-imino, amino-$C_{2-4}$-alkyl-imino, alkylamino-$C_{2-4}$-alkyl-imino, dialkylamino-$C_{2-4}$-alkyl-imino, hydroxy-$C_{2-4}$-alkoxy-$C_{2-4}$-alkyl-imino, phenyl-imino, phenylalkyl-imino, alkylcarbonyl-imino, alkylsulphonyl-imino, phenylcarbonyl-imino, phenylsulphonyl-imino or N-oxido-N-alkyl-imino group, a 1-azacyclohept-1-yl group which is optionally substituted by 1 or 2 alkyl groups and in which in each case the methylene group in the 4-position can be replaced by an oxygen atom or by an imino, N-alkyl-imino, N-phenyl-imino, N-phenylalkyl-imino, N-alkylcarbonyl-imino, N-alkylsulphonyl-imino, N-phenylcarbonyl-imino or N-phenylsulphonyl-imino group or two hydrogen atoms in the 3,6-position can be replaced by a —$CH_2CH_2$— group, a 2-isoindolinyl, 1,2,3,4-tetrahydro-isoquinolin-2-yl or 2,3,4,5-tetrahydro-1H-3-benzazepin-3-yl group, which can in each case be substituted in the benzo part by a fluorine, chlorine or bromine atom or by an alkyl, trifluoromethyl or alkoxy group, or an ($R_{10}NR_{11}$)— group, in which $R_{10}$ is a hydrogen atom or a $C_{1-6}$-alkyl group, which can be substituted by a hydroxyl or alkoxy group from position 2, and $R_{11}$ is a hydrogen atom, a $C_{1-8}$-alkyl group, which can be substituted by a phenyl, $C_{3-6}$-cycloalkyl, hydroxyl, alkoxy, cyano, carboxyl, alkoxycarbonyl, aminocarbonyl, alkylaminocarbonyl, dialkylaminocarbonyl, (2-hydroxyethyl)aminocarbonyl, pyrrolidinocarbonyl, piperidinocarbonyl, morpholinocarbonyl, 1-piperazinylcarbonyl, 4-alkyl-1-piperazinylcarbonyl, amino, formylamino, alkylamino, dialkylamino, alkylcarbonylamino, N-alkyl-alkylcarbonylamino, alkoxycarbonylamino, N-alkyl-alkoxycarbonyl-amino, alkylsulphonylamino, N-alkyl-alkylsulphonylamino, phenylcarbonylamino, N-alkyl-phenylcarbonylamino, phenyl-sulphonylamino, N-alkyl-phenylsulphonylamino, alkylsulphenyl, alkylsulphinyl, alkylsulphonyl, 1-pyrrolidinyl, 2-oxo-1-pyrrolidinyl, 1-piperidinyl, 2-oxo-1-piperidinyl, morpholino, 1-piperazinyl, 4-alkyl-1-piperazinyl, 4-alkylcarbonyl-1-piperazinyl, 4-alkylsulphonyl-1-piperazinyl, 4-alkoxycarbonyl-1-piperazinyl, 4-cyano-1-piperazinyl, 4-formyl-1-piperazinyl, 4-aminocarbonyl-1-piperazinyl, 4-alkylaminocarbonyl-1-piperazinyl or 4-dialkylaminocarbonyl-1-piperazinyl or a ($R_8NR_7$)—CO—$NR_6$— group, wherein $R_6$ and $R_7$ together are an n-$C_{2-3}$-alkylene bridge and $R_8$ is a hydrogen atom or an alkyl group, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a 2,2,2-trifluoroethyl group, a $C_{3-5}$-alkyl group which is substituted by 2 to 5 hydroxyl groups, a $C_{3-5}$-alkyl group which is substituted by a hydroxyl and additionally by an amino group, a $C_{2-4}$-alkyl group which is substituted by a phenyl group and additionally by a hydroxyl group and which can optionally additionally be substituted by a hydroxyl or alkoxy group, an alkenyl or alkynyl group which has in each case 3 to 6 carbon atoms and is optionally substituted by a phenyl group, wherein the vinyl or ethynyl part cannot be linked to the nitrogen atom, a $C_{2-4}$-alkyl group which is substituted by a $C_{2-4}$-alkoxy group which is substituted in the ω-position by a hydroxyl or alkoxy group, a phenyl group, a phenyl group which is substituted by an alkylcarbonylamino, N-alkyl-alkylcarbonylamino, (2-hydroxyethyl)amino, di-(2-hydroxyethyl)amino, N-alkyl-(2-hydroxyethyl)amino, alkylamino or dialkylamino group or by an ($R_8NR_7$)—CO—$NR_6$— group wherein $R_6$ to $R_8$ are defined as mentioned above, a phenyl group, which is substituted by a pyrrolidino, piperidino, 2-oxo-pyrrolidino, 2-oxo-piperidino, morpholino, 1-piperazinyl or 4-alkyl-1-piperazinyl group, wherein the abovementioned heterocyclic parts can be substituted on the carbon skeleton in each case by 1 or 2 alkyl groups or by a hydroxyalkyl group, a $C_{3-7}$-cycloalkyl group which can be substituted by 1 or 2 alkyl groups or by a phenyl, carboxyl, alkoxycarbonyl, aminocarbonyl, alkylaminocarbonyl, dialkylaminocarbonyl, pyrrolidinocarbonyl, piperidinocarbonyl, morpholinocarbonyl, piperazinocarbonyl or 4-alkyl-piperazinocarbonyl group, a $C_{5-7}$-cycloalkyl group which is optionally substituted by 1 or 2 methyl groups and is substituted by a hydroxymethyl, cyano, hydroxyl, alkoxy, amino, alkylamino, dialkylamino, 2-hydroxyethylamino, di-(2-hydroxyethyl)amino, N-alkyl-2-hydroxyethylamino, N,N-dialkyl-N-oxido-amino, alkoxycarbonylamino, N-alkyl-alkoxycarbonylamino, alkylcarbonylamino, N-alkyl-alkylcarbonylamino, alkylsulphonylamino, N-alkyl-alkylsulphonylamino, phenylcarbonylamino, N-alkyl-phenylcarbonyl-amino, phenylsulphonylamino, N-alkylphenylsulphonylamino or by an ($R_8NR_7$)—CO—$NR_6$— group, wherein $R_6$ to $R_8$ are defined as mentioned above, a $C_{5-7}$-cycloalkyl group which is optionally substituted by 1 or 2 methyl groups and is substituted by a pyrrolidino, piperidino, 2-oxo-pyrrolidino, 2-oxo-piperidino, morpholino, 1-piperazinyl, 4-alkyl-1-piperazinyl or 4-alkylcarbonyl-1-piperazinyl group, wherein the abovementioned heterocyclic parts can in each case be substituted on the carbon skeleton by 1 or 2 alkyl groups or by a hydroxymethyl group, a $C_{5-7}$-cycloalkenyl group which is optionally substituted by 1 or 2 alkyl groups, wherein the vinyl part cannot be bonded to the nitrogen atom of the ($R_{11}NR_{10}$)— group, a tetrahydrofurfuryl group, a cyclopentyl group in which the methylene group in the 3-position is replaced by an oxygen atom or an imino, alkylimino, alkylcarbonylimino, formylimino, aminocarbonylimino, alkylaminocarbonylimino, alkoxycarbonylimino, alkylsulphonylimino, dialkylaminocarbonylimino or cyanoimino group, a cyclohexyl group in which the methylene group in the 3-position is replaced by an imino, alkyl-imino, alkylcarbonyl-imino, alkoxycarbonyl-imino or alkylsulphonyl-imino group, a cyclohexyl group in which the methylene group in the 4-position is replaced by an oxygen atom or an imino, N-alkyl-imino, N-phenyl-imino, N-phenylalkyl-imino, N-formyl-imino, N-alkylcarbonyl-imino, N-phenylcarbonyl-imino, N-alkoxycarbonyl-imino, N-cyano-imino, N-aminocarbonyl-imino, N-alkylamino-carbonyl-imino, N,N-dialkylaminocarbonyl-imino, N-alkyl-N-oxido-imino, N-alkylsulphonyl-imino or N-phenylsulphonylimino group, a cyclohexyl group in which a methylene group is replaced by a carbonyl group, a cyclopentyl or cyclohexyl group which is optionally substituted by 1 to 2 methyl groups and is substituted by a carboxyalkoxy, alkoxycarbonylalkoxy, aminocarbonylalkoxy, alkylaminocarbonylalkoxy, dialkylaminocarbonylalkoxy, pyrrolidinocarbonylalkoxy, piperidinocarbonylalkoxy, morpholino-carbonylalkoxy, carboxyalkyl, alkoxycarbonylalkyl, aminocarbonylalkyl, alkylaminocarbonylalkyl, dialkylaminocarbonylalkyl, pyrrolidinocarbonylalkyl, piperidinocarbonylalkyl or morpholinocarbonylalkyl group, a cyclohexylmethyl group, wherein the cyclohexyl part is substituted by a carboxyl, aminocarbonyl, alkylaminocarbonyl, dialkylaminocarbonyl, pyrrolidinocarbonyl, piperidinocarbonyl, morpholinocarbonyl, alkoxycarbonyl or hydroxymethyl group, a cyclohexyl or cyclohexylmethyl group which is optionally substituted by 1 to 3 methyl groups and in which in each case two hydrogen atoms in the cyclohexyl part are replaced by a straight-chain alkylene bridge, wherein this bridge contains 4 or 5 carbon atoms if the two hydrogen atoms are on the same carbon atom, or contains 3 or 4 carbon atoms if the two hydrogen atoms are on adjacent carbon atoms, or contains 2 or 3 carbon atoms if the two hydrogen atoms are on carbon atoms which are separated by a carbon atom, or contains 1 or 2 carbon atoms if the two hydrogen atoms are on carbon atoms which are separated by two carbon atoms, a 5-norbornen-2-yl or 5-norbornen-2-yl-methyl group which is optionally substituted by i to 3 methyl groups, a 3-quinuclidinyl, 4-quinuclidinyl or adamantyl group, or $R_{10}$ is a hydrogen atom or an alkyl group and $R_{11}$ is a hydroxyl or alkoxy group, their tautomers, their stereoisomers and their salts, wherein the abovementioned phenyl radicals in each case can be substituted by a fluorine, chlorine or bromine atom or by a nitro, alkyl, alkoxy, trifluoromethyl or hydroxyl group and, unless mentioned otherwise, the abovementioned alkyl, alkylene and alkoxy parts in each case contain 1 to 4 carbon atoms and, unless mentioned otherwise, each carbon atom in the abovementioned alkylene or cycloalkylene parts which is bonded to a nitrogen, oxygen or sulphur atom cannot be bonded to a further halogen, nitrogen, oxygen or sulphur atom.

5. The pyrimido[5,4-d]pyrimidine according to claim 1 or claim 2, in which $R_a$ is a hydrogen atom or a methyl group, $R_b$ is a 2-naphthyl, 1,2,3,4-tetrahydro-6-naphthyl or 5-indanyl group, or a phenyl group which is substituted by the radicals $R_1$ to $R_3$, wherein $R_1$ is a hydrogen, fluorine, chlorine, bromine or iodine atom, a $C_{1-4}$-alkyl, $C_{1-4}$-alkoxy, $C_{3-6}$-cycloalkyl, $C_{5-6}$-cycloalkoxy, cyano, methoxycarbonyl, ethoxycarbonyl, ethynyl or nitro group, a methyl or methoxy group which is substituted by 1 to 3 fluorine atoms, an ethyl or ethoxy group which is substituted by 1 to 5 fluorine atoms, $R_2$ is a hydrogen, fluorine or chlorine atom or a methyl, hydroxyl, methoxy, amino, $C_{1-2}$-alkylamino, di-$C_{1-2}$-alkylamino, $C_{1-2}$-alkylcarbonylamino, $C_{1-2}$-alkylsulphonylamino, trifluoromethylsulphonylamino or trifluoromethyl group, $R_3$ is a hydrogen, fluorine, chlorine or bromine atom or a methyl group and $R_c$ is a methylsulphinyl or methylsulphonyl group, a hydroxyl group, an ethoxy group which is substituted in the 2-position by a hydroxyl, methoxy, morpholino or (2-hydroxyethyl)amino group, a 2-propyloxy group which is substituted in the 1-position by a methoxy or dimethylamino group, a methoxy group which is substituted by a 2-tetrahydrofuryl, 2-tetrahydropyranyl or 3-methyl-3-oxetanyl group, a cyclobutyloxy group, a cyclopentyloxy group which is optionally substituted in the 3-position by a hydroxyl group, a cyclopentyloxy group in which the methylene group in the 3-position is replaced by an oxygen atom or by a methyl-imino group, a cyclohexyloxy group which can be substituted in the 2-, 3-or 4-position by a hydroxyl group or in the 4-position also by a di-($C_{1-2}$-alkyl)amino, methoxy, carboxyl, methoxycarbonyl, dimethylaminocarbonyl, methylaminocarbonyl, aminocarbonyl, acetylamino, methylsulphonylamino, methoxycarbonylamino or tert-butyloxycarbonylamino group, a cyclohexyloxy group in which the methylene group in the 3-position is replaced by a methyl-imino group or the methylene group in the 4-position is replaced by an oxygen atom or by a methyl-imino, acetyl-imino, tert-butyloxycarbonyl-imino, methoxycarbonyl-imino or methylsulphonyl-imino group, an allyloxy group, a 1-azetidinyl group, a 1-pyrrolidinyl group which can be substituted by 1 or 2 methyl groups, by a carboxyl, methoxycarbonyl, ethoxycarbonyl, aminocarbonyl, $C_{1-2}$-alkylaminocarbonyl, or di-($C_{1-2}$)-alkylamino-carbonyl group or in the 3-position by an amino, $C_{1-2}$-alkylamino, di-($C_{1-2}$-alkyl)amino, $C_{1-2}$-alkoxycarbonylamino, $C_{1-2}$-alkylcarbonylamino, $C_{1-2}$-alkylsulphonylamino, cyanoamino, formylamino or dimethylaminocarbonylamino group, a 1-pyrrolidinyl group in which two hydrogen atoms in the 3-position are replaced by an n-$C_{4-5}$-alkylene bridge, a 1-piperidinyl group which can be substituted by 1 to 4 methyl groups, by a phenyl, hydroxy-$C_{1-2}$-alkyl, carboxyl, $C_{1-2}$-alkoxycarbonyl, aminocarbonyl, $C_{1-2}$-alkylaminocarbonyl, di-($C_{1-2}$)-alkylaminocarbonyl, pyrrolidinocarbonyl or morpholinocarbonyl group or in the 3- or 4-position by a hydroxyl, $C_{1-2}$-alkoxy, amino, $C_{1-2}$-alkylamino, di-($C_{1-2}$)-alkylamino, $C_{1-2}$-alkylcarbonylamino, $C_{1-2}$-alkoxycarbonylamino, formylamino, cyanoamino, di-($C_{1-2}$-alkyl)aminocarbonylamino, $C_{1-2}$-alkylsulphonylamino or cyano group, a 1-piperidinyl group in which two hydrogen atoms in the 3-position or in the 4-position are replaced by an n-$C_{4-5}$-alkylene bridge or by an —O—$CH_2CH_2$—O— bridge, a 1-piperidinyl group which is substituted by 1 or 2 methyl groups or a phenyl group and additionally in the 3- or 4-position by a hydroxyl group, a 1-piperidinyl group in which two hydrogen atoms in the 2,5-position are replaced by a —$CH_2$— or —$CH_2CH_2$— bridge, a 1-piperidinyl group which is optionally substituted by 1 to 2 methyl groups and in which the methylene group in the 4-position is replaced by an oxygen or sulphur atom or by a carbonyl, sulphinyl, sulphonyl, imino, $C_{1-2}$-alkyl-imino, (2-hydroxyethyl)-imino, 2-(2-hydroxyethoxy)ethyl-imino, (2-aminoethyl)-imino, $C_{1-3}$-alkylaminocarbonylmethyl-imino, N-oxido-N-$C_{1-2}$-alkylamino, phenyl-imino, benzyl-imino, acetyl-imino or methanesulphonyl-imino group, a 1-azacyclohept-1-yl group in which two hydrogen atoms in the 3,6-position can be replaced by a —$CH_2CH_2$— group, a 1,2,3,4-tetrahydro-isoquinolin-2-yl or 2,3,4,5-tetrahydro-1H-3-benzazepin-3-yl group or an ($R_{10}NR_{11}$)— group in which $R_{10}$ is a hydrogen atom, a $C_{1-4}$-alkyl group or 2-hydroxyethyl group and $R_{11}$ is a hydrogen atom, a $C_{1-6}$-alkyl, $C_{3-6}$-cycloalkyl-methyl or phenyl-$C_{1-3}$-alkyl group, a $C_{3-6}$-cycloalkyl, allyl or propargyl group which is optionally substituted by 1 or 2 methyl groups, a phenyl group which can be substituted by a hydroxyl or methyl group or in the 4-position by an N-$C_{1-2}$-alkyl-$C_{1-2}$-alkylcarbonyl-amino, N-$C_{1-2}$-alkyl-(2-hydroxyethyl)amino, di-(2-hydroxyethyl)amino, 1-pyrrolidinyl, 2-oxo-1-pyrrolidinyl, 2-hydroxymethyl-1-pyrrolidinyl, 2-oxo-1-imidazolidinyl, 3-methyl-2-oxo-1-imidazolidinyl or morpholino group, a methyl group which is substituted by a carboxyl, $C_{1-2}$-alkoxycarbonyl, aminocarbonyl, $C_{1-2}$-alkylaminocarbonyl, di-$C_{1-2}$-alkylaminocarbonyl, pyrrolidinocarbonyl, piperidinocarbonyl or morpholinocarbonyl group, an ethyl group which is optionally substituted by a methyl group and is substituted in the 2-position by a hydroxyl, $C_{1-2}$-alkoxy, amino, $C_{1-2}$-alkylamino, di-$C_{1-2}$-alkylamino, acetylamino, 1-pyrrolidinyl, morpholino, 1-piperazinyl, 4-methyl-1-piperazinyl, 4-acetyl-1-piperazinyl, 4-aminocarbonyl-1-piperazinyl, 4-dimethylaminocarbonyl-1-piperazinyl, 4-methylaminocarbonyl-1-piperazinyl, 4-methylsulphonyl-1-piperazinyl, 4-methoxycarbonyl-1-piperazinyl or 4-cyano-1-piperazinyl group, a 2-hydroxyethyl group which is substituted in the ethyl part by a phenyl, 3-hydroxyphenyl, 4-hydroxyphenyl, 4-nitrophenyl or benzyl group, wherein the ethyl part of the abovementioned groups can additionally be substituted by a methyl, hydroxymethyl or methoxymethyl group, a methyl group which is substituted by a 1,4,7,10-tetraoxacyclododecyl, 1,4,7,10,13-pentaoxacyclopentadecyl or a 1,4,7,10,13,16-hexaoxacyclooctadecyl group, a 2,2,2-trifluoroethyl group, a propyl group which is substituted in the 3-position by a hydroxyl, cyano, carboxyl, aminocarbonyl, methylaminocarbonyl, dimethylaminocarbonyl, formylamino, methoxycarbonylamino, morpholino or 2-oxo-1-pyrrolidinyl group, a butyl group which is substituted in the 4-position by a hydroxyl group, a 3-butyl group which is substituted in the 1-position by a hydroxyl group and additionally in the 3-position by a methyl group, a 2-butyl group which is substituted in the 1-position by a hydroxyl group and additionally in the 3-position by a methyl group.

a 4-pentyl group which is substituted in the 1-position by a hydroxyl group and additionally in the 4-position by a methyl group, a 2,3-dihydroxypropyl, 3-amino-2-hydroxypropyl, tris-(3-hydroxypropyl)methyl, 1,3-dihydroxy-2-propyl, 1,3-dihydroxy-2-methyl-2-propyl or tris-(hydroxymethyl) methyl group, a 2-propyl group which is substituted in the 2-position by a hydroxylmethyl, $C_{1-2}$-alkoxymethyl, carboxyl, $C_{1-2}$-alkoxycarbonyl, aminocarbonyl, N-$C_{1-2}$-alkylaminocarbonyl, N,N-di-$C_{1-2}$-alkylaminocarbonyl, pyrrolidinocarbonyl, morpholinocarbonyl or (2-hydroxyethyl)aminocarbonyl group, a 4-tetrahydropyranyl, tetrahydrofurfuryl, 1-deoxy-1-D-sorbityl or 2-(2-hydroxyethyloxy)ethyl group, a cyclopentyl group which is substituted in the 2- or 3-position by a hydroxyl group or in the 1-position by a hydroxymethyl group, a cyclohexyl group which is substituted in the 2-, 3- or 4-position by a hydroxymethyl, hydroxyl, $C_{1-2}$-alkoxy, ($C_{1-4}$-alkoxy)-carbonylamino, amino, $C_{1-2}$-alkylamino, di-$C_{1-2}$-alkylamino, carboxyl, $C_{1-2}$-alkoxycarbonyl, aminocarbonyl, $C_{1-2}$-alkylaminocarbonyl, di-$C_{1-2}$-alkylaminocarbonyl, N-oxido-di-$C_{1-2}$-alkylamino, pyrrolidinocarbonyl, morpholinocarbonyl, $C_{1-2}$-alkylcarbonyl-amino or $C_{1-2}$-alkylsulphonylamino group and can additionally be substituted by a methyl group, a cyclohexyl group which is substituted in the 4-position by a 1-pyrrolidinyl, 2-oxo-1-pyrrolidinyl, 2-hydroxymethyl-1-pyrrolidinyl, N-$C_{1-2}$-alkyl-(2-hydroxyethyl)amino, di-(2-hydroxyethyl)amino, N-$C_{1-2}$-alkyl-$C_{1-2}$-alkylcarbonylamino, morpholino, 2-oxo-1-imidazolidinyl, 3-methyl-2-oxo-1-imidazolidinyl, carboxy-$C_{1-2}$-alkyl, carboxy-$C_{1-2}$-alkoxy, $C_{1-2}$-alkoxycarbonyl-$C_{1-2}$-alkyl, $C_{1-2}$-alkoxycarbonyl-$C_{1-2}$-alkoxy, aminocarbonyl-$C_{1-2}$-alkyl, aminocarbonyl-$C_{1-2}$-alkoxy, $C_{1-2}$-alkylamino-carbonyl-$C_{1-2}$-alkyl, $C_{1-2}$-alkylamino-carbonyl-$C_{1-2}$-alkoxy, di-$C_{1-2}$-alkylamino-carbonyl-$C_{1-2}$-alkyl, di-$C_{1-2}$-alkylamino-carbonyl-$C_{1-2}$-alkoxy, pyrrolidinocarbonyl-$C_{1-2}$-alkyl, pyrrolidinocarbonyl-$C_{1-2}$-alkoxy, morpholinocarbonyl-$C_{1-2}$-alkyl, morpholinocarbonyl-$C_{1-2}$-alkoxy, piperidinocarbonyl-$C_{1-2}$-alkyl or piperidinocarbonyl-$C_{1-2}$-alkoxy group, a cyclohexyl group in which two hydrogen atoms in the 4-position are replaced by an oxo group or an n-$C_{4-5}$-alkylene bridge, a cyclohexyl group in which the methylene group in the 4-position is replaced by an imino, $C_{1-2}$-alkyl-imino, phenyl-$C_{1-2}$-alkyl-imino, N-methyl-N-oxido-imino, formyl-imino, $C_{1-2}$-alkylcarbonyl-imino, $C_{1-2}$-alkylsulphonyl-imino, $C_{1-2}$-alkoxycarbonyl-imino, cyano-imino, aminocarbonyl-imino, $C_{1-2}$-alkylaminocarbonyl-imino or N,N-di-$C_{1-2}$-alkylaminocarbonylimino group, a cyclohexyl group in which the methylene group in the 3-position is replaced by an imino, $C_{1-2}$-alkyl-imino, $C_{1-2}$-alkylcarbonyl-imino, $C_{1-2}$-alkylsulphonyl-imino or $C_{1-2}$-alkoxycarbonyl-imino group, a cyclopentyl group in which the methylene group in the 3-position is replaced by an oxygen atom or an imino, $C_{1-2}$-alkyl-imino, formyl-imino, $C_{1-2}$-alkylcarbonyl-imino, $C_{1-2}$-alkylsulphonyl-imino, $C_{1-2}$-alkoxycarbonyl-imino, cyano-imino or N,N-di-$C_{1-2}$-alkylaminocarbonylimino group, a cyclohexylmethyl group, wherein the cyclohexyl part is substituted in the 4-position by a carboxyl, $C_{1-2}$-alkoxycarbonyl, N,N-di-$C_{1-2}$-alkylaminocarbonyl or morpholinocarbonyl group, a norbornan-2-yl, norbornan-2-yl-methyl, 5-norbornen-2-yl-methyl, bornyl, 3-quinuclidinyl or adamantyl group or $R_{10}$ is a hydrogen atom or a methyl group and $R_{11}$ is a hydroxyl or methoxy group, their tautomers, their stereoisomers and their salts.

6. Pyrimido[5,4-d]pyrimidine I according to claim 1 or claim 2, in which $R_a$ is a hydrogen atom or a methyl group, $R_b$ is a 2-naphthyl or 5-indanyl group or a phenyl group which is substituted by the radicals $R_1$ to $R_3$, wherein $R_1$ is a hydrogen, fluorine, chlorine, bromine or iodine atom or a methyl, ethyl, tert-butyl, trifluoromethyl, ethynyl, methoxy, cyclopropyl, trifluoromethoxy, cyano, ethoxycarbonyl or nitro group, $R_2$ is a hydrogen, fluorine or chlorine atom or an amino, methyl or trifluoromethyl group and $R_3$ is a hydrogen, chlorine or bromine atom, and $R_c$ is a hydroxyl, cyclopentyloxy, 2-[(2-hydroxyethyl)amino]-ethoxy, methylsulphinyl or methylsulphonyl group, a 1-azetidinyl group or a 1-pyrrolidinyl group which is optionally substituted by one or two methyl groups, a 1-piperidinyl group which is substituted by a hydroxymethyl group, a 1-piperidinyl group which is optionally substituted by one or two methyl groups and in which the methylene group in the 4-position can be replaced by an oxygen or sulphur atom or by a carbonyl, sulphinyl, sulphonyl, imino, methyl-imino, N-oxido-N-methyl-imino, 2-propylaminocarbonyl-methyl-imino, phenyl-imino, benzyl-imino, acetyl-imino or methylsulphonyl-imino group, a 1-piperidinyl group which is substituted in the 3-position by a hydroxyl or diethylaminocarbonyl group or in the 4-position by a hydroxyl, carboxyl, methoxycarbonyl, aminocarbonyl, methylaminocarbonyl, dimethylaminocarbonyl, pyrrolidinocarbonyl, morpholinocarbonyl, amino, acetylamino, methoxycarbonylamino, formylamino, cyanoamino, dimethylaminocarbonylamino, methylsulphonylamino or phenyl group, a 4-hydroxy-4-phenyl-1-piperidinyl group, a 1,2,3,4-tetrahydro-isoquinolin-2-yl or 2,3,4,5-tetrahydro-1H-3-benzazepin-3-yl group, a 1-piperidinyl group in which two hydrogen atoms in the 4-position are replaced by an —$OCH_2CH_2$—O— bridge, a 1-azacyclohept-1-yl group in which two hydrogen atoms in the 3- and 6-position are replaced by a —$CH_2$—$CH_2$— group or an ($R_{10}NR_{11}$)— group, in which $R_{10}$ is a hydrogen atom, a $C_{1-4}$-alkyl group or a 2-hydroxyethyl group and $R_{11}$ is a hydrogen atom, a phenyl group which is optionally substituted by a methyl group, a phenyl group which is substituted in the 4-position by a morpholino or 2-(hydroxymethyl)-1-pyrrolidinyl group, a $C_{1-6}$-alkyl, $C_{3-6}$-cycloalkyl, phenyl-$C_{1-3}$-alkyl, cyclopropylmethyl, allyl, propargyl, 2-hydroxyethyl, 1-hydroxy-2-propyl, 3-hydroxypropyl, 4-hydroxybutyl, 2-methyoxyethyl, 1-adamantyl, norbornan-2-yl, aminocarbonylmethyl, 2-(dimethylamino)ethyl, 3-quinuclidinyl, 2,2,2-trifluoroethyl, 4-piperidinyl, 1-methyl-4-piperidinyl, 1-methyl-1-oxido-4-piperidinyl, 1-ethoxycarbonyl-4-piperidinyl, 1-benzyl-4-piperidinyl, 2-(2-hydroxyethoxy)ethyl, 4-tetrahydropyranyl, 1-hydroxy-2-methyl-2-propyl, 1-methoxy-2-methyl-2-propyl, 2-(methylaminocarbonyl)-2-propyl, 2,3-dihydroxy-1-propyl, 2-(morpholino)ethyl, 1-deoxy-1-D-sorbityl, 3-(2-oxo-1-pyrrolidinyl)-propyl, tris-(hydroxymethyl)methyl, 1,3-dihydroxy-2-propyl, 1,3-dihydroxy-2-methyl-2-propyl or bornyl group, a 2-hydroxyethyl group which is substituted in the 2-position by a phenyl group and in the 1-position additionally by a methyl or hydroxymethyl group, a methylcyclohexyl, 4-carboxy-cyclohexyl, 4-methoxycarbonylcyclohexyl, 4-dimethylaminocarbonyl-cyclohexyl, 4-(1-pyrrolidinylcarbonyl)-cyclohexyl, 4-(morpholinocarbonyl)cyclohexyl, 4-[2-(methoxycarbonyl)ethyl]cyclohexyl, 4-(2-carboxyethyl)cyclohexyl, 4-(tert-butyloxycarbonylamino)cyclohexyl, 4-methoxycyclohexyl, 4-aminocyclohexyl, 4-(dimethylamino)cyclohexyl, 4-(N,N-dimethyl-N-oxido-amino)cyclohexyl, 4-(acetylamino)-cyclohexyl, 4-(methylsulphonylamino)-cyclohexyl, 2-hydroxycyclohexyl, 4-hydroxycyclohexyl, 4-(hydroxymethyl)-cyclohexyl, 4-hydroxy-4-methyl-cyclohexyl or 4-oxocyclohexyl group, a methyl group which is substituted by a 1,4,7,10,13-pentaoxacyclopentadecyl or a 1,4,7,10,13,16-hexaoxacyclooctadecyl group, or $R_{10}$ is a methyl group and $R_{11}$ is a methoxy group, their tautomers, their stereoisomers and their salts.

7. The pyrimido[5,4-d]-pyrimidine according to claim 1 or claim 2:

(1) 4-[(3,4-Dichlorophenyl)amino]-6-[(trans-4-hydroxycyclohexyl)-amino]-pyrimido-[5,4-d]-pyrimidine, (2) 4-[(3-Chloro-4-fluoro-phenyl)amino]-6-[(trans-4-hydroxycyclohexyl)-amino]-pyrimido-[5,4-d]-pyrimidine,
(3) 4-[(3-Bromophenyl)amino]-6-[(trans-4-hydroxycyclohexyl)-amino]-pyrimido-[5,4-d]-pyrimidine,
(4) 4-[(3-Chlorophenyl)amino]-6-(cyclopropylamino)-pyrimido-[5,4-d]-pyrimidine,
(5) 4-[(3-Methylphenyl)amino]-6-(4-amino-1-piperidinyl)-pyrimido-[5,4-d]-pyrimidine,
(6) 4-[(3-Methylphenyl)amino]-6-[(trans-4-aminocyclohexyl)-amino]-pyrimido[5,4-d]-pyrimidine,
(7) 4-[(3-Methylphenyl)amino]-6-(N-(trans-4-hydroxycyclohexyl)-N-methylamino)-pyrimido-[5,4-d]-pyrimidine,
(8) 4-[(3-Methylphenyl)amino]-6-(4-methoxycarbonylamino-1-piperidinyl)-pyrimido-[5,4-d]-pyrimidine,
(9) 4-[(3-Methylphenyl)amino]-6-[trans-4-(morpholinocarbonyl)-cyclohexylamino]-pyrimido-[5,4-d]-pyrimidine,
(10) 4-[(3-Methylphenyl)amino]-6-[trans-4-(pyrrolidinocarbonyl)cyclohexylamino]-pyrimido-[5,4-d]-pyrimidine,
(11) 4-[(3-Chloro-4-fluoro-phenyl)amino]-6-[N-(trans-4-hydroxycyclohexyl)-N-methyl-amino]-pyrimido-[5,4-d]-pyrimidine,
(12) 4-[(4-Amino-3,5-dichloro-phenyl)amino]-6-[(triamino]-pyrimidcyclohexyl)-amino]-pyrimido-[5,4-d]-pyrimidine,
(13) 4-[(3-Chloro-4-fluoro-phenyl)amino]-6-[2-(morpholino)-ethylamino]-pyrimido-[5,4-d]-pyrimidine,
(14) 4-[(4-Amino-3,5-dibromo-phenyl)amino]-6-[(trans4-hydroxycyclohexyl)-amino]-pyrimido-[5,4-d]-pyrimidine,
(15) 4-[(3-Chloro-4-fluoro-phenyl)amino]-6-morpholino-pyrimido-[5,4-d]-pyrimidine,
(16) 4-[(3-Chloro-4-fluoro-phenyl)amino]-6-(1-hydroxy-2-methyl-2-propylamino)-pyrimido-[-d]-pyrimidine,
(17) 4-[(3-Chloro-4-fluoro-phenyl)amino]-6-(1-hydroxy-2-propylamino)-pyrimido-[5,4-d]-pyrimidine,
(18) 4-[(3-Chloro-4-fluoro-phenyl)amino]-6-(1,3-dihydroxy-2-propylamino)-pyrimido-[5,4-d]-pyrimidine,
(19) 4-[(3-Chloro-4-fluoro-phenyl)amino]-6-[4-amino-1-piperidinyl]-pyrimido-[5,4-d]-pyrimidine,
(20) 4-[(3-Methylphenyl)amino]-6-(4-piperidinyl-amino)-pyrimido-[5,4-d]-pyrimidine,
(21) 4-[(3-Methylphenyl)amino]-6-(4-formylamino-1-piperidinyl)-pyrimido-[5,4-d]-pyrimidine,
(22) 4-[(3-Methylphenyl)amino]-6-[(1-ethoxycarbonyl-4-piperidinyl)amino]-pyrimido-[5,4-d]-pyrimidine,
(23) 4-[(3-Methylphenyl)amino]-6-[(3-quinuclidinyl)amino]-pyrimido-[5,4-d]-pyrimidine,
(24) 4-[(3-Chloro-4-fluoro-phenyl)amino]-6-[(4-aminocyclohexyl)amino]-pyrimido-[5,4-d]-pyrimidine,
(25) 4-[(3-Chloro-4-fluoro-phenyl)amino]-6-(4-piperidinyl-amino)-pyrimido-[5,4-d]-pyrimidine,
(26) 4-[(3-Chloro-4-fluoro-phenyl)amino]-6-[trans-4-(morpholinocarbonyl)cyclohexylamino]-pyrimido-[5,4-d]-pyrimidine,
(27) 4-[(3-Chloro-4-fluoro-phenyl)amino]-6-[trans-4-(pyrrolidinocarbonyl)cyclohexylamino]-pyrimido-[5,4-d]-pyrimidine,
(28) 4-[(4-Fluorophenyl)amino]-6-(cyclopropylamino)-pyrimido-[5,4-d]-pyrimidine,
(29) 4-[(3-Chloro-4-fluoro-phenyl)amino]-6-(cyclopropylamino)-pyrimido-[5,4-d]-pyrimidine,
(30) 4-[(3,4-Dichlorophenyl)amino]-6-(cyclopropylamino)-pyrimido-[5,4-d]-pyrimidine,
(31) 1-[(3-Chloro-4-fluoro-phenyl)amino]-6-(1-methyl-4-piperidinyl-amino)-pyrimido-[5,4-d]-pyrimidine, or
(32) 4-[(3-Chloro-4-fluoro-phenyl)amino]-6-[1-trans-4-(dimethylaminocyclohexyl)amino]-pyrimido-[5,4-d]-pyrimidine, or a pharmaceutically acceptable salt thereof.

8. A pharmaceutical composition of matter comprising a pyrimido[5,4-d]pyrimidine according to claim 1 or claim 2 and a pharmaceutically acceptable carrier or diluent.

9. A method of treating disease in a warm-blooded animal by inhibition of signal transduction mediated by tyrosine kinases which comprises administering to the animal a therapeutically effective amount of a pyrimido[5,4-d]pyrimidine according to claim 1 or claim 2.

10. The pyrimido[5,4-d]-pyrimidine according to claim 1 or 2 which is: 4-[(3-chloro-4-fluorophenyl)amino]-6-(1-methyl-4-piperidinyl-amino)-pyrimido[5,4-d]pyrimidine.

11. The pyrimido[5,4-d]-pyrimidine according to claim 1 or 2 which is: 4-[(3-chloro-4-fluorophenyl)amino]-6-[1-(trans-4-dimethylaminocyclohexyl)amino]-pyrimido[5,4-d]pyrimidine.

* * * * *